(12) United States Patent
Jasuja et al.

(10) Patent No.: US 10,386,375 B2
(45) Date of Patent: Aug. 20, 2019

(54) METHODS AND SYSTEMS FOR THE DIAGNOSIS AND TREATMENT OF ANDROGEN DISORDERS

(71) Applicant: Function Promoting Therapies LLC, Weston, MA (US)

(72) Inventors: Ravi Jasuja, Quincy, MA (US); Shalender Bhasin, Weston, MA (US); Mikhail N. Zakharov, Rockville, MD (US)

(73) Assignee: Function Promoting Therapies LLC, Weston, MA (US)

( * ) Notice: Subject to any disclaimer, the term of this patent is extended or adjusted under 35 U.S.C. 154(b) by 958 days.

(21) Appl. No.: 14/772,554

(22) PCT Filed: Mar. 4, 2014

(86) PCT No.: PCT/US2014/020223
§ 371 (c)(1),
(2) Date: Sep. 3, 2015

(87) PCT Pub. No.: WO2014/138026
PCT Pub. Date: Sep. 12, 2014

(65) Prior Publication Data
US 2016/0018420 A1    Jan. 21, 2016

Related U.S. Application Data

(60) Provisional application No. 61/772,054, filed on Mar. 4, 2013.

(51) Int. Cl.
*G16H 20/10* (2018.01)
*G01N 33/74* (2006.01)
*H01J 49/00* (2006.01)

(52) U.S. Cl.
CPC .......... *G01N 33/743* (2013.01); *G16H 20/10* (2018.01); *H01J 49/0027* (2013.01); *G01N 2800/34* (2013.01)

(58) Field of Classification Search
None
See application file for complete search history.

(56) References Cited

U.S. PATENT DOCUMENTS

| | | |
|---|---|---|
| 2002/0061869 A1 | 5/2002 | Lichten |
| 2005/0042268 A1 | 2/2005 | Aschkenasy et al. |
| 2006/0211059 A1 | 9/2006 | Taneja |
| 2006/0211664 A1 | 9/2006 | Dudley |
| 2010/0273275 A1 | 10/2010 | Boone |

OTHER PUBLICATIONS

Ho et al., Calculated free testosterone in men: comparison of four equations and with free androgen index. Ann Clin Biochem. Sep. 2006;43(Pt 5):389-97.

*Primary Examiner* — John S Brusca
*Assistant Examiner* — Olivia M Wise
(74) *Attorney, Agent, or Firm* — Wolf, Greenfield & Sacks, P.C.

(57) ABSTRACT

The technology described herein is directed to the diagnosis and treatment of androgen disorders and/or deficiencies, e.g. low testosterone.

19 Claims, 15 Drawing Sheets

Model

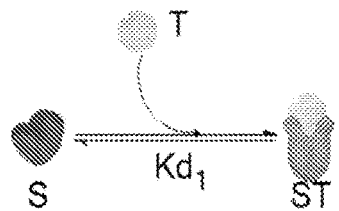

Sodergard, Vermulen model
Non-interacting monomers
Equal affinities; Kd = 1nM

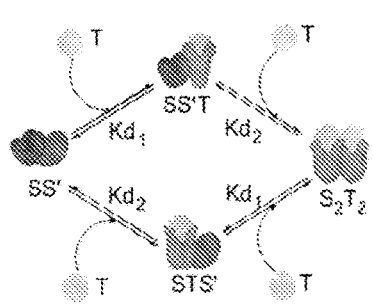

Non-interacting monomers
Unequal affinities; $Kd_1$ = 1nM;
$Kd_2$ allowed to vary for fit

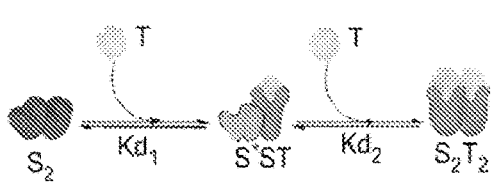

Positive cooperativity
Interacting monomers
$Kd_2$=1nM, $Kd_1$ allowed to vary
and $Kd_2 < Kd_1$

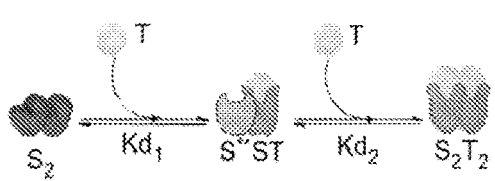

Negative cooperativity
Interacting monomers
$Kd_1$=1nM, $Kd_2$ allowed to vary
and $Kd_2 > Kd_1$

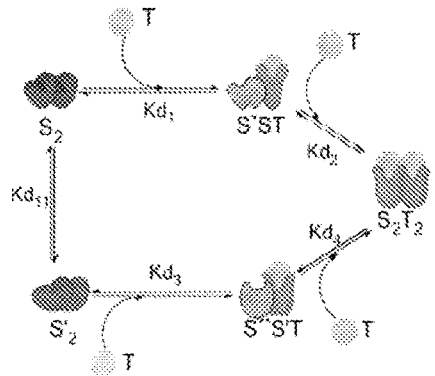

The New Multi-Step Dynamic
Binding Model with Complex
Allostery

Fig. 6

METHODS AND SYSTEMS FOR THE DIAGNOSIS AND TREATMENT OF ANDROGEN DISORDERS

CROSS-REFERENCE TO RELATED APPLICATIONS

This application is a national stage filing under 35 U.S.C. § 371 of international PCT application PCT/US2014/020223, filed Mar. 4, 2014, which claims priority to U.S. Provisional Application No. 61/772,054 filed on Mar. 4, 2013, the contents of which are incorporated herein by reference.

TECHNICAL FIELD

The technology described herein relates to the diagnosis and treatment of androgen disorders and/or deficiencies.

BACKGROUND

Testosterone (T) is a primary androgenic hormone produced predominantly in the interstitial cells of the testes and is responsible for normal growth, development and maintenance of male sex organs and secondary sex characteristics (e.g., deepening voice, muscular development, facial hair, etc.). Throughout adult life, testosterone is necessary for proper functioning of the testes and its accessory structures, prostate and seminal vesicle; for sense of well-being; and for maintenance of libido, erectile potency, muscle mass, and bone health. Testosterone deficiency is insufficient secretion of T characterized by low serum T concentrations and can give rise to medical conditions (e.g., hypogonadism) in males. Symptoms associated with male hypogonadism include impotence and decreased sexual desire, fatigue and loss of energy, low mood and depressive symptoms, regression of secondary sexual characteristics, decreased muscle mass, and increased fat mass. Furthermore, hypogonadism in men is a risk factor for anemia, osteoporosis, metabolic syndrome, type II diabetes and cardiovascular disease.

Circulating free testosterone (FT) levels have been used widely in the diagnosis and treatment of hypogonadism in men. Testosterone is the second most frequently ordered endocrine test. In 2012, nearly 4 million free testosterone tests were performed in the USA alone. A number of direct and indirect methods —equilibrium dialysis, ultrafiltration, tracer analog methods, and calculations based on homogenous sex-hormone binding globulin (SHBG) and testosterone (SHBG:T) binding equations —have been developed for the determination of FT levels. Due to experimental complexities in FT measurements, the Endocrine Society expert panel has recommended the use of calculated FT (cFT) as an appropriate approach for estimating FT. Expert panels have expressed concern about the accuracy and methodological complexity of the available assays for FT (Rosner et al 2007, Sodergard et al 1982, Vermeulen et al 1971).

SUMMARY

Described herein is the inventors' demonstration that the prevailing model of testosterone's binding to SHBG, used in the current methods of testing and diagnosis is flawed, and their further discovery of an improved model that permits methods, assays, and systems with greater accuracy and reliability in measuring testosterone levels. The multi-step dynamic binding model with complex allostery described herein is a new model for calculation of free testosterone. The multi-step dynamic binding model with complex allostery model is a modified ensemble allostery model that takes into consideration the specific SHBG-Testosterone binding interaction described herein.

In one aspect, described herein is a computer implemented method for an assay, comprising: on a device having one or more processors and a memory storing one or more programs for execution by the one or more processors, the one or more programs including instructions for: a) receiving data from measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer; and c) calculating the free testosterone concentration in the individual using the New Multi-Step Dynamic Binding Model with Complex Allostery encompassing readjustment of a first equilibria between the microstates upon binding of a first testosterone molecule to the first monomer and an allosteric interaction between two binding sites of the SHBG dimer.

In one aspect, described herein is a computer system for an assay, comprising: one or more processors; and memory to store: one or more programs, the one or more programs comprising: instructions for: a) receiving data from measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); and c) calculating the free testosterone concentration in the individual using the New Multi-Step Dynamic Binding Model with Complex Allostery encompassing readjustment of a first equilibria between the microstates upon binding of a first testosterone molecule to the first monomer and an allosteric interaction between two binding sites of the SHBG dimer.

In one aspect, described herein is a non-transitory computer-readable storage medium storing one or more programs for treating an individual suspected of having an androgen disorder, the one or more programs for execution by one or more processors of a computer system, the one or more programs comprising instructions for: a) receiving data from measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); and c) calculating the free testosterone concentration in the individual using the New Multi-Step Dynamic Binding Model with Complex Allostery encompassing readjustment of a first equilibria between the microstates upon binding of a first testosterone molecule to the first monomer and an allosteric interaction between two binding sites of the SHBG dimer.

In one aspect, described herein is an assay comprising the steps of: a) measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); and c) calculating the free testosterone concentration in the individual using the New Multi-Step Dynamic Binding Model with Complex Allostery encompassing readjustment of a first equilibria between the microstates upon binding of a first testosterone molecule to the first monomer and an allosteric interaction between two binding sites of the SHBG dimer In some embodiments of any of the foregoing aspects, the step of attributing can be performed according to FIGS. 2, 3, 5, and 7. In some embodiments, of any of the foregoing aspects, the step of calculating can be performed according to FIG. 7 or Example 5. In some embodiments of any of the foregoing aspects, the assay, method, system, or medium can further comprise the step of determining the concentration of at least one non-testosterone steroid. In some embodiments, the non-testosterone steroid can be selected from the group consisting of an estradiol steroid, an estrone steroid, and a dihydrotestosterone steroid. In some embodiments of any of the foregoing aspects, the total SHBG concentration, the total testosterone concentration, and the total albumin concentration is determined using an assay selected from the group consisting of an immunoassay, a binding assay, and a mass-spectrometry assay. In some embodiments of any of the foregoing aspects, instead of steps a-c, the data received is a previously calculated concentration of free testosterone.

In one aspect, described herein is a computer implemented method for treating an individual suspected of having an androgen disorder, comprising: on a device having one or more processors and a memory storing one or more programs for execution by the one or more processors, the one or more programs including instructions for: a) receiving data from measuring i) a total SHBG concentration, ii) a total testosterone concentration, and iii) a total albumin concentration in a biological sample obtained from an individual suspected of having an androgen disorder, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using a New Multi-step Dynamic Binding Model with Complex Allostery encompassing readjustment of a first equilibria between the microstates upon binding of a first testosterone molecule to the first monomer and an allosteric interaction between two binding sites of the SHBG dimer; d) sending a signal for administering a pharmaceutically effective amount of testosterone to an individual having a free testosterone concentration below the lower limit of a normal free testosterone concentration from a healthy individual (e.g., in one embodiment, the lower limit is 114.6 pg/ml); and e) sending a signal for not administering a pharmaceutically effective amount of testosterone to an individual having a free testosterone concentration above the lower limit of the normal free testosterone concentration from a healthy individual (e.g., in one embodiment, the lower limit is 114.6 pg/ml).

In one aspect, described herein is a computer system for treating an individual suspected of having an androgen disorder, comprising: one or more processors; and memory to store: one or more programs, the one or more programs comprising: instructions for: a) receiving data from measuring i) a total SHBG concentration, ii) a total testosterone concentration, and iii) a total albumin concentration in a biological sample obtained from an individual suspected of having an androgen disorder, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer; d) sending a signal for administering to a pharmaceutically effective amount of testosterone to an individual having a free testosterone concentration (based on a, b, c, d above or obtained otherwise) below the lower limit of a normal free testosterone concentration from a healthy individual (e.g., in one embodiment, the lower limit is 114.6 pg/ml); and e) sending a signal for not administering a pharmaceutically effective amount of testosterone to an individual having a free testosterone concentration (based on a, b, c, d above or obtained otherwise) above the lower limit of the normal free testosterone concentration from a healthy individual (e.g., in one embodiment, the lower limit is 114.6 pg/ml).

In one aspect, described herein is a non-transitory computer-readable storage medium storing one or more programs for treating an individual suspected of having an androgen disorder, the one or more programs for execution by one or more processors of a computer system, the one or more programs comprising instructions for: a) receiving data from measuring i) a total SHBG concentration, ii) a total testosterone concentration, and iii) a total albumin concentration in a biological sample obtained from an individual suspected of having an androgen disorder, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using New Multi-step Dynamic Binding Model with Complex Allostery encompassing readjustment of a first equilibria between the microstates upon binding of a first testosterone molecule to the first monomer and an allosteric interaction between two binding sites of the SHBG dimer; d) sending a signal for administering a pharmaceutically effective amount of testosterone to an individual having a free testosterone concentration below the lower limit of a normal free testosterone concentration from a healthy individual (e.g., in one embodiment, below 114.6 pg/ml); and e) sending a signal for not administering a pharmaceutically effective amount of testosterone to an individual having a free testosterone concentration above the lower limit of the normal free testosterone concentration from a healthy individual (e.g., in one embodiment, above 114.6 pg/ml, the lower limit of this assay).

In one aspect, described herein is a method for treating an individual suspected of having an androgen disorder comprising: a) administering a pharmaceutically effective amount of testosterone to an individual who has had a free testosterone level determined by measuring i) a total SHBG concentration, ii) a total testosterone concentration, and iii) a total albumin concentration in a biological sample from the individual suspected of having an androgen disorder; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using an the New Multi-step Dynamic Binding Model with Complex Allostery encompassing readjustment of a first equilibria between the microstates upon binding of a first testosterone molecule to the first monomer and an allosteric interaction between two binding sites of the SHBG dimer; d) administering a pharmaceutically effective amount of testosterone to an individual having a free testosterone concentration below the lower limit of a normal free testosterone concentration from a healthy individual (e.g., in one embodiment, below 114.6 pg/ml); and e) not administering a pharmaceutically effective amount of testosterone to an individual having a free testosterone concentration above the lower limit of the normal free testosterone concentration from a healthy individual (e.g., in one embodiment, above 114.6 pg/ml, the lower limit of this assay).

In one aspect, described herein is a computer implemented method for determining a need for adjustment of a dose of testosterone administered to an individual with hypogonadism, androgen deficiency syndrome, or any other condition for which testosterone therapy is indicated, comprising: on a device having one or more processors and a memory storing one or more programs for execution by the one or more processors, the one or more programs including instructions for: a) receiving data from determining the concentration of free testosterone in an individual receiving testosterone therapy at a first dose, wherein the concentration of free testosterone is determined by measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer and; d) sending a signal for providing a second (adjusted) dose of testosterone that is higher than the first dose when the free testosterone concentration is below the lower end of the target therapeutic range (e.g. 164 pg/ml); and e) sending a signal for providing a second (adjusted) dose of testosterone that is lower than the first dose when the free testosterone concentration is above the upper end of the target therapeutic range (e.g. 314 pg/ml). In some embodiments, the system can further comprise the step of receiving data of the first dose of testosterone administered to the individual.

In one aspect, described herein is a computer system for determining a need for adjustment of a dose of testosterone administered to an individual, comprising: one or more processors; and memory to store: one or more programs, the one or more programs comprising: instructions for: a) receiving data from determining the concentration of free testosterone in an individual receiving testosterone therapy at a first dose, wherein the concentration of free testosterone is determined by measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer; d) sending a signal for providing a second dose of testosterone that is higher than the first dose when the free testosterone concentration is below the lower end of the target therapeutic range (e.g. 164 pg/ml); and e) sending a signal for providing a second dose of testosterone that is lower than the first dose when the free testosterone concentration is above the upper end of the target therapeutic range (e.g. 314 pg/ml).

In one aspect, described herein is a non-transitory computer-readable storage medium storing one or more programs for determining a need for adjustment of a dose of testosterone administered to an individual, the one or more programs for execution by one or more processors of a computer system, the one or more programs comprising instructions for: a) receiving data from determining the concentration of free testosterone in an individual receiving testosterone therapy at a first dose, wherein the concentration of free testosterone is determined by measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer; d) sending a signal for providing a second dose of testosterone that is higher than the first dose when the free testosterone concentration is below the lower end of the target therapeutic range (e.g. 164 pg/ml); and e) sending a signal for providing a second dose of testosterone that is lower than the first dose when the free testosterone concentration is above the upper end of the target therapeutic range (e.g. 314 pg/ml).

In one aspect, described herein is a method for determining a need for adjustment of a dose of testosterone administered to an individual comprising a) determining the concentration of free testosterone in an individual receiving testosterone therapy at a first dose, wherein the concentration of free testosterone is determined by b) measuring i) a total SHBG concentration, ii) a total testosterone concentration, and iii) a total albumin concentration in a biological sample obtained from an individual, to determine free testosterone concentration from the individual; c) attributing at least two distinct interconverting microstates of an unliganded SHBG dimer having a first monomer and a second monomer by applying the New Multi-Step Dynamic Binding Model with Complex Allostery to the data of steps a) and b); d) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer; e) providing a second dose of testosterone that is higher than the first dose when the free testosterone concentration is below the lower end of the target therapeutic range (e.g. 164 pg/ml); and f) providing a second dose of testosterone that is lower than the first dose when the free testosterone concentration is above the upper end of the target therapeutic range (314 pg/ml).

In some embodiments of any of the foregoing aspects, the step of attributing can be performed according to FIGS. 2, 3, 5, and 7. In some embodiments, of any of the foregoing aspects, the step of calculating can be performed according to FIG. 7 or Example 5. In some embodiments of any of the foregoing aspects, the individual is a male over the age of 35. In some embodiments of any of the foregoing aspects, the androgen disorder is selected from the group consisting of a testosterone deficiency, an androgen deficiency, a hyperandrogenic disorder, an androgen expressing tumor, and a hypogonadism disorder. In some embodiments of any of the foregoing aspects, the androgen disorder is a hyperandrogenic disorder selected from the group consisting of an acne disorder, a hirsutism disorder, and an androgenic alopecia disorder. In some embodiments of any of the foregoing aspects, the individual has been diagnosed with a disease selected from the group consisting of: diabetes, human immunodeficiency virus (HIV), hepatitis B, hepatitis C, hypothyroidism or hyperthyroidism, androgen insensitivity, acromegaly, anorexia, muscular dystrophy, liver disease, cancer cachexia, malnutrition, nephrotic syndrome, and obesity, and other conditions in which SHBG or albumin concentrations are altered. In some embodiments of any of the foregoing aspects, the assay, method, system, or medium can further comprise the step of classifying the individual into categories based on additional clinical symptoms. In some embodiments of any of the foregoing aspects, the assay, method, system, or medium can further comprise the step of using the free testosterone concentration determined using the new Multistep Dynamic Binding Model with Complex Allostery to determine the dose or to individually adjust the dose of a formulation of testosterone for the treatment of a medical disease, taking into account patient's age, body weight and body mass index, medical conditions, including any co-morbid conditions, albumin and SHBG, and/or luteinizing hormone (LH) and follicle stimulating hormone (FSH) concentrations, and other patient-specific factors. In some embodiments of any of the foregoing aspects, instead of steps a-c, the data received is a previously calculated concentration of free testosterone.

BRIEF DESCRIPTION OF THE DRAWINGS

FIG. 1A depicts a graph of free testosterone concentrations in samples derived from a randomized testosterone trial (The TED study) were measured using the equilibrium dialysis and plotted against those calculated using the Vermeulen/Sodergard/Mazer equation. Calculated free T concentrations differed systematically from the measured values. FIG. 1B depicts a Bland Altman plot revealing substantial discrepancy between the calculated and measured free T concentrations.

FIG. 2A depicts a graph demonstrating that binding isotherms display complex behavior. Graded concentrations of testosterone were incubated overnight with various SHBG concentrations and the amount of bound testosterone was plotted against total T (added) concentrations (squares) 20 nM, (triangles) 10 nM, (circles) 5 nM SHBG. The fit curves represent the result of the linked fit of data to the new Multi-step Dynamic Binding Model with Complex Allostery (FIG. 3). FIG. 2B depicts a graph of the depletion of free testosterone by varying SHBG concentration which is best described by the new Multi-step Dynamic Binding Model with Complex Allostery. Shown is concentration of free testosterone in the equilibrium dialysis experiment. One side of the equilibrium dialysis membrane has varying concentration of SHBG in buffer, the other one has plain buffer. Constant concentration of testosterone is added to each well of multi-well dialyzer: (triangles) 8.7 nM. Curves are the result of the linked fit of data in Panel B to the new Multi-step Dynamic Binding Model with Complex Allostery (FIG. 3). FIG. 2C depicts a graph of the heat of T: SHBG association measured by isothermal calorimetry (ITC). Presented is the integrated ITC curve with buffer heats subtracted. SHBG starting concentration is 5 $\mu$M. Experimental points are shown by squares, fit to the model in FIG. 3 is shown by a solid line.

FIG. 4A depicts a graph of a comparison of the free testosterone concentration calculated by the Vermeulen equation and the new algorithm based on the new Multi-step Dynamic Binding Model with Complex Allostery to that measured by equilibrium dialysis in samples from a randomized testosterone trial in men. (■) free testosterone concentrations derived using an algorithm based on new Multi-step Dynamic Binding Model with Complex Allostery; (●) free testosterone concentrations derived using the Vermeulen model (23) as implemented by Mazer (24). Solid lines are lines of best linear fit. Regression lines fit new Multi-step Dynamic Binding Model with Complex Allostery calculation (slope=1.01±0.01, regression line fitting the squares), and the Vermeulen model (slope 0.77±0.02, lower line fitting the dots). Magenta dashed line is the line of prefect correlation. FIG. 4B depicts Bland Altman plots of the relative frequency distribution of % difference of calculated and measured free testosterone using either the Vermeulen equation (squares) or the new algorithm based on the new Multi-step Dynamic Binding Model with Complex Allostery (black dots) The relative deviations from the measured value are distributed around 0 for new Multi-step Dynamic Binding Model with Complex Allostery model and are different from zero for the Vermeulen model. FIGS. 4C-4D demonstrate a Comparison of the Free Testosterone Concentrations Derived Using the Vermeulen Equation or the New Algorithm Based on the new Multi-step Dynamic Binding Model with Complex Allostery with those measured using the equilibrium dialysis in samples from a randomized testosterone trial in men with ED. FIG. 4C depicts a graph of a comparison of the free testosterone concentration calculated by the Vermeulen equation and the new algorithm based on the new Multi-step Dynamic Binding Model with Complex Allostery to that measured by equilibrium dialysis in samples from a randomized testosterone trial in men. (squares) free testosterone concentrations derived using an algorithm based on new Multi-step Dynamic Binding Model with Complex Allostery; (circles) free testosterone concentrations derived using the Vermeulen model (23) as implemented by Mazer (24). Black regression line fits new Multi-step Dynamic Binding Model with Complex Allostery model calculation (slope=1.01±0.01 is shown) FIG. 4D depicts Bland Altman plots of the relative frequency of % difference of calculated and measured free testosterone using either the Vermeulen equation or the new algorithm based on the new Multi-step Dynamic Binding Model with Complex Allostery. The relative deviations from the measured value are distributed around 0 for the new Multi-step Dynamic Binding Model with Complex Allostery model and are different from zero for the Vermeulen model.

FIG. 6 depicts schematic representations of the various models tested in this study to examine SHBG:T interaction. Model A. Vermeulen's model, homogenous interaction of testosterone molecule with equal affinity for each monomer in SHBG dimer (Kd=1 nM); Model B. monomers within the SHBG dimer exhibit distinct affinity constants with $Kd_1$=1 nM and $Kd_2$ allowed to vary for data fits; Model C. Inter-subunit allostery with positive cooperativity for binding of two ligands such that $Kd_2$=1 nM, $Kd_1$ allowed to vary and $Kd_2 < Kd_1$; Model D. allostery with negative cooperativity for binding of two ligands such that $Kd_1$=1 nM, $Kd_2$ allowed to vary and $Kd_1 < Kd_2$; and, Model E. The new Multi-step Dynamic Binding Model with Complex Allostery which encompasses two distinct SHBG microstates in equilibrium such that the equilibria between the unliganded and mono-liganded states readjust as testosterone concentration is increased.

FIG. 8A depicts a graph demonstrating that binding isotherms display significant non-linearity. Varying concentrations of testosterone were incubated with a fixed concentration of SHBG (5, 10 or 20 nM) and bound testosterone was plotted against total testosterone concentration. The binding isotherms were generated at 5, 10 and 20 nM SHBG. Curves represent the result of the fit of data to the new Multi-step Dynamic Binding Model with Complex Allostery. FIG. 8B depicts a graph demonstrating that depletion of FT by varying SHBG concentration is best described by the new Multi-step Dynamic Binding Model with Complex Allostery. Constant concentration of testosterone (6, 12, 17 or 32 nM) was incubated with increasing SHBG concentrations, and free testosterone concentration in buffer side was plotted against SHBG concentration. The curves are the result of the fit of data to the new Multi-step Dynamic Binding Model with Complex Allostery.

DETAILED DESCRIPTION

Figure 1A:
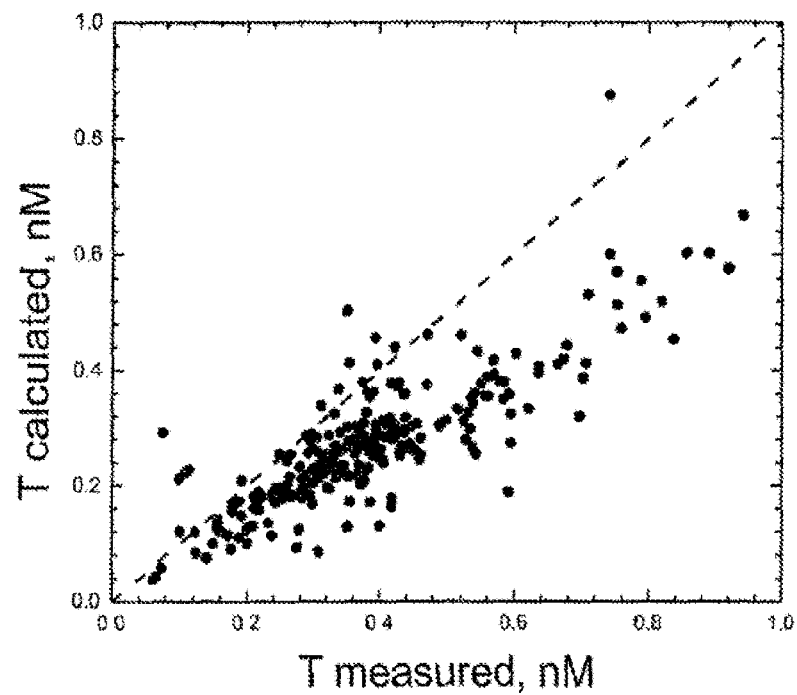
FIGS. 1A-1B demonstrate that free T values calculated using the Vermeulen/Sodergard/Mazer model—the commonly used method for determining free T concentrations—differ from those measured using equilibrium dialysis.

The current model of testosterone's binding to SHBG assumes that each SHBG dimer binds two testosterone molecules, and that each of the two binding sites on SHBG dimer has similar binding affinity. Equations to determine FT on the basis of this model were proposed by Vermeulen, Sodergard, Mazer and others. These linear equations proposed by Vermeulen, Sodergard, Mazer, and others are referred to as the prevailing equations/methods. Described herein is the characterization of testosterone's binding to SHBG using (binding isotherms varying both ligand and protein) isothermal titration calorimetry. Based on the analyses of the data presented herein, described herein are methods, assays, and systems for, e.g., the diagnosis and treatment of androgen disorders that more accurately measure biological levels of testosterone than the prevailing equations/methods.

In one aspect, described herein is an assay comprising the steps of: a) measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by fitting the data of step a) to curves using the new Multi-step Dynamic Binding Model with Complex Allostery; c) calculating the free testosterone concentration in the individual using the new Multi-step Dynamic Binding Model with Complex Allostery encompassing readjustment of a first equilibria between the microstates upon binding of a first testosterone molecule to the first monomer and an allosteric interaction between two binding sites of the SHBG dimer. In some embodiments, step b is performed according to FIG. 3. In some embodiments, step c is performed according to Example 5.

In one aspect, described herein is an assay comprising the steps of: a) measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); and c) calculating the free testosterone concentration in the individual using the New Multi-Step Dynamic Binding Model with Complex Allostery encompassing readjustment of a first equilibria between the microstates upon binding of a first testosterone molecule to the first monomer and an allosteric interaction between two binding sites of the SHBG dimer. In some embodiments, step b) is performed according to FIGS. 2, 3, 5, and 7. In some embodiments, step c) is performed according to FIG. 7 and/or Example 5.

Formulas described herein relate to a model of testosterone and SHBG binding in which two distinct interconverting microstates of an unliganded SHBG dimer having a first monomer and a second monomer. SHBG exists as one of two dimerized forms or microstates (see, e.g., FIG. 3), each of which can bind to a first testosterone molecule with a different affinity. These two microstates of SHBG can interconvert. The new Multi-step Dynamic Binding Model with Complex Allostery described herein is a model of the interaction between testosterone and SHBG which accounts for both a first equilibria between the microstates upon binding of a first testosterone molecule to the first monomer and an allosteric interaction between two binding sites of the SHBG dimer.

Without wishing to be bound by theory, testosterone is commonly known to persons of ordinary skill in the art and is shown by compound with the formula:

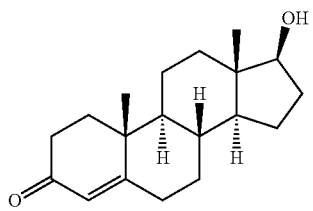

Testosterone is also known under the chemical name 17-.beta.-hydroxyandrost-4-en-3-one (or 4 androsten 17β-ol-3-one) which can be obtained in various ways: it may be isolated and purified from nature or synthetically produced by any manner. Testosterone is the major androgen in males and is controlled by luteinizing hormone (LH). LH is released from the anterior pituitary exerting the primary control on testosterone production, and acting directly on the Leydig cells in the testes, where testosterone is produced. Testosterone stimulates adult maturation of external genitalia and secondary sex organs, and the growth of beard, auxiliary and pubic hair. In addition, testosterone has anabolic effects leading to increased linear growth, nitrogen retention, and muscular development. Clinical evaluation of serum testosterone, along with serum LH, assists in evaluation of hypogonadal males. Major causes of lowered testosterone in males include hypogonadotropic hypogonadism, testicular failure, hyperprolactinemia, hypopituitarism, some types of liver and kidney diseases, and critical illness.

Testosterone levels are much lower in females compared to males. The major sources of testosterone in females are the ovaries, the adrenal glands, and the peripheral conversion of precursors, specifically the conversion of androstenedione to testosterone. In females, the normal levels of androgens may provide a substrate for estrogen production. Increased serum testosterone levels in females may be indicative of polycystic ovary syndrome and adrenal hyperplasia, among other conditions.

Testosterone binds strongly to sex hormone-binding globulin (SHBG). As used herein, "SHBG" refers to a glycoprotein that binds to sex hormones, i.e. androgens and estrogens. Sequences for SHBG of a number of species are known in the art, e.g. human SHBG (NCBI Gene ID: 6462) mRNA (NCBI Seq Ref: NM_001040) and polypeptide (NCBI Seq Ref: NP_001031).

Testosterone binds with lower affinity to albumin. As used herein, "albumin" refers to an unglycosylated protein, e.g. serum albumin. Sequences for albumin of a number of species are known in the art, e.g. human serum albumin (NCBI Gene ID: 213) mRNA (NCBI Seq Ref: NM_000477) and polypeptide (NCBI Seq Ref: NP_00468).

In some embodiments, the concentration of SHBG, testosterone, and/or albumin can be measured by an assay selected from the group consisting of an immunoassay, a binding assay, and a mass-spectrometry assay. In some embodiments, determining the level of SHBG or albumin polypeptide can comprise the use of a method selected from the group consisting of: enzyme linked immunosorbent assay; chemiluminescent immunosorbent assay; electrochemiluminescent immunosorbent assay; fluorescent immunosorbent assay; dye linked immunosorbent assay; immunoturbidimetric assay; immunonephelometric assay; dye-based photometric assay; western blot; immunoprecipitation; radioimmunological assay (RIA); radioimmunometric assay; immunofluorescence assay and mass spectroscopy. In some embodiments, determining the level of total testosterone can comprise the use of a method selected from the group consisting of: bioassays, radioligand assays, radioimmunoassay; liquid chromatography tandem mass spectroscopy; enzyme linked immunosorbent assay; chemiluminescent immunosorbent assay; electrochemiluminescent immunosorbent assay; fluorescent immunosorbent assay; and high-pressure liquid chromatography.

Total testosterone levels in a subject can be measured by ordinary methods commonly known in the art. For example, numerous assays for testosterone are known to those of skill in the art. See, e.g., Marcus and Durnford, Steroids 46:

975-86 (1985); Giraudi et al., Steroids 52: 423-4 (1988); Ooi and Donnelly, Clin. Chem. 44: 2178-82 (1988); Dorgan et al., Steroids 67: 151-8 (2002); Choi et al., Clin. Chem. 49: 322-5 (2003). Additionally, U.S. Patent Application 2008/0166697, which is incorporated herein in its entirety by reference that discloses methods to measure testosterone levels by Mass spectrometry. The measurement of total testosterone levels can be achieved by double isotope techniques and is commonly used for elucidation of difficult clinical diagnoses such as male or female pseudohermaphroditism, congenital adrenal hyperplasia and the androgen insensitivity syndrome. Commercially available kits can readily be used to measure testosterone, such as commercially available kits from Pantex, DSL, Incostar and the like. Alternatively, serum testosterone levels can be measured by isotope dilution-liquid chromatography (see Bui et al., Ann Clin Biochem 2010; 47:248-252), in the blood, urine or saliva, (commercially available testosterone assay from Salimetrics, LLC, State College, Pa.). The normal range for testosterone levels in men is broad and varies by stage of maturity and age.

Kits for measuring total testosterone levels are commercially available, e.g., from Progene (Cat No. 991547; Cincinnatti, Ohio); ZRT (Cat No. 84403; Beaverton, Oreg.); Cayman Chemicals (Cat No. 582701; Ann Arbor, Mich.); and MP Biomedicals (Cat No. 07BC-1115; Orangeburg, N.Y.), and others.

Kits for measuring SHBG levels are commercially available, e.g., from Genway Biotech Inc. (Cat No. GWB-D8B5DE; San Diego, Calif.); DRG (Cat No EIA-2996; Springfield, N.J.; and R&D Systems (Cat No. DSHBGO; Minneapolis, Minn.) and from others.

In some embodiments, e.g., albumin levels can be determined by dye-based photometric assays on an automated analyzer. Dye-based photometric assays are commercially available (e.g. the Albumin FS™ kits; DiaSys Diagnostic Systems Gmb; Holzheim, Germany or the Albumin reagent, Cat # OSR6102; Beckman Coulter; Brea, Calif.). Automated analyzers are commercially available (e.g. the AU2700 or AU5400 from Beckman Coulter; Brea, Calif.). Systems which are designed specifically for the determination of serum albumin levels are also available commercially (e.g. the Careside Analyzer™, Careside Inc., Culver City, Calif.). In some embodiments, the level of albumin levels can be determined using immunoassays, e.g. the Human Serum Albumin ELISA Kit (Cat #1190; Alpha. Diagnostic International; San Antonio, Tex.).

In some embodiments, the assays, methods and/or systems described herein comprise a step of transforming SHBG, albumin, and/or testosterone into a detectable composition and measuring the level of the detectable composition. As used herein, the term "transforming" or "transformation" refers to changing an object or a substance, e.g., biological sample, nucleic acid or protein, into another substance. The transformation can be physical, biological or chemical. Exemplary physical transformation includes, but not limited to, pre-treatment of a biological sample, e.g., from whole blood to blood serum by differential centrifugation. A biological/chemical transformation can involve at least one enzyme and/or a chemical reagent in a reaction. For example, a polypeptide can be bound by an antibody reagent.

Transformation, measurement, and/or detection of a target molecule, e.g. a testosterone molecule or SHBG polypeptide can comprise contacting a sample obtained from a subject with a reagent (e.g. a detection reagent) which is specific for the target, e.g., a SHBG-specific reagent. In some embodiments, the target-specific reagent is detectably labeled. In some embodiments, the target-specific reagent is capable of generating a detectable signal. In some embodiments, the target-specific reagent generates a detectable signal when the target molecule is present.

Methods to measure polypeptides are well known to a skilled artisan. Such methods include, e.g., ELISA (enzyme linked immunosorbent assay), western blot, immunoprecipitation, and immunofluorescence using detection reagents such as an antibody or protein binding agents. Alternatively, a peptide can be detected in a subject by introducing into a subject a labeled anti-peptide antibody and other types of detection agent. For example, the antibody can be labeled with a detectable marker whose presence and location in the subject is detected by standard imaging techniques.

For example, antibodies for SHBG are commercially available and can be used for the purposes of the invention to measure protein expression levels, e.g. anti-SHBG (Cat. No. ab31401; Abcam, Cambridge Mass.). Alternatively, since the amino acid sequences for SHBG are known and publically available at NCBI website, one of skill in the art can raise their own antibodies against these polypeptides of interest for the purpose of the invention.

In some embodiments, the measurement of, e.g., SHBG, albumin or testosterone comprises immunochemistry Immunochemistry is a family of techniques based on the use of an antibody, wherein the antibodies are used to specifically target molecules inside or on the surface of cells. The antibody typically contains a marker that will undergo a biochemical reaction, and thereby experience a change of color, upon encountering the targeted molecules. In some instances, signal amplification can be integrated into the particular protocol, wherein a secondary antibody, that includes the marker stain or marker signal, follows the application of a primary specific antibody.

In some embodiments, the assay can be a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiment, the immunoassay can be a quantitative or a semi-quantitative immunoassay.

An immunoassay is a biochemical test that measures the concentration of a substance in a biological sample, typically a fluid sample such as urine, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In one embodiment, an ELISA involving at least one antibody with specificity for the particular desired antigen (e.g., SHBG or testosterone as described herein) can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., a blood sample) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3,3',5,5'-tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce much color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

Other techniques can be used to detect the level of a polypeptide in a sample. One such technique is the dot blot, and adaptation of Western blotting (Towbin et at., Proc. Nat. Acad. Sci. 76:4350 (1979)). In a Western blot, the polypeptide or fragment thereof can be dissociated with detergents and heat, and separated on an SDS-PAGE gel before being transferred to a solid support, such as a nitrocellulose or PVDF membrane. The membrane is incubated with an antibody reagent specific for the target polypeptide or a fragment thereof. The membrane is then washed to remove unbound proteins and proteins with non-specific binding. Detectably labeled enzyme-linked secondary or detection antibodies can then be used to detect and assess the amount of polypeptide in the sample tested. The intensity of the signal from the detectable label corresponds to the amount of enzyme present, and therefore the amount of polypeptide. Levels can be quantified, for example by densitometry.

In addition, polypeptide levels can be measured using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference. Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000). In certain embodiments, a gas phase ion spectrophotometer is used.

In other embodiments, laser-desorption/ionization mass spectrometry is used to analyze the level of a protein. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes. See, e.g., U.S. Pat. No. 5,118,937 (Hillenkamp et al.), and U.S. Pat. No. 5,045,694 (Beavis & Chait). In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094. The mass spectrometers and their techniques are well known to those of skill in the art.

In some embodiments of the various aspects described herein, it is determined whether a subject has a normal level of free testosterone. In some embodiments, a normal free testosterone level can be a level greater than about 100 pg/mL (e.g. as measured using the assays of FIGS. 5A-5C and Example 5). In some embodiments, a normal free testosterone level can be a level greater than about 105 pg/mL (e.g. as measured using the assays of FIGS. 5A-5C and Example 5). In some embodiments, a normal free testosterone level can be a level greater than about 108 pg/mL (e.g. as measured using the assays of FIGS. 5A-5C and Example 5). In some embodiments, a normal free testosterone level can be a level greater than about 110 pg/mL (e.g. as measured using the assays of FIGS. 5A-5C and Example 5). In some embodiments, a normal free testosterone level can be a level greater than about 112 pg/mL (e.g. as measured using the assays of FIGS. 5A-5C and Example 5). In some embodiments, a normal free testosterone level can be a level greater than about 114 pg/mL (e.g. as measured using the assays of FIGS. 5A-5C and Example 5). In some embodiments, a normal free testosterone level can be a level greater than about 114.6 pg/mL (e.g. as measured using the assays of FIGS. 5A-5C and Example 5). In some embodiments, a normal free testosterone level can be a level greater than about 116 pg/mL (e.g. as measured using the assays of FIGS. 5A-5C and Example 5). In some embodiments, a normal free testosterone level can be a level greater than about 118 pg/mL (e.g. as measured using the assays of FIGS. 5A-5C and Example 5). In some embodiments, a normal free testosterone level can be a level greater than about 120 pg/mL (e.g. as measured using the assays of FIGS. 5A-5C and Example 5). In some embodiments, a normal free testosterone level can be a level greater than about 122 pg/mL (e.g. as measured using the assays of FIGS. 5A-5C and Example 5).

In some embodiments of the various aspects described herein, it is determined whether a subject has a free testosterone level within the healthy target range of free testosterone. In some embodiments, the target range of free testosterone can be a level from about 120 pg/mL to about 375 pg/mL (e.g. as measured using the assays of FIGS. 5A-5C and Example 5). In some embodiments, the target range of free testosterone can be a level from about 140 pg/mL to about 350 pg/mL (e.g. as measured using the assays of FIGS. 5A-5C and Example 5). In some embodiments, the target range of free testosterone can be a level from about 150 pg/mL to about 340 pg/mL (e.g. as measured using the assays of FIGS. 5A-5C and Example 5). In some embodiments, the target range of free testosterone can be a level from about 160 pg/mL to about 320 pg/mL (e.g. as measured using the assays of FIGS. 5A-5C and Example 5). In some embodiments, the target range of free testosterone can be a level from about 164 pg/mL to about 314 pg/mL (e.g. as measured using the assays of FIGS. 5A-5C and Example 5).

In one aspect, described herein is a method for treating an individual suspected of having an androgen disorder, the method comprising: a) prompting administering a pharmaceutically effective amount of testosterone to an individual who has had a free testosterone level determined by measuring a) a total SHBG concentration, b) a total testosterone concentration, and c) a total albumin concentration in a biological sample from the individual suspected of having an androgen disorder; b) receiving data comprising measuring i) a total SHBG concentration, ii) a total testosterone concentration, and iii) a total albumin concentration in a biological sample obtained from an individual, to determine free testosterone concentration from the individual; c) at least two distinct interconverting microstates of an unliganded SHBG dimer having a first monomer and a second monomer by fitting the data of step a) to curves using the new Multi-step Dynamic Binding Model with Complex Allostery; d) and calculating the free testosterone concentration in the individual using the new Multi-step Dynamic Binding Model with Complex Allostery encompassing readjustment of a first equilibria between the microstates upon binding of a first testosterone molecule to the first monomer and an allosteric interaction between two binding sites of the SHBG dimer and; e) administering to an individual having a free testosterone concentration below 114.6 pg/mL and f) not administering to an individual having a free testosterone concentration above 114.6 pg/mL. In some embodiments, step c) is performed according to FIG. 3. In some embodiments, step d) is performed according to Example 5. In some embodiments, the method can further comprise the step of classifying the individual into categories based on additional clinical symptoms.

In one aspect, described herein is a method for treating an individual suspected of having an androgen disorder comprising: a) administering a pharmaceutically effective amount of testosterone to an individual who has had a free testosterone level determined by measuring i) a total SHBG concentration, ii) a total testosterone concentration, and iii) a total albumin concentration in a biological sample from the individual suspected of having an androgen disorder; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using an the New Multi-step Dynamic Binding Model with Complex Allostery encompassing readjustment of a first equilibria between the microstates upon binding of a first testosterone molecule to the first monomer and an allosteric interaction between two binding sites of the SHBG dimer; d) administering a pharmaceutically effective amount of testosterone to an individual having a free testosterone concentration below the lower limit of a normal free testosterone concentration from a healthy individual (e.g., in one embodiment, below 114.6 pg/ml); and e) not administering a pharmaceutically effective amount of testosterone to an individual having a free testosterone concentration above the lower limit of the normal free testosterone concentration from a healthy individual (e.g., in one embodiment, above 114.6 pg/ml, the lower limit of this assay). One of skill in the art understands that the lower limit of a normal free testosterone concentration will vary according to assay used to detect total testosterone, SHBG, and albumin and will vary in a different patient populations. Thus the lower limit used for implementation should correspond to the lower limit obtained in a healthy individual using the same assays as used on the biological sample from the test individual, and the lower limit used should be the lower limit from a healthy individual of the same age and type of the test individual. Thus, the computer systems and media will result in sending a signal for administering to an individual having a free testosterone concentration below the lower limit of the normal in that assay, or sending a signal for not administering to an individual having a free testosterone concentration above the lower limit of that assay. In some embodiments, step c) is performed according to FIGS. 2, 3, 5, and 7. In some embodiments, step d) is performed according to FIG. 7 or Example 5.

As used herein, "androgen disorder" refers to a condition arising from and/or characterized by abnormal levels of one or more androgens, e.g. a condition arising from and/or characterized by abnormally low levels of testosterone. In some embodiments, the androgen disorder is selected from the group consisting of a testosterone deficiency, an androgen deficiency, a hyperandrogenic disorder, and a hypogonadism disorder. In some embodiments, the androgen disorder is a hyperandrogenic disorder selected form the group consisting of a polycystic ovary syndrome, an acne disorder, a hirsutism disorder, an androgen-expressing tumor, and an androgenic alopecia disorder.

In some embodiments, the methods described herein relate to treating a subject having, suspected as having, or diagnosed as having an androgen disorder, e.g. with low testosterone levels. Subjects having low testosterone can be identified by a physician using the methods described herein, alternatively, combined with current methods of diagnosing low testosterone. Symptoms and/or complications of low testosterone which characterize these conditions and aid in diagnosis are well known in the art and include but are not limited to, decreased sexual desire (e.g., decreased libido), erectile dysfunction (ED), decreased concentration, loss of muscle mass, breast enlargement, fatigue, low mood, and the like.

In one aspect, described herein is a method for determining a need for adjustment of a dose of testosterone administered to an individual comprising: a) determining the concentration of free testosterone in an individual receiving testosterone therapy at a first dose, wherein the concentration of free testosterone is determined by; b) receiving data comprising measuring i) a total SHBG concentration, ii) a total testosterone concentration, and iii) a total albumin concentration in a biological sample obtained from an individual, to determine free testosterone concentration from the individual; c) attributing at least two distinct interconverting microstates of an unliganded SHBG dimer having a first monomer and a second monomer by fitting the data of step a) to curves using the new Multi-step Dynamic Binding Model with Complex Allostery; d) and calculating the free testosterone concentration in the individual using the new Multi-step Dynamic Binding Model with Complex Allostery encompassing readjustment of a first equilibria between the microstates upon binding of a first testosterone molecule to the first monomer and an allosteric interaction between two binding sites of the SHBG dimer and; e) providing a second dose of testosterone that is higher than the first dose when the free testosterone concentration is below 164 pg/mL; and f) providing a second dose of testosterone that is lower than the first dose when the free testosterone concentration is above 314 pg/mL. In some embodiments, step c) is performed according to FIG. 3. In some embodiments, step d) is performed according to Example 5. In some embodiments, the method can further comprise the step of classifying the individual into categories based on additional clinical symptoms.

In one aspect, described herein is a method for determining a need for adjustment of a dose of testosterone administered to an individual comprising a) determining the concentration of free testosterone in an individual receiving testosterone therapy at a first dose, wherein the concentration of free testosterone is determined by b) measuring i) a total SHBG concentration, ii) a total testosterone concentration, and iii) a total albumin concentration in a biological sample obtained from an individual, to determine free testosterone concentration from the individual; c) attributing at least two distinct interconverting microstates of an unliganded SHBG dimer having a first monomer and a second monomer by applying the New Multi-Step Dynamic Binding Model with Complex Allostery to the data of steps a) and b); d) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer; e) providing a second dose of testosterone that is higher than the first dose when the free testosterone concentration is below the lower end of the target therapeutic range (e.g. 164 pg/ml); and f) providing a second dose of testosterone that is lower than the first dose when the free testosterone concentration is above the upper end of the target therapeutic range (314 pg/ml). In another embodiment, the target therapeutic range could vary with the age of the patient, co-morbid conditions, and the types of assays used for measuring total testosterone, SHBG and albumin, in which case sending the signal for providing a second dose of testosterone that is higher than the first dose when the free testosterone concentration is below the lower end of the target therapeutic range for that age, co-morbid conditions and assay. In some embodiments, step c) is performed according to FIGS. 2, 3, 5, and 7. In some embodiments, step d) is performed according to FIG. 7 or Example 5.

In some embodiments, the assay further comprises the step of determining the concentration of at least one non-testosterone steroid. As used herein, the term "steroid" refers to a chemical substance comprising three cyclohexane rings and a cyclopentane ring. In some embodiments, the non-testosterone steroid is selected from the group consisting of an estradiol steroid, an estrone steroid, and a dihydrotestosterone steroid.

In some embodiments, the individual of the methods and systems described herein is an individual who has or has been diagnosed with a disease selected from the group consisting of: diabetes, human immunodeficiency virus (HIV), hepatitis B, hepatitis C, androgen insensitivity, acromegaly, anorexia, muscular dystrophy, liver disease, cancer, cachexia, malnutrition, nephrotic syndrome and obesity, and other conditions in which SHBG and albumin concentrations are altered.

In some embodiments, the individual of the methods and systems described herein is a male. In some embodiments, the individual of the methods and systems described herein is a male over the age of 35, e.g, over the age of 40, over the age of 45, over the age of 50, over the age of 55, or over the age of 60.

As used herein, "testosterone therapy" refers to the administration of testosterone or an analogue thereof, e.g. to treating an androgen disorder. The term "or analogue thereof" includes any useful metabolite or precursor of testosterone, for example the metabolite dihydrotestosterone. In some embodiments, a testosterone analogue can be, e.g., a testosterone ester such as testosterone cypionate, enanthate or propionate or a combination thereof, prodrug or fatty acid ester of testosterone; a fatty acid ester of testosterone of long chain (i.e., 14 or more carbons); methyltestosterone (in which the methyl group is covalently bonded to the testosterone nucleus as the C17 position to inhibit hepatic metabolism); a testosterone alkyl ester; an undecanoate acid ester of testosterone; testosterone undecanote; or a composition as disclosed, e.g, in US Patent Application US2011/0251167 which is incorporated herein in its entirety by reference.

Numerous compositions are available for testosterone therapy, e.g. testosterone patches or injections; intramuscular injections, implants, oral tablets of alkylated T (e.g., methyltestosterone), transdermal formulations such as the topical gels and solutions, or topical patches, and the like.

The formulation of the testosterone or testosterone derivatives and analogues or salts thereof should provide a dose of testosterone adequate to maintain the male subject's serum total testosterone level within the normal male range (approximately 300 to 1000 ng/dL range), based on measures of serum total testosterone. The pharmaceutically effective amount of the testosterone or testosterone derivatives and analogues or salts thereof present in the compositions as disclosed herein depends on the patient's starting serum total testosterone and the mode of administration. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of active ingredient for the symptomatic adjustment of the dosage to the subject to be treated. An effective amount of the drug is ordinarily supplied at a dosage level of from about 0.0002 mg/kg to about 50 mg/kg of body weight per day. The range is more particularly from about 0.001 to 7 mg/kg of body weight per day. In particular, testosterone and testosterone derivatives and analogues or salts thereof delivered by intramuscular injections may be provided in injections of 50 to 750 mg every one to 4 weeks. In one embodiment, testosterone and testosterone derivatives and analogues or salts thereof are provided by intramuscular injections of 100 to 500 mg every 1 to 4 weeks. In one class of this embodiment, testosterone and testosterone derivatives and analogues or salts thereof are provided by intramuscular injections of 50 to 250 mg every 1 to 4 weeks.

Testosterone and testosterone derivatives and analogues or salts thereof may be provided in gel or cream forms in doses of 20 to 200 mg per day. In one embodiment, testosterone and testosterone derivatives and analogues or salts thereof are provided in a gel at doses of 50 to 100 mg/day, particularly 50 mg/day, 75 mg/day and 100 mg/day.

Transdermal patches can used to deliver testosterone and testosterone derivatives and analogues or salts thereof of 1 to 10 mg per day, particularly, 4 to 6 mg/day.

Testosterone, testosterone derivatives and analogues or salts thereof may also be provided by means of a buccal gel at a dose of 10 mg/day to 100 mg/day. In one embodiment, the dose of testosterone or testosterone derivatives and analogues or salts thereof is a buccal gel is 40 to 80 mg/day.

In one class of this embodiment, the dose of testosterone or testosterone derivatives and analogues or salts thereof in a buccal gel is 60 mg/day.

In some embodiments, the methods, systems, and assays described herein can comprise the use of a new target range of free testosterone for ongoing testosterone therapy. The new target range arises from the more accurate methods for detecting free testosterone as described herein. Concentration valuses of free testosterone indicative of low testosterone in an individual are also described herein.

Commerical testosterone therapies are known in the art, e.g. topical testosterone formulations (e.g., ANDROGEN™, AXIRON™, FIRST-TESTOSTERONE™, FIRST-TESTOSTERONE MC™, FORTESTA™, and TESTIM™); transdermal patch formulations (e.g., ANDRODERM™); and buccal testosterone formulations (e.g., STRIANT™).

In some embodiments of the various aspects described herein, a subject's dose of testosterone therapy is adjusted until their free testosterone levels are normal. In some embodiments, a normal free testosterone level can be a level greater than about 100 pg/mL (e.g. as measured using the assays of FIGS. 5A-5C and Example 5). In some embodiments, a normal free testosterone level can be a level greater than about 105 pg/mL (e.g. as measured using the assays of FIGS. 5A-5C and Example 5). In some embodiments, a normal free testosterone level can be a level greater than about 110 pg/mL (e.g. as measured using the assays of FIGS. 5A-5C and Example 5). In some embodiments, a normal free testosterone level can be a level greater than about 114 pg/mL (e.g. as measured using the assays of FIGS. 5A-5C and Example 5). In some embodiments, a normal free testosterone level can be a level greater than about 114.6 pg/mL (e.g. as measured using the assays of FIGS. 5A-5C and Example 5).

In some embodiments of the various aspects described herein, a subject's dose of testosterone therapy is adjusted until their free testosterone levels are in the target range of free testosterone. In some embodiments, the target range of free testosterone can be a level from about 120 pg/mL to about 375 pg/mL (e.g. as measured using the assays of FIGS. 5A-5C and Example 5). In some embodiments, the target range of free testosterone can be a level from about 140 pg/mL to about 350 pg/mL (e.g. as measured using the assays of FIGS. 5A-5C and Example 5). In some embodiments, the target range of free testosterone can be a level from about 150 pg/mL to about 340 pg/mL (e.g. as measured using the assays of FIGS. 5A-5C and Example 5). In some embodiments, the target range of free testosterone can be a level from about 160 pg/mL to about 320 pg/mL (e.g. as measured using the assays of FIGS. 5A-5C and Example 5). In some embodiments, the target range of free testosterone can be a level from about 164 pg/mL to about 314 pg/mL (e.g. as measured using the assays of FIGS. 5A-5C and Example 5).

The term "sample" or "test sample" as used herein denotes a sample taken or isolated from a biological organism, e.g., a blood or plasma sample from a subject. Exemplary biological samples include, but are not limited to, a biofluid sample; serum; plasma; urine; saliva; and/or tissue sample etc. The term also includes a mixture of the above-mentioned samples. The term "test sample" also includes untreated or pretreated (or pre-processed) biological samples. In some embodiments, a test sample can comprise cells from subject. In some embodiments, the test sample can be a blood sample. In some embodiments, the test sample can be a plasma sample.

The test sample can be obtained by removing a sample from a subject, but can also be accomplished by using previously sample (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments, the methods, assays, and systems described herein can further comprise a step of obtaining a test sample from a subject. In some embodiments, the subject can be a human subject. In some embodiments, the subject can be a subject in need of treatment for (e.g. having or diagnosed as having) an androgen disorder.

In one aspect, described herein is a computer implemented method for an assay, comprising:
on a device having one or more processors and a memory storing one or more programs for execution by the one or more processors, the one or more programs including instructions for: a) receiving data from measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer; and c) calculating the free testosterone concentration in the individual using the New Multi-Step Dynamic Binding Model with Complex Allostery encompassing readjustment of a first equilibria between the microstates upon binding of a first testosterone molecule to the first monomer and an allosteric interaction between two binding sites of the SHBG dimer. In some embodiments, step b) is performed according to FIGS. 2, 3, 5, and 7. In some embodiments, step c) is performed according to FIG. 7 or Example 5. In some embodiments, the assay further comprises the step of determining the concentration of at least one non-testosterone steroid. In some embodiments, the non-testosterone steroid is selected from the group consisting of an estradiol steroid, an estrone steroid, and a dihydrotestosterone steroid. In some embodiments, the total SHBG concentration, the total testosterone concentration, and the total albumin concentration is determined using an assay selected from the group consisting of an immunoassay, a binding assay, and a mass-spectrometry assay.

In one aspect, described herein is a computer system for an assay, comprising: one or more processors; and memory to store: one or more programs, the one or more programs comprising: instructions for: a) receiving data from measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); and c) calculating the free testosterone concentration in the individual using the New Multi-Step Dynamic Binding Model with Complex Allostery encompassing readjustment of a first equilibria between the microstates upon binding of a first testosterone molecule to the first monomer and an allosteric interaction between two binding sites of the SHBG dimer. In some embodiments, step b) is performed according to FIGS. 2, 3, 5, and 7. In some embodiments, step c) is performed according to FIG. 7 or Example 5. In some embodiments, the assay further comprises the step of determining the concentration of at least one non-testosterone steroid. In some embodiments, the non-testosterone steroid is selected from the group consisting of an estradiol steroid, an estrone steroid, and a dihydrotestosterone steroid. In some embodiments, the total SHBG concentration, the total testosterone concentration, and the total albumin concentration is determined using an assay selected from the group consisting of an immunoassay, a binding assay, and a mass-spectrometry assay.

In one aspect, described herein is a non-transitory computer-readable storage medium storing one or more programs for treating an individual suspected of having an androgen disorder, the one or more programs for execution by one or more processors of a computer system, the one or more programs comprising instructions for: a) receiving data from measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); and c) calculating the free testosterone concentration in the individual using the New Multi-Step Dynamic Binding Model with Complex Allostery encompassing readjustment of a first equilibria between the microstates upon binding of a first testosterone molecule to the first monomer and an allosteric interaction between two binding sites of the SHBG dimer. In some embodiments, step b) is performed according to FIGS. 2, 3, 5, and 7. In some embodiments, step c) is performed according to FIG. 7 or Example 5. In some embodiments, the assay further comprises the step of determining the concentration of at least one non-testosterone steroid. In some embodiments, the non-testosterone steroid is selected from the group consisting of an estradiol steroid, an estrone steroid, and a dihydrotestosterone steroid. In some embodiments, the total SHBG concentration, the total testosterone concentration, and the total albumin concentration is determined using an assay selected from the group consisting of an immunoassay, a binding assay, and a mass-spectrometry assay.

In one aspect, described herein is a computer implemented method for treating an individual suspected of having an androgen disorder, comprising: on a device having one or more processors and a memory storing one or more programs for execution by the one or more processors, the one or more programs including instructions for: a) receiving data from measuring i) a total SHBG concentration, ii) a total testosterone concentration, and iii) a total albumin concentration in a biological sample obtained from an individual suspected of having an androgen disorder, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using a New Multi-step Dynamic Binding Model with Complex Allostery encompassing readjustment of a first equilibria between the microstates upon binding of a first testosterone molecule to the first monomer and an allosteric interaction between two binding sites of the SHBG dimer; d) sending a signal for administering a pharmaceutically effective amount of testosterone to an individual having a free testosterone concentration below the lower limit of a normal free testosterone concentration from a healthy individual (e.g., in one embodiment, the lower limit is 114.6 pg/ml); and e) sending a signal for not administering a pharmaceutically effective amount of testosterone to an individual having a free testosterone concentration above the lower limit of the normal free testosterone concentration from a healthy individual (e.g., in one embodiment, the lower limit is 114.6 pg/ml). One of skill in the art understands that the lower limit of a normal free testosterone concentration will vary according to assay used to detect total testosterone, SHBG, and albumin and will vary in a different patient populations. Thus the lower limit used for implementation should correspond to the lower limit obtained in a healthy individual using the same assays as used on the biological sample from the test individual, and the lower limit used should be the lower limit from a healthy individual of the same age and type of the test individual. Thus, the computer systems and media will result in sending a signal for administering to an individual having a free testosterone concentration below the lower limit of the normal in that assay, or sending a signal for not administering to an individual having a free testosterone concentration above the lower limit of that assay.

In some embodiments, step c) is performed according to FIGS. 2, 3, 5, and 7. In some embodiments, step d) is performed according to FIG. 7 or Example 5. In some embodiments, the individual is a male over the age of 35. In some embodiments, the androgen disorder is selected from the group consisting of a testosterone deficiency, an androgen deficiency, a hyperandrogenic disorder, an androgen expressing tumor, and a hypogonadism disorder. In some embodiments, the androgen disorder is a hyperandrogenic disorder selected from the group consisting of an acne disorder, a hirsutism disorder, and an androgenic alopecia disorder. In some embodiments, the individual has been diagnosed with a disease selected from the group consisting of: diabetes, human immunodeficiency virus (HIV), hepatitis B, hepatitis C, hypothyroidism or hyperthyroidism, androgen insensitivity, acromegaly, anorexia, muscular dystrophy, liver disease, cancer cachexia, malnutrition, nephrotic syndrome, and obesity, and other conditions in which SHBG or albumin concentrations are altered. In some embodiments, the method further comprises the step of classifying the individual into categories based on additional clinical symptoms.

In one aspect, described herein is a computer system for treating an individual suspected of having an androgen disorder, comprising: one or more processors; and memory to store: one or more programs, the one or more programs comprising: instructions for: a) receiving data from measuring i) a total SHBG concentration, ii) a total testosterone concentration, and iii) a total albumin concentration in a biological sample obtained from an individual suspected of having an androgen disorder, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer; d) sending a signal for administering to a pharmaceutically effective amount of testosterone to an individual having a free testosterone concentration (based on a, b, c, d above or obtained otherwise) below the lower limit of a normal free testosterone concentration from a healthy individual (e.g., in one embodiment, the lower limit is 114.6 pg/ml); and e) sending a signal for not administering a pharmaceutically effective amount of testosterone to an individual having a free testosterone concentration (based on a, b, c, d above or obtained otherwise) above the lower limit of the normal free testosterone concentration from a healthy individual (e.g., in one embodiment, the lower limit is 114.6 pg/ml). One of skill in the art understands that the lower limit of a normal free testosterone concentration will vary according to assay used to detect total testosterone, SHBG, and albumin and will vary in a different patient populations. Thus the lower limit used for implementation should correspond to the lower limit obtained in a healthy individual using the same assays as used on the biological sample from the test individual, and the lower limit used should be the lower limit from a healthy individual of the same age and type of the test individual. Thus, the computer systems and media will result in sending a signal for administering to an individual having a free testosterone concentration below the lower limit of the normal in that assay, or sending a signal for not administering to an individual having a free testosterone concentration above the lower limit of that assay.

In some embodiments, step c) is performed according to FIGS. 2, 3, 5, and 7. In some embodiments, step d) is performed according to FIG. 7 or Example 5. In some embodiments, the individual is a male over the age of 35. In some embodiments, the androgen disorder is selected from the group consisting of a testosterone deficiency, an androgen deficiency, a hyperandrogenic disorder, an androgen expressing tumor, and a hypogonadism disorder. In some embodiments, the androgen disorder is a hyperandrogenic disorder selected from the group consisting of an acne disorder, a hirsutism disorder, and an androgenic alopecia disorder. In some embodiments, the individual has been diagnosed with a disease selected from the group consisting of: diabetes, human immunodeficiency virus (HIV), hepatitis B, hepatitis C, hypothyroidism or hyperthyroidism, androgen insensitivity, acromegaly, anorexia, muscular dystrophy, liver disease, cancer cachexia, malnutrition, nephrotic syndrome, and obesity, and other conditions in which SHBG or albumin concentrations are altered. In some embodiments, the system further comprises the step of classifying the individual into categories based on additional clinical symptoms.

In one aspect, described herein is a non-transitory computer-readable storage medium storing one or more programs for treating an individual suspected of having an androgen disorder, the one or more programs for execution by one or more processors of a computer system, the one or more programs comprising instructions for a) receiving data from measuring i) a total SHBG concentration, ii) a total testosterone concentration, and iii) a total albumin concentration in a biological sample obtained from an individual suspected of having an androgen disorder, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using New Multi-step Dynamic Binding Model with Complex Allostery encompassing readjustment of a first equilibria between the microstates upon binding of a first testosterone molecule to the first monomer and an allosteric interaction between two binding sites of the SHBG dimer; d) sending a signal for administering a pharmaceutically effective amount of testosterone to an individual having a free testosterone concentration below the lower limit of a normal free testosterone concentration from a healthy individual (e.g., in one embodiment, below 114.6 pg/ml); and e) sending a signal for not administering a pharmaceutically effective amount of testosterone to an individual having a free testosterone concentration above the lower limit of the normal free testosterone concentration from a healthy individual (e.g., in one embodiment, above 114.6 pg/ml, the lower limit of this assay). One of skill in the art understands that the lower limit of a normal free testosterone concentration will vary according to assay used to detect total testosterone, SHBG, and albumin and will vary in a different patient populations. Thus the lower limit used for implementation should correspond to the lower limit obtained in a healthy individual using the same assays as used on the biological sample from the test individual, and the lower limit used should be the lower limit from a healthy individual of the same age and type of the test individual. Thus, the computer systems and media will result in sending a signal for administering to an individual having a free testosterone concentration below the lower limit of the normal in that assay, or sending a signal for not administering to an individual having a free testosterone concentration above the lower limit of that assay.

In some embodiments, step c) is performed according to FIGS. 2, 3, 5, and 7. In some embodiments, step d) is performed according to FIG. 7 or Example 5. In some embodiments, the individual is a male over the age of 35. In some embodiments, the androgen disorder is selected from the group consisting of a testosterone deficiency, an androgen deficiency, a hyperandrogenic disorder, an androgen expressing tumor, and a hypogonadism disorder. In some embodiments, the androgen disorder is a hyperandrogenic disorder selected from the group consisting of an acne disorder, a hirsutism disorder, and an androgenic alopecia disorder. In some embodiments, the individual has been diagnosed with a disease selected from the group consisting of: diabetes, human immunodeficiency virus (HIV), hepatitis B, hepatitis C, hypothyroidism or hyperthyroidism, androgen insensitivity, acromegaly, anorexia, muscular dystrophy, liver disease, cancer cachexia, malnutrition, nephrotic syndrome, and obesity, and other conditions in which SHBG or albumin concentrations are altered. In some embodiments, the medium further comprises the step of classifying the individual into categories based on additional clinical symptoms.

In one aspect, described herein is a computer implemented method for determining a need for adjustment of a dose of testosterone administered to an individual with hypogonadism, androgen deficiency syndrome, or any other condition for which testosterone therapy is indicated, comprising: on a device having one or more processors and a memory storing one or more programs for execution by the one or more processors, the one or more programs including instructions for: a) receiving data from determining the concentration of free testosterone in an individual receiving testosterone therapy at a first dose, wherein the concentration of free testosterone is determined by measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer and; d) sending a signal for providing a second (adjusted) dose of testosterone that is higher than the first dose when the free testosterone concentration is below the lower end of the target therapeutic (e.g. 164 pg/ml); and e) sending a signal for providing a second (adjusted) dose of testosterone that is lower than the first dose when the free testosterone concentration is above the upper end of the target therapeutic range (e.g. 314 pg/ml). One of skill in the art understands that the target therapeutic range could vary depending on the age of the patient, the population, and the types of total testosterone, SHBG and albumin assays, in which case sending a signal sending a signal for providing a second (adjusted) dose of testosterone that is higher than the first dose when the free testosterone concentration is below the target therapeutic range for that age, population, and assay of total testosterone, SHBG and albumin, or sending a signal for providing a second (adjusted) dose of testosterone that is lower than the first dose when the free testosterone concentration is above the target therapeutic range. Examples of suitable target ranges are described herein.

In some embodiments, the method can further comprise the step of receiving data of the first dose of testosterone administered to the individual. In some embodiments, step c) is performed according to FIGS. 2, 3, 5, and 7. In some embodiments, step d) is performed according to FIG. 7 or Example 5. In some embodiments, the individual is a male over the age of 35. In some embodiments, the androgen disorder is selected from the group consisting of a testosterone deficiency, an androgen deficiency, a hyperandrogenic disorder, an androgen expressing tumor, and a hypogonadism disorder. In some embodiments, the androgen disorder is a hyperandrogenic disorder selected from the group consisting of an acne disorder, a hirsutism disorder, and an androgenic alopecia disorder. In some embodiments, the individual has been diagnosed with a disease selected from the group consisting of: diabetes, human immunodeficiency virus (HIV), hepatitis B, hepatitis C, hypothyroidism or hyperthyroidism, androgen insensitivity, acromegaly, anorexia, muscular dystrophy, liver disease, cancer cachexia, malnutrition, nephrotic syndrome, and obesity, and other conditions in which SHBG or albumin concentrations are altered. In some embodiments, the method further comprises the step of classifying the individual into categories based on additional clinical symptoms.

In one aspect, described herein is a computer system for determining a need for adjustment of a dose of testosterone administered to an individual, comprising: one or more processors; and memory to store: one or more programs, the one or more programs comprising: instructions for: a) receiving data from determining the concentration of free testosterone in an individual receiving testosterone therapy at a first dose, wherein the concentration of free testosterone is determined by measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer; d) sending a signal for providing a second dose of testosterone that is higher than the first dose when the free testosterone concentration is below the lower end of the target therapeutic range (e.g. 164 pg/ml); and e) sending a signal for providing a second dose of testosterone that is lower than the first dose when the free testosterone concentration is above the upper end of the target therapeutic range (e.g. 314 pg/ml).

In some embodiments, step c) is performed according to FIGS. 2, 3, 5, and 7. In some embodiments, step d) is performed according to FIG. 7 or Example 5. In some embodiments, the individual is a male over the age of 35. In some embodiments, the androgen disorder is selected from the group consisting of a testosterone deficiency, an androgen deficiency, a hyperandrogenic disorder, an androgen expressing tumor, and a hypogonadism disorder. In some embodiments, the androgen disorder is a hyperandrogenic disorder selected from the group consisting of an acne disorder, a hirsutism disorder, and an androgenic alopecia disorder. In some embodiments, the individual has been diagnosed with a disease selected from the group consisting of: diabetes, human immunodeficiency virus (HIV), hepatitis B, hepatitis C, hypothyroidism or hyperthyroidism, androgen insensitivity, acromegaly, anorexia, muscular dystrophy, liver disease, cancer cachexia, malnutrition, nephrotic syndrome, and obesity, and other conditions in which SHBG or albumin concentrations are altered. In some embodiments, the method further comprises the step of classifying the individual into categories based on additional clinical symptoms.

In one aspect, described herein is a non-transitory computer-readable storage medium storing one or more programs for determining a need for adjustment of a dose of testosterone administered to an individual, the one or more programs for execution by one or more processors of a computer system, the one or more programs comprising instructions for: a) receiving data from determining the concentration of free testosterone in an individual receiving testosterone therapy at a first dose, wherein the concentration of free testosterone is determined by measuring i) a total SHBG concentration, ii) a total testosterone concentration, and iii) a total albumin concentration in a biological sample obtained from an individual, to determine free testosterone concentration from the individual; b) attributing at least two distinct interconverting microstates of an unliganded SHBG dimer having a first monomer and a second monomer by applying the New Multi-Step Dynamic Binding Model with Complex Allostery to the data of step a); c) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer; d) sending a signal for providing a second dose of testosterone that is higher than the first dose when the free testosterone concentration is below the lower end of the target therapeutic range (e.g. 164 pg/ml); and e) sending a signal for providing a second dose of testosterone that is lower than the first dose when the free testosterone concentration is above the upper end of the target therapeutic range (e.g. 314 pg/ml). In specification: In another embodiment, the target therapeutic range could vary with the age of the patient, co-morbid conditions, and the types of assays used for measuring total testosterone, SHBG and albumin, in which case sending the signal for providing a second dose of testosterone that is higher than the first dose when the free testosterone concentration is below the lower end of the target therapeutic range for that age, co-morbid conditions and assay.

In some embodiments, step c) is performed according to FIGS. 2, 3, 5, and 7. In some embodiments, step d) is performed according to FIG. 7 or Example 5. In some embodiments, the individual is a male over the age of 35. In some embodiments, the androgen disorder is selected from the group consisting of a testosterone deficiency, an androgen deficiency, a hyperandrogenic disorder, an androgen expressing tumor, and a hypogonadism disorder. In some embodiments, the androgen disorder is a hyperandrogenic disorder selected from the group consisting of an acne disorder, a hirsutism disorder, and an androgenic alopecia disorder. In some embodiments, the individual has been diagnosed with a disease selected from the group consisting of: diabetes, human immunodeficiency virus (HIV), hepatitis B, hepatitis C, hypothyroidism or hyperthyroidism, androgen insensitivity, acromegaly, anorexia, muscular dystrophy, liver disease, cancer cachexia, malnutrition, nephrotic syndrome, and obesity, and other conditions in which SHBG or albumin concentrations are altered. In some embodiments, the method further comprises the step of classifying the individual into categories based on additional clinical symptoms.

Figure 12:
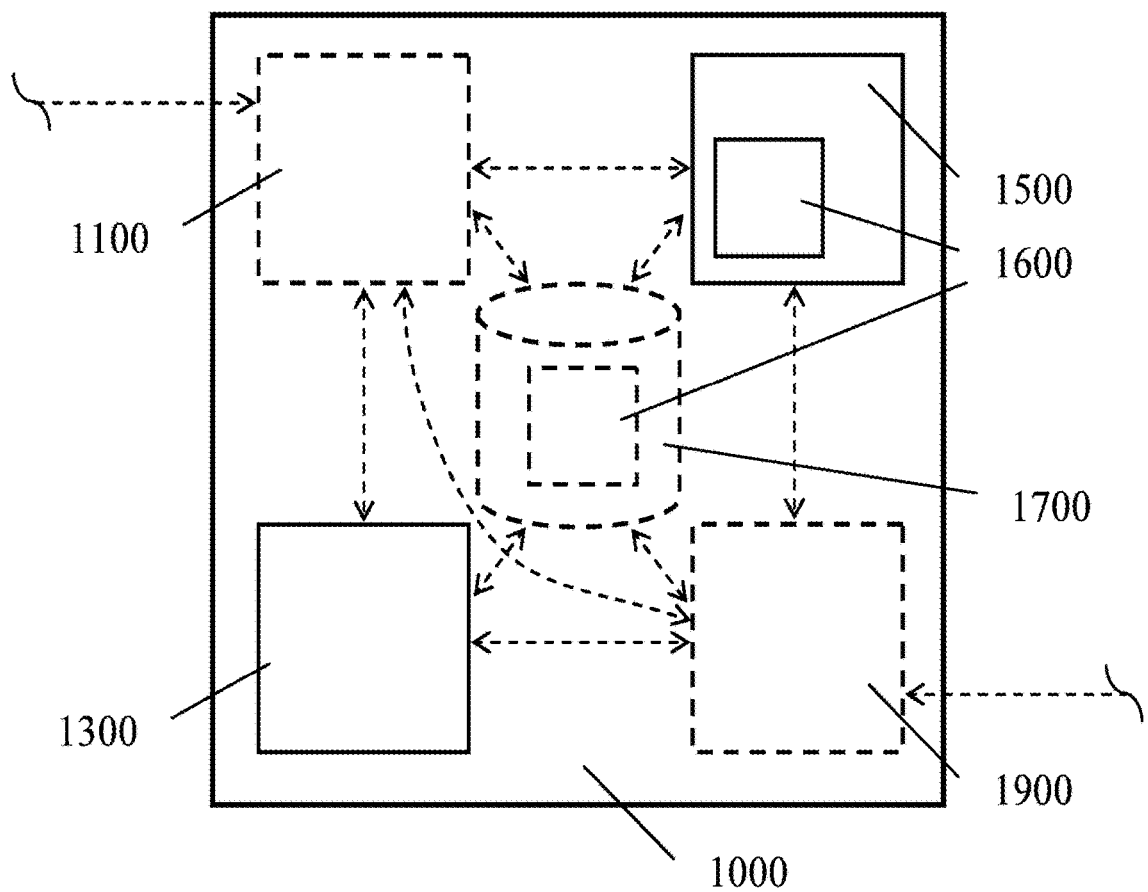
FIG. 12 depicts a device or a computer system 1000 comprising one or more processors 1300 and a memory 1500 storing one or more programs 1600 for execution by the one or more processors 1300.

FIG. 12 depicts a device or a computer system 1000 comprising one or more processors 1300 and a memory 1500 storing one or more programs 1600 for execution by the one or more processors 1300. In some embodiments, the device or computer system 1000 can further comprise a non-transitory computer-readable storage medium 1700 storing the one or more programs 1600 for execution by the one or more processors 1300 of the device or computer system 1000.

In some embodiments, the device or computer system 1000 can further comprise one or more input devices 1100, which can be configured to send or receive information to or from any one from the group consisting of: an external device (not shown), the one or more processors 1300, the memory 1500, the non-transitory computer-readable storage medium 1700, and one or more output devices 1900.

In some embodiments, the device or computer system 1000 can further comprise one or more output devices 1900, which can be configured to send or receive information to or from any one from the group consisting of: an external device (not shown), the one or more processors 1300, the memory 1500, and the non-transitory computer-readable storage medium 1700.

Each of the above identified modules or programs corresponds to a set of instructions for performing a function described above. These modules and programs (i.e., sets of instructions) need not be implemented as separate software programs, procedures or modules, and thus various subsets of these modules may be combined or otherwise re-arranged in various embodiments. In some embodiments, memory may store a subset of the modules and data structures identified above. Furthermore, memory may store additional modules and data structures not described above.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described herein can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer-readable medium; or a combination thereof.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or"

is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used herein differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be appreciated that the methodologies disclosed in this specification are capable of being stored on an article of manufacture to facilitate transporting and transferring such methodologies to computing devices. The term article of manufacture, as used herein, is intended to encompass a computer program accessible from any computer-readable device or storage media.

In some embodiments of any of the aspects described herein, instead of steps a-c, the data received is a previously calculated concentration of free testosterone.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The term "effective amount" as used herein refers to the amount of, e.g. testosterone needed to alleviate at least one or more symptom of the disease or disorder, and relates to a sufficient amount of pharmacological composition to provide the desired effect. The term "therapeutically effective amount" therefore refers to an amount of, e.g., testosterone that is sufficient to provide a particular anti-low testosterone effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of testosterone, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for free testosterone as described herein, among others. The dosage can be determined by a physician and adjusted, as necessary, to suit observed effects of the treatment.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" or "individual" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of androgen disorders. A subject can be male or female.

A subject can be one who has been previously diagnosed with or identified as suffering from or having a condition in need of treatment (e.g. an androgen disorder) or one or more complications related to such a condition, and optionally, have already undergone treatment for an androgen disorder or the one or more complications related to an androgen disorder. Alternatively, a subject can also be one who has not been previously diagnosed as having an androgen disorder or one or more complications related to an androgen disorder. For example, a subject can be one who exhibits one or more risk factors for an androgen disorder or one or more complications related to an androgen disorder or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. an androgen disorder. The term "treating" includes reducing or alleviating at least one adverse effect or symptom of a condition, disease or disorder associated with an androgen disorder. Treatment is generally "effective" if one or more symptoms or clinical markers are reduced. Alternatively, treatment is "effective" if the progression of a disease is reduced. That is, "treatment" includes not just the improvement of symptoms or markers, but also a slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000); Fundamentals of RIA and Other Ligand Assays by Jeffrey Travis, 1979, Scientific Newsletters; Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A computer implemented method for an assay, comprising:
   on a device having one or more processors and a memory storing one or more programs for execution by the one or more processors, the one or more programs including instructions for:
   a) receiving data from measuring i) a total SHBG concentration, ii) a total testosterone concentration, and iii) a total albumin concentration in a biological sample obtained from an individual, to determine free testosterone concentration from the individual;
   b) attributing at least two distinct interconverting microstates of an unliganded SHBG dimer having a first monomer and a second monomer; and
   c) calculating the free testosterone concentration in the individual using the New Multi-Step Dynamic Binding Model with Complex Allostery encompassing readjustment of a first equilibria between the microstates upon binding of a first testosterone molecule to the first monomer and an allosteric interaction between two binding sites of the SHBG dimer.
2. The computer implemented method of paragraph 1, wherein step b) is performed according to FIGS. 2, 3, 5, and 7.
3. The computer implemented method of paragraph 1, wherein step c) is performed according to FIG. 7 or Example 5.
4. The computer implemented method of paragraph 1, wherein the assay further comprises the step of determining the concentration of at least one non-testosterone steroid.
5. The computer implemented method of paragraph 4, wherein the non-testosterone steroid is selected from the group consisting of an estradiol steroid, an estrone steroid, and a dihydrotestosterone steroid.
6. The computer implemented method of paragraph 1, wherein the total SHBG concentration, the total testosterone concentration, and the total albumin concentration is determined using an assay selected from the group consisting of an immunoassay, a binding assay, and a mass-spectrometry assay.
7. A computer system for an assay, comprising:
one or more processors; and
memory to store:
one or more programs, the one or more programs comprising:
instructions for:
a) receiving data from measuring i) a total SHBG concentration, ii) a total testosterone concentration, and iii) a total albumin concentration in a biological sample obtained from an individual, to determine free testosterone concentration from the individual;
b) attributing at least two distinct interconverting microstates of an unliganded SHBG dimer having a first monomer and a second monomer by applying the New Multi-Step Dynamic Binding Model with Complex Allostery to the data of step a); and
c) calculating the free testosterone concentration in the individual using the New Multi-Step Dynamic Binding Model with Complex Allostery encompassing readjustment of a first equilibria between the microstates upon binding of a first testosterone molecule to the first monomer and an allosteric interaction between two binding sites of the SHBG dimer.
8. The computer system of paragraph 7, wherein step b) is performed according to FIGS. 2, 3, 5, and 7.
9. The computer system of paragraph 7, wherein step c) is performed according to FIG. 7 or Example 5.
10. The computer system of paragraph 7, wherein the assay further comprises the step of determining the concentration of at least one non-testosterone steroid.
11. The computer system of paragraph 10, wherein the non-testosterone steroid is selected from the group consisting of an estradiol steroid, an estrone steroid, and a dihydrotestosterone steroid.
12. The computer system of paragraph 7, wherein the total SHBG concentration, the total testosterone concentration, and the total albumin concentration is determined using an assay selected from the group consisting of an immunoassay, a binding assay, and a mass-spectrometry assay.
13. A non-transitory computer-readable storage medium storing one or more programs for treating an individual suspected of having an androgen disorder, the one or more programs for execution by one or more processors of a computer system, the one or more programs comprising instructions for:
a) receiving data from measuring i) a total SHBG concentration, ii) a total testosterone concentration, and iii) a total albumin concentration in a biological sample obtained from an individual, to determine free testosterone concentration from the individual;
b) attributing at least two distinct interconverting microstates of an unliganded SHBG dimer having a first monomer and a second monomer by applying the New Multi-Step Dynamic Binding Model with Complex Allostery to the data of step a); and
c) calculating the free testosterone concentration in the individual using the New Multi-Step Dynamic Binding Model with Complex Allostery encompassing readjustment of a first equilibria between the microstates upon binding of a first testosterone molecule to the first monomer and an allosteric interaction between two binding sites of the SHBG dimer.
14. The non-transitory computer-readable storage medium of paragraph 13, wherein step b) is performed according to FIGS. 2, 3, 5, and 7.
15. The non-transitory computer-readable storage medium of paragraph 13, wherein step c) is performed according to FIG. 7 and/or Example 5.
16. The non-transitory computer-readable storage medium of paragraph 13, wherein the system further comprises the step of determining the concentration of at least one non-testosterone steroid.
17. The non-transitory computer-readable storage medium of paragraph 16, wherein the non-testosterone steroid is selected from the group consisting of an estradiol steroid, an estrone steroid, and a dihydrotestosterone steroid.
18. The non-transitory computer-readable storage medium of paragraph 13, wherein the total SHBG concentration, the total testosterone concentration, and the total albumin concentration is determined using an assay selected from the group consisting of an immunoassay, a binding assay, and a mass-spectrometry assay.
19. An assay comprising the steps of:
a) measuring i) a total SHBG concentration, ii) a total testosterone concentration, and iii) a total albumin concentration in a biological sample obtained from an individual, to determine free testosterone concentration from the individual;
b) attributing at least two distinct interconverting microstates of an unliganded SHBG dimer having a first monomer and a second monomer by applying the New Multi-Step Dynamic Binding Model with Complex Allostery to the data of step a); and
c) calculating the free testosterone concentration in the individual using the New Multi-Step Dynamic Binding Model with Complex Allostery encompassing readjustment of a first equilibria between the microstates upon binding of a first testosterone molecule to the first monomer and an allosteric interaction between two binding sites of the SHBG dimer
20. The assay of paragraph 19, wherein step b) is performed according to FIGS. 2, 3, 5, and 7.
21. The assay of paragraph 19, wherein step c) is performed according to FIG. 7 and/or Example 5.

22. The assay of paragraph 19, wherein the assay further comprises the step of determining the concentration of at least one non-testosterone steroid.

23. The assay of paragraph 22, wherein the non-testosterone steroid is selected from the group consisting of an estradiol steroid, an estrone steroid, and a dihydrotestosterone steroid.

24. The assay of paragraph 19, wherein the total SHBG concentration, the total testosterone concentration, and the total albumin concentration is determined using an assay selected from the group consisting of an immunoassay, a binding assay, and a mass-spectrometry assay.

25. A computer implemented method for treating an individual suspected of having an androgen disorder, comprising:
on a device having one or more processors and a memory storing one or more programs for execution by the one or more processors, the one or more programs including instructions for:
   a) receiving data from measuring i) a total SHBG concentration, ii) a total testosterone concentration, and iii) a total albumin concentration in a biological sample obtained from an individual suspected of having an androgen disorder, to determine free testosterone concentration from the individual;
   b) attributing at least two distinct interconverting microstates of an unliganded SHBG dimer having a first monomer and a second monomer by applying the New Multi-Step Dynamic Binding Model with Complex Allostery to the data of step a);
   c) calculating the free testosterone concentration in the individual using a New Multi-step Dynamic Binding Model with Complex Allostery encompassing readjustment of a first equilibria between the microstates upon binding of a first testosterone molecule to the first monomer and an allosteric interaction between two binding sites of the SHBG dimer;
   d) sending a signal for administering a pharmaceutically effective amount of testosterone to an individual having a free testosterone concentration below the lower limit of a normal free testosterone concentration from a healthy individual (e.g., in one embodiment, the lower limit is 114.6 pg/ml); and
   e) sending a signal for not administering a pharmaceutically effective amount of testosterone to an individual having a free testosterone concentration above the lower limit of the normal free testosterone concentration from a healthy individual (e.g., in one embodiment, the lower limit is 114.6 pg/ml).

26. The computer implemented method of paragraph 25, wherein step c) is performed according to FIGS. 2, 3, 5, and 7.

27. The computer implemented method of paragraph 25, wherein step d) is performed according to FIG. 7 or Example 5.

28. The computer implemented method of paragraph 25, wherein the individual is a male over the age of 35.

29. The computer implemented method of paragraph 25, wherein the androgen disorder is selected from the group consisting of a testosterone deficiency, an androgen deficiency, a hyperandrogenic disorder, an androgen expressing tumor, and a hypogonadism disorder.

30. The computer implemented method of paragraph 25, wherein the androgen disorder is a hyperandrogenic disorder selected from the group consisting of an acne disorder, a hirsutism disorder, and an androgenic alopecia disorder.

31. The computer implemented method of paragraph 25, wherein the individual has been diagnosed with a disease selected from the group consisting of: diabetes, human immunodeficiency virus (HIV), hepatitis B, hepatitis C, hypothyroidism or hyperthyroidism, androgen insensitivity, acromegaly, anorexia, muscular dystrophy, liver disease, cancer cachexia, malnutrition, nephrotic syndrome, and obesity, and other conditions in which SHBG or albumin concentrations are altered.

32. The computer implemented method of paragraph 25, further comprising the step of classifying the individual into categories based on additional clinical symptoms.

33. A computer system for treating an individual suspected of having an androgen disorder, comprising:
one or more processors; and
memory to store:
one or more programs, the one or more programs comprising:
instructions for:
   a) receiving data from measuring i) a total SHBG concentration, ii) a total testosterone concentration, and iii) a total albumin concentration in a biological sample obtained from an individual suspected of having an androgen disorder, to determine free testosterone concentration from the individual;
   b) attributing at least two distinct interconverting microstates of an unliganded SHBG dimer having a first monomer and a second monomer by applying the New Multi-Step Dynamic Binding Model with Complex Allostery to the data of step a);
   c) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer;
   d) sending a signal for administering to a pharmaceutically effective amount of testosterone to an individual having a free testosterone concentration below the lower limit of a normal free testosterone concentration from a healthy individual (e.g., in one embodiment, the lower limit is 114.6 pg/ml); and
   e) sending a signal for not administering a pharmaceutically effective amount of testosterone to an individual having a free testosterone concentration above the lower limit of the normal free testosterone concentration from a healthy individual (e.g., in one embodiment, the lower limit is 114.6 pg/ml).

34. The computer system of paragraph 33, wherein step c) is performed according to FIGS. 2, 3, 5, and 7.

35. The computer system of paragraph 33, wherein step d) is performed according to FIG. 7 and/or Example 5.

36. The computer system of paragraph 33, wherein the individual is a male over the age of 35.

37. The computer system of paragraph 33, wherein the androgen disorder is selected from the group consisting of a testosterone deficiency, an androgen deficiency, a hyperandrogenic disorder, and a hypogonadism disorder.

38. The computer system of paragraph 33, wherein the androgen disorder is a hyperandrogenic disorder selected form the group consisting of an acne disorder, a hirsutism disorder, an androgen expressing tumor, and an androgenic alopecia disorder.

39. The computer system of paragraph 33, wherein the individual has been diagnosed with a disease selected from the group consisting of: diabetes, human immunodeficiency virus (HIV), hepatitis B, hepatitis C, hypothyroidism, hyperthyroidism, androgen insensitivity, acromegaly, anorexia, muscular dystrophy, liver disease, cancer cachexia, malnutrition, nephrotic syndrome, and obesity, and other conditions in which SHBG or albumin concentrations are altered.

40. The computer system of paragraph 33, further comprising the step of classifying the individual into categories based on additional clinical symptoms.

41. A non-transitory computer-readable storage medium storing one or more programs for treating an individual suspected of having an androgen disorder, the one or more programs for execution by one or more processors of a computer system, the one or more programs comprising instructions for:
    a) receiving data from measuring i) a total SHBG concentration, ii) a total testosterone concentration, and iii) a total albumin concentration in a biological sample obtained from an individual suspected of having an androgen disorder, to determine free testosterone concentration from the individual;
    b) attributing at least two distinct interconverting microstates of an unliganded SHBG dimer having a first monomer and a second monomer by applying the New Multi-Step Dynamic Binding Model with Complex Allostery to the data of step a);
    c) calculating the free testosterone concentration in the individual using New Multi-step Dynamic Binding Model with Complex Allostery encompassing readjustment of a first equilibria between the microstates upon binding of a first testosterone molecule to the first monomer and an allosteric interaction between two binding sites of the SHBG dimer;
    d) sending a signal for administering a pharmaceutically effective amount of testosterone to an individual having a free testosterone concentration below the lower limit of a normal free testosterone concentration from a healthy individual (e.g., in one embodiment, below 114.6 pg/ml); and
    e) sending a signal for not administering a pharmaceutically effective amount of testosterone to an individual having a free testosterone concentration above the lower limit of the normal free testosterone concentration from a healthy individual (e.g., in one embodiment, above 114.6 pg/ml, the lower limit of this assay).

42. The non-transitory computer-readable storage medium of paragraph 41, wherein step c) is performed according to FIGS. 2, 3, 5, and 7.

43. The non-transitory computer-readable storage medium of paragraph 41, wherein step d) is according to FIG. 7 or Example 5.

44. The non-transitory computer-readable storage medium of paragraph 41, wherein the individual is a male over the age of 35.

45. The non-transitory computer-readable storage medium of paragraph 41, wherein the androgen disorder is selected from the group consisting of a testosterone deficiency, an androgen deficiency, a hyperandrogenic disorder, and a hypogonadism disorder.

46. The non-transitory computer-readable storage medium of paragraph 41, wherein the androgen disorder is a hyperandrogenic disorder selected form the group consisting of an acne disorder, a hirsutism disorder, an androgen expressing tumor, and an androgenic alopecia disorder.

47. The non-transitory computer-readable storage medium of paragraph 41, wherein the individual has been diagnosed with a disease selected from the group consisting of: diabetes, human immunodeficiency virus (HIV), hypothyroidism, hyperthyroidism, hepatitis B, hepatitis C, androgen insensitivity, acromegaly, anorexia, muscular dystrophy, liver disease, cancer cachexia, malnutrition, nephrotic syndrome, and obesity . . . .

48. The non-transitory computer-readable storage medium of paragraph 41, further comprising the step of classifying the individual into categories based on additional clinical symptoms.

49. A method for treating an individual suspected of having an androgen disorder comprising:
    a) administering a pharmaceutically effective amount of testosterone to an individual who has had a free testosterone level determined by measuring i) a total SHBG concentration, ii) a total testosterone concentration, and iii) a total albumin concentration in a biological sample from the individual suspected of having an androgen disorder;
    b) attributing at least two distinct interconverting microstates of an unliganded SHBG dimer having a first monomer and a second monomer by applying the New Multi-Step Dynamic Binding Model with Complex Allostery to the data of step a);
    c) calculating the free testosterone concentration in the individual using an the New Multi-step Dynamic Binding Model with Complex Allostery encompassing readjustment of a first equilibria between the microstates upon binding of a first testosterone molecule to the first monomer and an allosteric interaction between two binding sites of the SHBG dimer;
    d) administering a pharmaceutically effective amount of testosterone to an individual having a free testosterone concentration below the lower limit of a normal free testosterone concentration from a healthy individual (e.g., in one embodiment, below 114.6 pg/ml); and
    e) not administering a pharmaceutically effective amount of testosterone to an individual having a free testosterone concentration above the lower limit of the normal free testosterone concentration from a healthy individual (e.g., in one embodiment, above 114.6 pg/ml, the lower limit of this assay).

50. The method of paragraph 49, wherein step c) is performed according to FIGS. 2, 3, 5, and 7.

51. The method of paragraph 49, wherein step d) is performed according to FIG. 7 or Example 5.

52. The method of paragraph 49, wherein the individual is a male over the age of 35.

53. The method of paragraph 49, wherein the androgen disorder is selected from the group consisting of a testosterone deficiency, an androgen deficiency, and a hypogonadism disorder.

54. The method of paragraph 49, wherein the individual has been diagnosed with a disease selected from the group consisting of: diabetes, obesity, human immunodeficiency virus (HIV), hepatitis B, hepatitis C, hypothyroidism, hyperthyroidism, androgen insensitivity, acromegaly, anorexia, muscular dystrophy, liver disease, cancer cachexia, malnutrition, nephrotic syndrome, obesity, and other conditions in which SHBG or albumin concentrations are altered.

55. The method of paragraph 49, further comprising the step of classifying the individual into categories based on additional clinical symptoms.

56. A computer implemented method for determining a need for adjustment of a dose of testosterone administered to an individual with hypogonadism, androgen deficiency syndrome, or any other condition for which testosterone therapy is indicated, comprising: on a device having one or more processors and a memory storing one or more programs for execution by the one or more processors, the one or more programs including instructions for:
    a) receiving data from determining the concentration of free testosterone in an individual receiving testosterone therapy at a first dose, wherein the concentration of free testosterone is determined by measuring i) a total SHBG concentration, ii) a total testosterone concentration, and iii) a total albumin concentration in a biological sample obtained from an individual, to determine free testosterone concentration from the individual;
    b) attributing at least two distinct interconverting microstates of an unliganded SHBG dimer having a first monomer and a second monomer by applying the New Multi-Step Dynamic Binding Model with Complex Allostery to the data of step a);
    c) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer and;
    d) sending a signal for providing a second (adjusted) dose of testosterone that is higher than the first dose when the free testosterone concentration is below the lower end of the target therapeutic (e.g. 164 pg/ml); and
    e) sending a signal for providing a second (adjusted) dose of testosterone that is lower than the first dose when the free testosterone concentration is above the upper end of the target therapeutic range (e.g. 314 pg/ml).

57. The computer implemented method of paragraph 56, further comprising the step of receiving data of the first dose of testosterone administered to the individual.

58. The computer implemented method of paragraph 56, wherein step b) is performed according to FIGS. 2, 3, 5, and 7.

59. The computer implemented method of paragraph 56, wherein step c) is performed according to FIG. 7 or Example 5.

60. The computer implemented method of paragraph 56, wherein the individual is a male over the age of 35.

61. The computer implemented method of paragraph 56, wherein the individual has a disorder selected from the group consisting of a testosterone deficiency, an androgen deficiency, and a hypogonadism disorder.

62. The computer implemented method of paragraph 56, wherein the individual has been diagnosed with a disease selected from the group consisting of: diabetes, obesity, human immunodeficiency virus (HIV), hepatitis B, hepatitis C, hypothyroidism, hyperthyroidism, androgen insensitivity, acromegaly, anorexia, muscular dystrophy, liver disease, cancer cachexia, malnutrition, nephrotic syndrome, obesity, and other conditions in which SHBG or albumin concentrations are altered.

63. A computer system for determining a need for adjustment of a dose of testosterone administered to an individual, comprising:
    one or more processors; and
    memory to store:
    one or more programs, the one or more programs comprising:
    instructions for:
        a) receiving data from determining the concentration of free testosterone in an individual receiving testosterone therapy at a first dose, wherein the concentration of free testosterone is determined by measuring i) a total SHBG concentration, ii) a total testosterone concentration, and iii) a total albumin concentration in a biological sample obtained from an individual, to determine free testosterone concentration from the individual;
        b) attributing at least two distinct interconverting microstates of an unliganded SHBG dimer having a first monomer and a second monomer by applying the New Multi-Step Dynamic Binding Model with Complex Allostery to the data of step a);
        c) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer;
        d) sending a signal for providing a second dose of testosterone that is higher than the first dose when the free testosterone concentration is below the lower end of the target therapeutic range (e.g. 164 pg/ml); and
        e) sending a signal for providing a second dose of testosterone that is lower than the first dose when the free testosterone concentration is above the upper end of the target therapeutic range (e.g. 314 pg/ml).

64. The computer implemented method of paragraph 63, wherein step c) is performed according to FIGS. 2, 3, 5, and 7.

65. The computer implemented method of paragraph 63, wherein step d) is performed according to FIG. 7 or Example 5.

66. The computer implemented method of paragraph 63, wherein the individual is a male over the age of 35.

67. The computer implemented method of paragraph 63, wherein the individual has a disorder selected from the group consisting of a testosterone deficiency, an androgen deficiency, and a hypogonadism disorder, or any condition for which testosterone therapy is indicated or may be given.

68. The computer implemented method of paragraph 63, wherein the androgen disorder is a hyperandrogenic disorder selected form the group consisting of an acne disorder, a hirsutism disorder, an androgen expressing tumor, and an androgenic alopecia disorder.

69. The computer implemented method of paragraph 63, wherein the individual has been diagnosed with a disease selected from the group consisting of: diabetes, human immunodeficiency virus (HIV), hepatitis B, hepatitis C, hypothyroidism, hyperthyroidism, androgen insensitivity, acromegaly, anorexia, muscular dystrophy, liver disease, cancer cachexia, malnutrition, nephrotic syndrome, obesity, and any condition in which SHBG or albumin concentrations are altered.

70. A non-transitory computer-readable storage medium storing one or more programs for determining a need for adjustment of a dose of testosterone administered to an individual, the one or more programs for execution by one or more processors of a computer system, the one or more programs comprising instructions for:
   a. receiving data from determining the concentration of free testosterone in an individual receiving testosterone therapy at a first dose, wherein the concentration of free testosterone is determined by measuring i) a total SHBG concentration, ii) a total testosterone concentration, and iii) a total albumin concentration in a biological sample obtained from an individual, to determine free testosterone concentration from the individual;
   b. attributing at least two distinct interconverting microstates of an unliganded SHBG dimer having a first monomer and a second monomer by applying the New Multi-Step Dynamic Binding Model with Complex Allostery to the data of step a);
   c. calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer;
   d. sending a signal for providing a second dose of testosterone that is higher than the first dose when the free testosterone concentration is below the lower end of the target therapeutic range (e.g. 164 pg/ml); and
   e. sending a signal for providing a second dose of testosterone that is lower than the first dose when the free testosterone concentration is above the upper end of the target therapeutic range (e.g. 314 pg/ml).

71. The non-transitory computer-readable storage medium of paragraph 70, wherein step c) is performed according to FIGS. 2, 3, 5, and 7.

72. The non-transitory computer-readable storage medium of paragraph 70, wherein step d) is performed according to FIG. 7 or Example 5.

73. The non-transitory computer-readable storage medium of paragraph 70, wherein the individual is a male over the age of 35.

74. The non-transitory computer-readable storage medium of paragraph 70, wherein the individual has a disorder selected from the group consisting of a testosterone deficiency, an androgen deficiency, and a hypogonadism disorder, or any other condition in which testosterone therapy may be given or is indicated.

75. The non-transitory computer-readable storage medium of paragraph 70, wherein the individual has been diagnosed with a disease selected from the group consisting of: diabetes, human immunodeficiency virus (HIV), hepatitis B, hepatitis C, hypothyroidism, hyperthyroidism, androgen insensitivity, acromegaly, anorexia, muscular dystrophy, liver disease, cancer cachexia, malnutrition, nephrotic syndrome, obesity, and any condition in which SHBG or albumin concentrations are altered.

76. A method for determining a need for adjustment of a dose of testosterone administered to an individual comprising
   a) determining the concentration of free testosterone in an individual receiving testosterone therapy at a first dose, wherein the concentration of free testosterone is determined by
   b) measuring i) a total SHBG concentration, ii) a total testosterone concentration, and iii) a total albumin concentration in a biological sample obtained from an individual, to determine free testosterone concentration from the individual;
   c) attributing at least two distinct interconverting microstates of an unliganded SHBG dimer having a first monomer and a second monomer by applying the New Multi-Step Dynamic Binding Model with Complex Allostery to the data of steps a) and b);
   d) calculating the free testosterone concentration in the individual using the New Multi-step Dynamic Binding Model with Complex Allostery encompassing readjustment of a first equilibria between the microstates upon binding of a first testosterone molecule to the first monomer and an allosteric interaction between two binding sites of the SHBG dimer;
   e) providing a second dose of testosterone that is higher than the first dose when the free testosterone concentration is below the lower end of the target therapeutic range (e.g. 164 pg/ml); and
   f) providing a second dose of testosterone that is lower than the first dose when the free testosterone concentration is above the upper end of the target therapeutic range (314 pg/ml).

77. The method of paragraph 76, wherein step c) is performed according to FIGS. 2, 3, 5, and 7.

78. The method of paragraph 76, wherein step d) is performed according to FIG. 7 or Example 5.

79. The method of paragraph 76, wherein the individual is a male over the age of 35.

80. The method of paragraph 76, wherein the individual has a disorder selected from the group consisting of a testosterone deficiency, an androgen deficiency, and a hypogonadism disorder.

81. The method of paragraph 76, wherein the individual has been diagnosed with a disease selected from the group consisting of: diabetes, human immunodeficiency virus (HIV), hepatitis B, hepatitis C, hypothyroidism, hyperthyroidism, androgen insensitivity, acromegaly, anorexia, muscular dystrophy, liver disease, cancer cachexia, malnutrition, nephrotic syndrome, and obesity, or any other condition in which SHBG and/or albumin concentrations.

82. The method of paragraph 76, wherein the method comprises the step of: using the free testosterone concentration determined using the new Multistep Dynamic Binding Model with Complex Allostery to determine the dose or to individually adjust the dose of a formulation of testosterone for the treatment of a medical disease, taking into account patient's age, body weight and body mass index, medical conditions, including any co-morbid conditions, albumin and SHBG, and/or LH and FSH concentrations, and other patient-specific factors.

EXAMPLES

Example 1

Determination of Free Sex Steroid Concentration

In conditions characterized by alterations in sex-hormone binding globulin (SHBG), total testosterone (TT) may not reflect the androgen status accurately and estimates of free testosterone (FT) are needed. Equations based on the prevailing model of SHBG:T interaction, although known to be systematically erroneous, have been used widely to calculate free testosterone.

Methods. Free testosterone concentrations calculated using a law-of-mass-action equation differ substantially from those measured using equilibrium dialysis. We investigated the dynamics of testosterone and SHBG interaction using binding isotherms, SHBG depletion curves, and isothermal titration calorimetry (ITC). The FT values calculated from new model derived from these experiments were compared to equilibrium dialysis using samples from randomized testosterone trials in men and women.

Results. Binding isotherms generated by incubating 5, 10 or 20 nM SHBG with 0-to-400 nM testosterone could not be explained by the prevailing model developed by Vermeulen et al. (1). Comprehensive evaluation of data derived from binding isotherms, ligand depletion curves, and ITC suggested a complex association of testosterone with SHBG dimer; the new Multi-step Dynamic Binding Model with Complex Allostery that provided the best fit to these data encompasses at least two inter-converting microstates in unliganded SHBG, readjustment of equilibria between unliganded states upon binding of the first ligand molecule, and allosteric interaction between two binding sites of SHBG dimer. In samples from testosterone trials in men and women, free testosterone predicted using the new Multi-step Dynamic Binding Model with Complex Allostery did not systematically differ from that measured using equilibrium dialysis.

The new Multi-step Dynamic Binding Model with Complex Allostery of testosterone's binding to SHBG provides excellent fit to experimental data derived from binding isotherm, depletion curves and ITC. Free testosterone concentrations calculated using the new Multi-step Dynamic Binding Model with Complex Allostery closely match those measured using equilibrium dialysis.

Testosterone, the major androgen in humans, circulates in blood bound largely to sex hormone binding globulin (SHBG) and albumin. Testosterone can also bind to orosomucoid and transcortin proteins. According to the free hormone hypothesis, only the unbound or free fraction—0.5 to 3.0% of total—can cross the plasma membrane and is biologically active. In many conditions that affect SHBG concentrations, such as obesity, diabetes, aging, hyperthyroidism, liver disease, acromegaly, and HIV-infection, total testosterone concentrations are altered because of the changes in SHBG concentrations; in these conditions, determination of free testosterone concentration is needed to obtain an accurate assessment of androgen status.

A number of direct and indirect methods—equilibrium dialysis, ultrafiltration, tracer analog methods, and calculations based on homogenous SHBG:T binding equation—for the determination of free testosterone have been published (2-8). The accuracy of the available assays for the measurement of free testosterone has engendered concern (3). Equilibrium dialysis is widely considered the reference method, but the method is cumbersome, affected by dialysis conditions and tracer impurities, and has lower precision (3). The tracer analog methods are convenient but inaccurate (9). Bioavailable testosterone levels (the unbound testosterone plus testosterone bound to albumin) can be measured by the ammonium sulfate precipitation method (9-12), but the methodological difficulties in performing these assays led the Endocrine Society's Expert Panel to shy away from recommending its use outside of research laboratories (3). Recognizing these methodological difficulties in the measurement of free testosterone, the Endocrine Society's Expert Panel suggested that "the calculation of free testosterone concentration from reliably measured total testosterone and SHBG using mass action equations provides the best approach for the estimation of free testosterone concentration (3)". Therefore, algorithms for calculating free testosterone from total testosterone, SHBG and albumin concentrations using the law-of-mass-action equations (1, 13-16) or empirically-derived equations (13-16) have been published, advocated, and used widely.

The current equations based on homogenous SHBG:T interaction (equal affinity of T for each of the monomers within SHBG dimer and without allostery in SHBG dimers) proposed by Vermeulen and others (13, 17) are based on the assumption that each SHBG dimer binds two testosterone molecules, and that each of the two binding sites on SHBG dimer has similar binding constants (data not shown). It is demonstrated herein that the current model of testosterone binding to SHBG that has formed the basis of the law-of-mass-action equation is erroneous; the free testosterone levels derived from these equations display substantial discrepancy from the values obtained by equilibrium dialysis (18). Based on binding isotherms, ligand depletion experiments, and isothermal titration calorimetry (ITC), we provide experimental evidence of complex allostery between the binding sites on the two SHBG monomers in the presence of the ligand. Based on this new model of testosterone binding to SHBG, described herein is a novel algorithm for the calculation of free testosterone, applied it to samples derived from randomized testosterone trials in men and women, and compared the results with those obtained using equilibrium dialysis.

Materials and Methods. Human SHBG purified from serum (The Binding Site Group, Ltd Birmingham, UK cat# BH089.X) was characterized by protein gel denaturation-renaturation experiments and by measuring its ability to bind testosterone. Testosterone standard 1.0 mg/mL±2% (3.47 mM) was obtained from Cerilliant (Round Rock, Tex.).

Equilibrium dialysis was performed in 96-Well equilibrium dialysis chambers with 10 kDa molecular weight cut-off (Harvard Apparatus, Holliston, Mass. cat#742331). Equilibrium dialysis buffer contained 30 mM HEPES buffer pH 7.4, 90 mM NaCl, 1 mM $MgSO_4$, 187 uM $CaCl_2$ in ultrapure water. For binding and depletion assays, SHBG was reconstituted in equilibrium dialysis buffer. Testosterone concentration was measured using a liquid chromatography tandem mass spectrometry (LC-MS/MS) assay that has been certified by the Center for Disease Control's HoST Program(19).

Isothermal calorimetry(ITC) experiments were performed using fully automated Auto-ITC200 calorimeter from MicroCal (Northampton, Mass.) provided by Automated Biological calorimetry Facility (Huck Institutes of Life Sciences, University Park, Pa.). SHBG was reconstituted in 30 mM HEPES buffer, pH 7.4, to a final concentration of 5 μM. Testosterone standard was prepared in DMSO and diluted in protein buffer to a concentration of 100 μM in 5% DMSO. DMSO was added to SHBG by weight to match DMSO content in the testosterone solution. Samples were degassed prior to loading to the calorimeter. Testosterone was injected into the protein solution in 32 equal steps. Heat produced by each injection was measured by the calorimeter. Interval between injections was set at 240 seconds so that the temperature could return to baseline. The amount of heat generated after each injection (after subtracting the heat of dilution of ligand in buffer) was integrated to produce calorimetric binding isotherm depicting the relationship of the total heat generated in the reaction to testosterone-to-SHBG molar ratio.

Application of the Novel Algorithm to Clinical Trials Data. Free testosterone concentrations determined using the novel algorithm described herein and by the Vermeulen's law-of-mass-action equation, were compared (implemented in a spreadsheet by Mazer) against those measured using the reference method (equilibrium dialysis), in samples derived from randomized testosterone trials in men (101) and women (102). These samples had been collected in fasting state in the morning, stored immediately after collection at −80° C., and never thawed.

Testosterone in Men with Erectile Dysfunction (TED) Trial. The TED Trial, whose design and results have been published (20), was a randomized, placebo-controlled trial to determine whether addition of testosterone to an optimized regimen of sildenafil citrate improves erectile function in men with erectile dysfunction (ED) and low testosterone levels. At baseline and after 12-weeks of testosterone or placebo administration, serum total testosterone concentrations were measured using LC-MS/MS and SHBG concentrations measured by a two-site immunofluorometric assay (DELFIA® SHBG Kit, cat# A070-101, Perkin-Elmer, Waltham, Mass.). Free testosterone concentrations were measured in the same samples by equilibrium dialysis.

Results

Figure 1B:
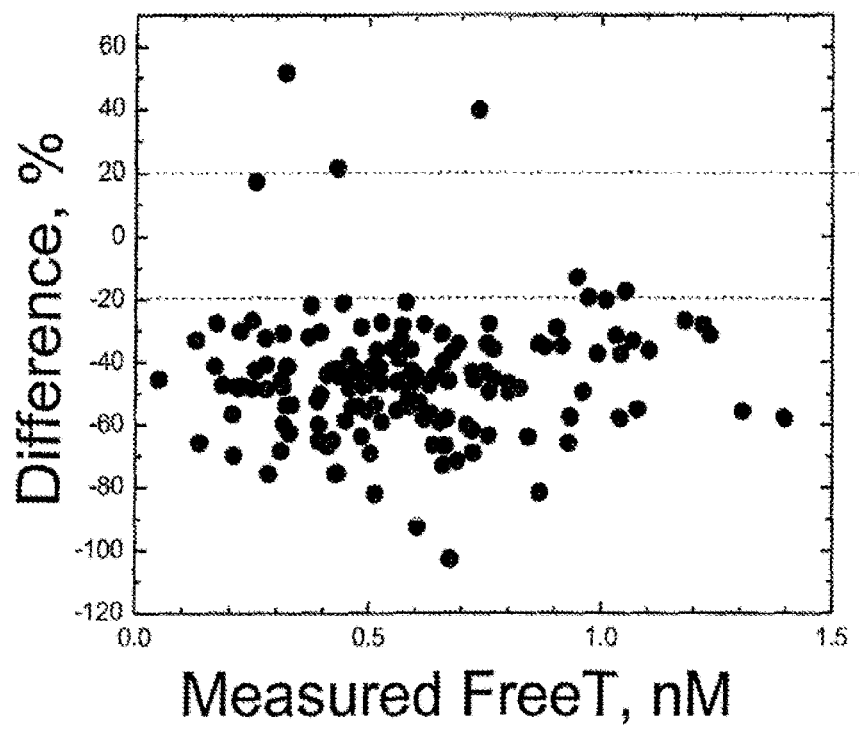
Figure 2A:
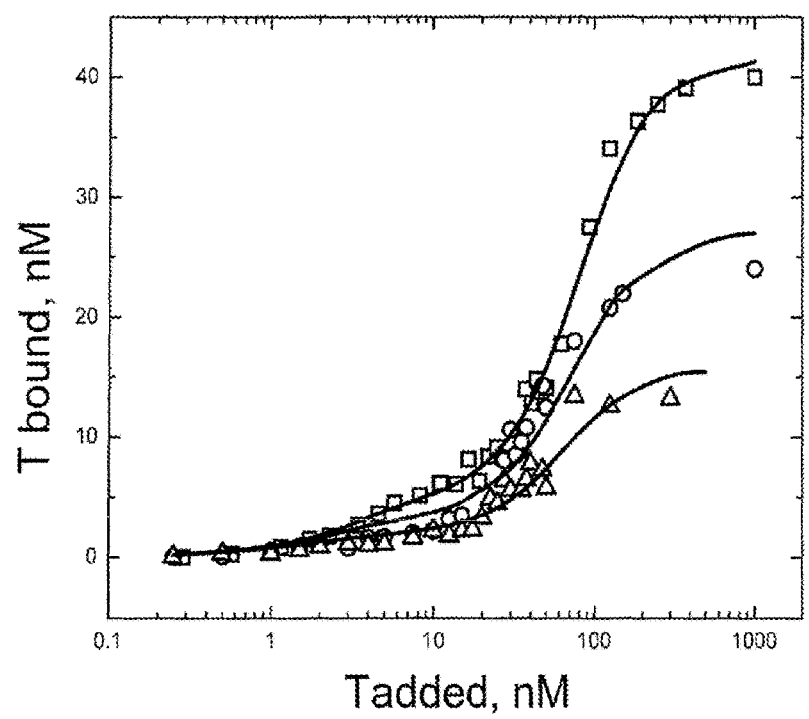
FIGS. 2A-2C demonstrate that binding of testosterone to SHBG displays complex behavior.
Figure 2B:
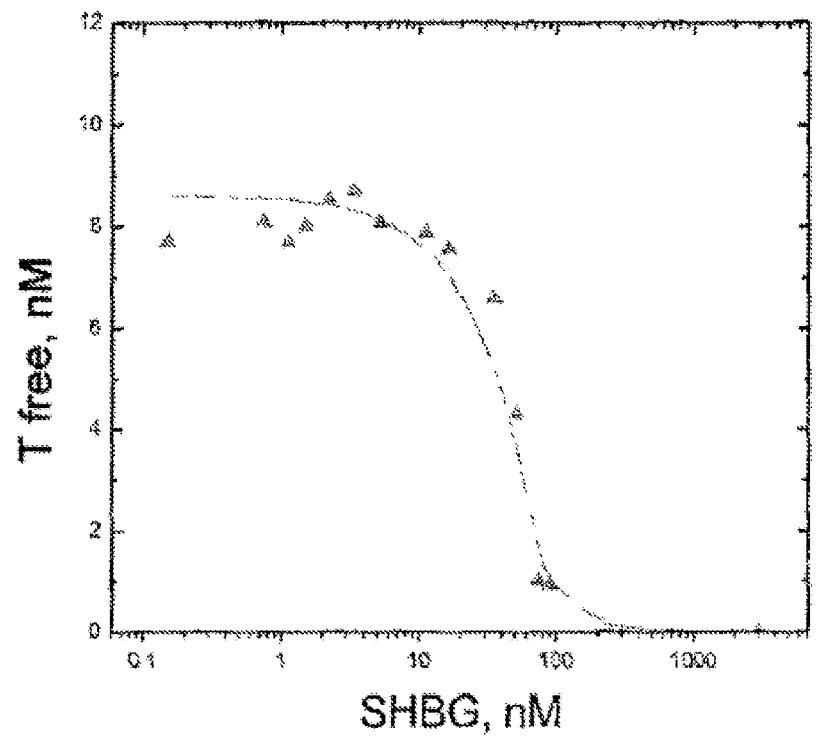
Figure 2C:
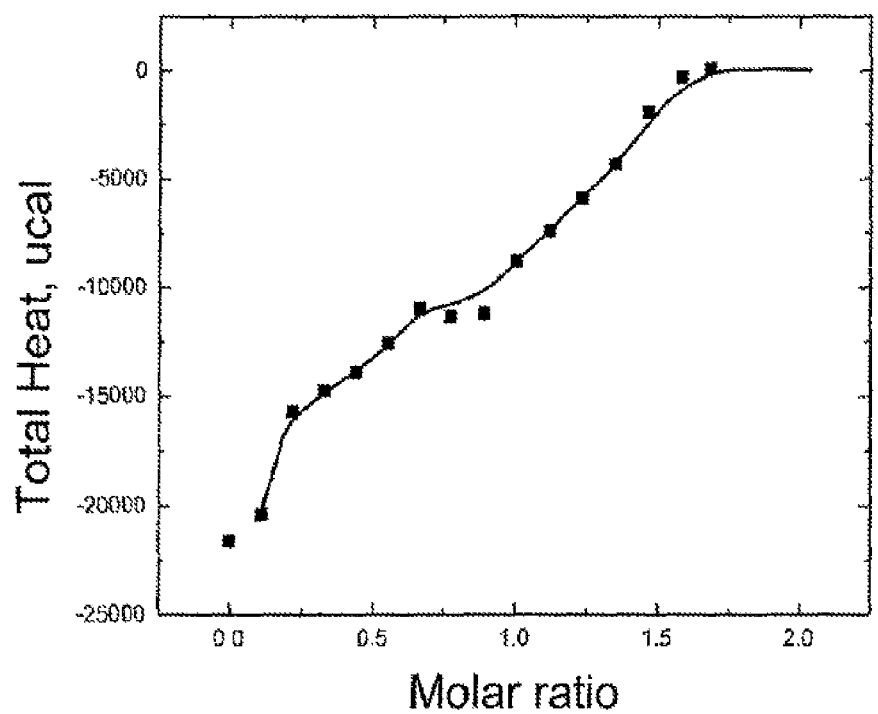

The free testosterone concentrations calculated by the Vermeulen's equation (24) were compared with those measured using equilibrium dialysis in samples derived from participants in the TED Trial. As shown in FIG. 1A, free testosterone concentrations estimated by this equation were significantly lower than those measured by equilibrium dialysis. Bland Altman plot (FIG. 1B) confirmed the substantial underestimation of free testosterone concentration by the Veinieulen's equation relative to that measured by equilibrium dialysis, although the estimation error was not linearly related to the measured free testosterone concentrations. To determine the molecular basis of this discrepancy, we used three experimental approaches to characterize testosterone's binding to SHBG: the binding isotherms, the ligand depletion curve, and the isothermal titration calorimetry (ITC).

Testosterone: SHBG binding Isotherms display evidence of homoallosteric association between testosterone and SHBG dimers. To generate the binding isotherms, 5, 10 or 20 nM SHBG protein (dimer) was incubated with graded concentrations of testosterone (0 to 400 nM) at room temperature (20° C.). The mixture was dialyzed overnight against an equal volume of the dialysis buffer and testosterone concentration in the dialysate was determined by LC-MS/MS. When bound testosterone concentration was plotted against total testosterone concentration (FIG. 2A), the binding isotherm displayed several distinct features: the existence of two distinct saturation plateaus (including an apparent plateau at lower testosterone concentrations), and asymmetry of the isotherm around the EC50value. The relationship of bound testosterone concentration to total testosterone could not be adequately fit by the Vermeulen's model/equation, which assumes that the two monomers within the SHBG dimer have similar binding constant.

Figure 3:
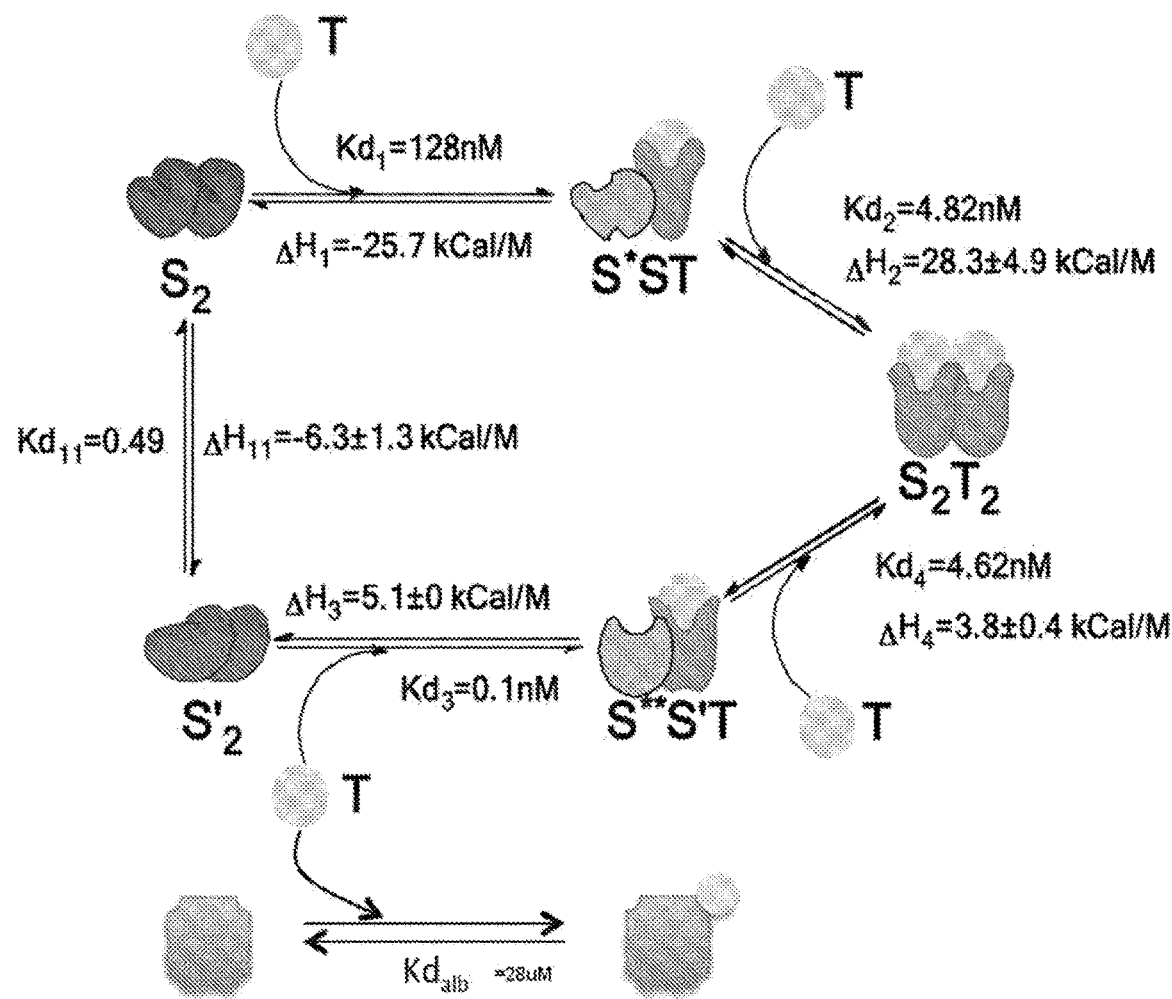
FIG. 3 depicts a schematic representation of the new Multi-step Dynamic Binding Model with Complex Allostery of testosterone's binding to SHBG and albumin, developed in this study. Unliganded SHBG dimers ($S_2$, $S_2'$) exist in conformational equilibrium. Upon binding of the first testosterone molecule to microstates $S_2$ and $S_2'$ can result in conformationally heterogeneous intermediate states $S_2T$ and $S_2'T$ respectively. These singly-occupied microstates then converge to $S_2T_2$ upon binding of the second testosterone molecule.
Figure 4A:
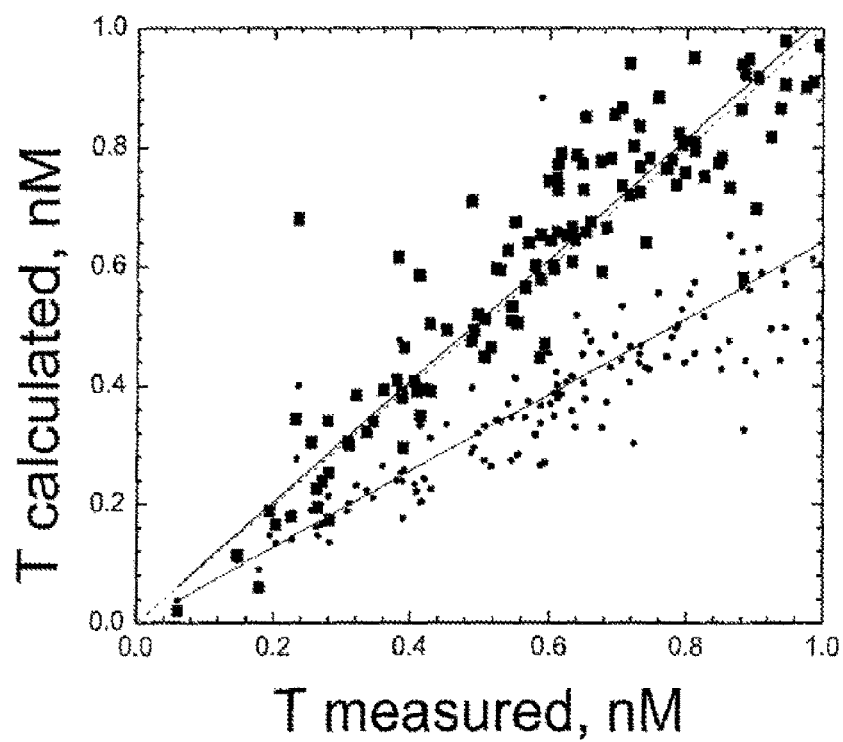
FIGS. 4A-4B demonstrate a comparison of the Free Testosterone Concentrations Derived Using the Vermeulen Equation (23) as implemented by Mazer (24) or the New Algorithm Based on the new Multi-step Dynamic Binding Model with Complex Allostery with those measured using the equilibrium dialysis in samples from the 5alpha reductase trial.
Figure 4B:
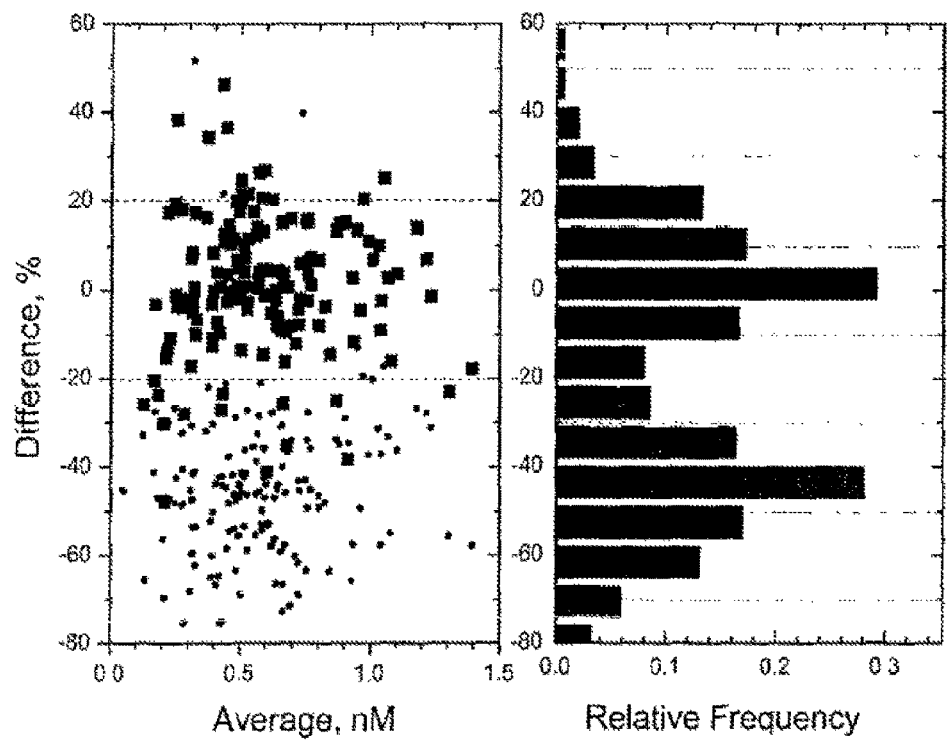
Figure 4C:
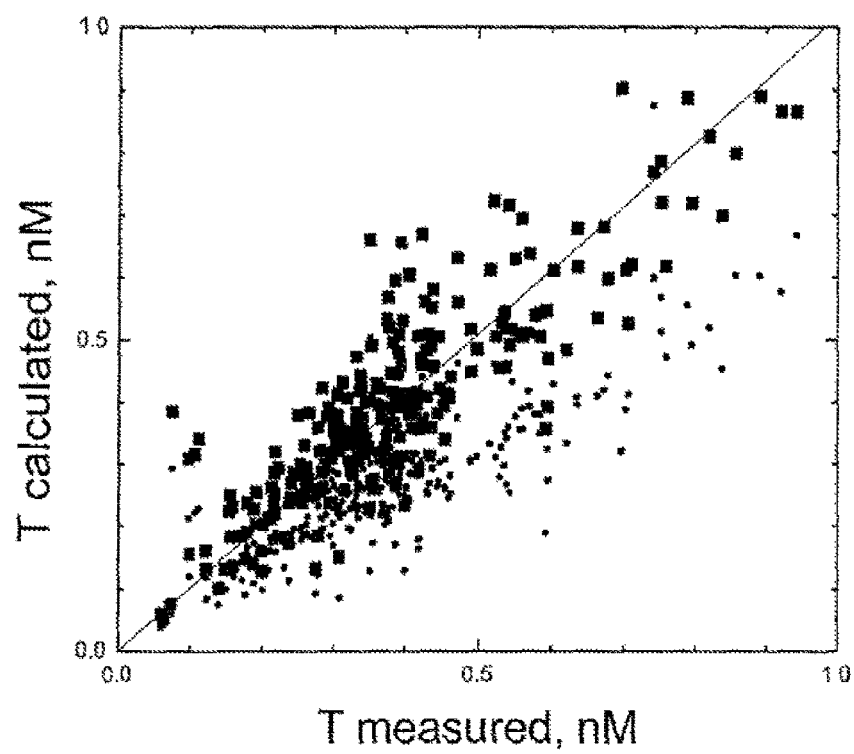
FIGS. 4C-4D depict a Comparison of the Free Testosterone Concentrations Derived Using the Vermeulen Equation or the New Algorithm Based on the new Multi-step Dynamic Binding Model with Complex Allostery with those measured using the equilibrium dialysis.
Figure 4D:
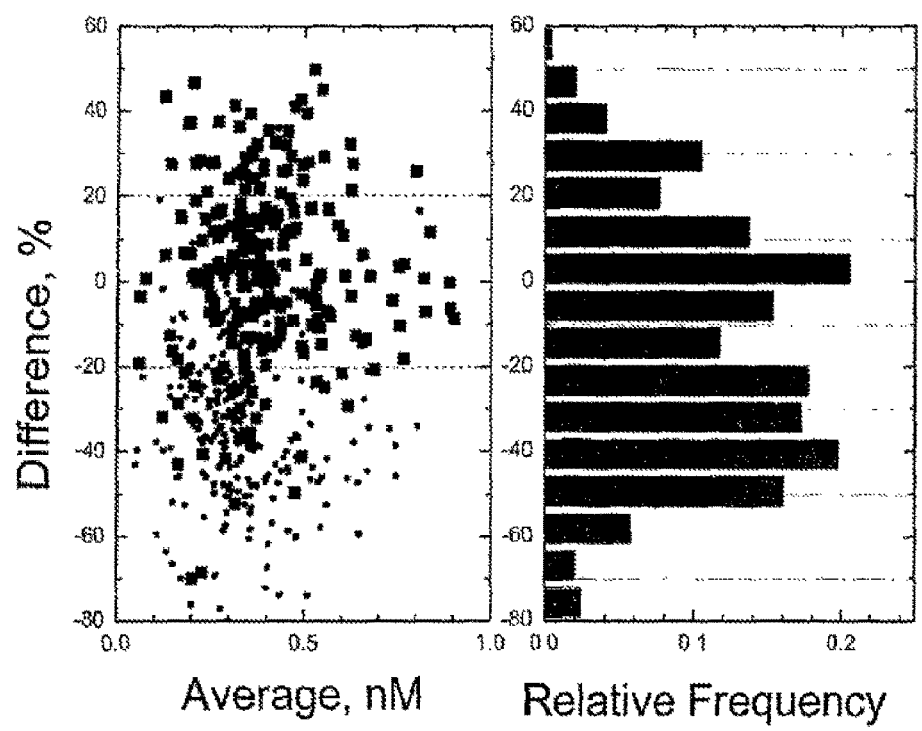

The new Multi-step Dynamic Binding Model with Complex Allostery presented in this study was developed iteratively to encompass all the features of the binding isotherms. In an attempt to comprehensively fit binding isotherms, several models were examined: a) the prevailing equations suggesting a homogenous interaction of two testosterone molecules, b) the monomers within dimer exhibiting distinct affinity constants, c) simple allostery where binding of first ligand alters the affinity of the second site and d) the new Multi-step Dynamic Binding Model with Complex Allostery including two distinct SHBG dimer microstates in equilibrium such that the equilibria between the unliganded and mono-liganded readjusts as the concentration of testosterone is increased. Consistent with the crystal structure data, all the models were constrained to eventually converge on to a single double liganded conformational state of SHBG dimer Of all the models tested, the new Multi-step Dynamic Binding Model with Complex Allostery adequately fit the binding isotherms. The schematic representation in FIG. 3 summarizes the complex dynamics of the T:SHBG interaction. In this model it was further tested if S1T and S1'T microstates were distinguishable or not. That model with converged S1T and S1'T states again fails to fit the data. The new Multi-step Dynamic Binding Model with Complex Allostery fit the binding isotherm optimally and explained the observed saturation plateaus, including the plateau at lower testosterone concentrations, and the asymmetry of the binding isotherm around the ES50.

Testosterone Depletion Curves. As an independent and complementary assessment of testosterone's binding to SHBG, we incubated various amounts of SHBG (0.1 to 500 nM) with a fixed concentration of testosterone, and analyzed the depletion of unbound testosterone when increasing concentrations of SHBG were added. These depletion curves were generated at several different testosterone concentrations (6 nM, 12 nM, 18 nM, and 32 nM). Mixtures of testosterone and SHBG were dialyzed overnight against a similar volume of the dialysis buffer and free testosterone concentration was measured by LC-MS/MS. The relationship of free testosterone concentration to SHBG concentration in the depletion experiments (FIG. 2B) was again best fit using the new Multi-step Dynamic Binding Model with Complex Allostery. The Vermeulen model did not provide an optimum fit (data not shown).

Isothermal Titration Calorimetry (ITC). To validate the new Multi-step Dynamic Binding Model with Complex Allostery further and to evaluate the thermodynamic parameters associated with testosterone binding to SHBG, ITC experiments were performed. The ITC isotherm has a characteristic shoulder (FIG. 2C) and cannot be adequately described as a simple sigmoidal curve predicted by the Vermeulen model nor by models B and C. Using the computational framework developed in LABVIEW (21), fits of the ITC data to the new Multi-step Dynamic Binding Model with Complex Allostery were generated (FIG. 3). Model constants obtained as a result of the linked fit in FIGS. 2A-2B were used as a starting point for the fit. The new Multi-step Dynamic Binding Model with Complex Allostery model provided an excellent fit for the experimental data derived from the ITC. The shape of the ITC curve can be explained as a convoluted result of testosterone binding and multiple conformational rearrangements defined by the new Multi-step Dynamic Binding Model with Complex Allostery. While, the independent enthalpy parameters for each of the individual reactions comprising the model were used, they are not simultaneously identifiable.

Application of the New Algorithm to Clinical Trials Data. The new model was applied to data generated in the TED trial (FIGS. 4A-4D). The free testosterone concentrations were calculated by the prevailing equations (23-24) and those calculated using the new algorithm based on new Multi-step Dynamic Binding Model with Complex Allostery (FIGS. 4A-4D). The prevailing model (17) significantly underestimated free testosterone levels relative to equilibrium dialysis in men participating in the TED trial. In contrast, the new Multi-step Dynamic Binding Model with Complex Allostery model provided values that were not statistically different from those measured by equilibrium dialysis (slope 1.01±0.01) in both men and women. The Bland-Altman plots (FIGS. 4A-4D) show the absence of any systematic difference between the values derived from the new Multi-step Dynamic Binding Model with Complex Allostery model and those obtained using the equilibrium dialysis in either men or women; the relative deviation of the values calculated using the new Multi-step Dynamic Binding Model with Complex Allostery model from those measured using equilibrium dialysis was evenly distributed around 0, likely reflecting multiple sources of measurement error in the testosterone assay, SHBG assay, and in the equilibrium dialysis method (FIGS. 4A-4D).

Discussion. It is demonstrated herein that the current model of testosterone binding to SHBG that has formed the basis of the law-of-mass-action equations for several decades to estimate free testosterone concentrations is erroneous. While the discrepancy between testosterone concentrations estimated using the available prevailing equations and those measured using the equilibrium dialysis method has been recognized ( ), the present data provide a rational mechanistic explanation for this discrepancy that had remained obscure previously. The experimental data from the binding isotherms, the SHBG depletion curves, and the ITC cannot be explained by the existing SHBG-T interaction model of single binding site or two identical, non-interacting binding sites on SHBG. The experimental data are poorly explained even by simple models for homotropic allostery within a dimer (e.g., Koshland-Nemesy-Filmer (22) and Monod-Wyman-Changeaux (23) models. In contrast, the new Multi-step Dynamic Binding Model with Complex Allostery (24, 25) optimally fits the data from the binding isotherms and also explains adequately the depletion curves and the ITC data. Furthermore, in samples derived from male and female participants in two separate clinical trials, testosterone concentrations calculated using the new Multi-step Dynamic Binding Model with Complex Allostery were statistically not different from those measured by the equilibrium dialysis.

The proposed new Multi-step Dynamic Binding Model with Complex Allostery indicates that in the absence of testosterone, SHBG molecule can assume one of at least two inter-converting microstates in a dynamic equilibrium. The binding of testosterone to one of the monomers of the SHBG dimer in a given microstate affects the interaction of testosterone with the unoccupied second binding site on the SHBG dimer. The model suggests a dynamic readjustment of populations of intermediate species as testosterone concentrations are altered. Independent experimental validation of model was performed by generating ligand depletion and ITC studies. The data from three sets (equilibrium binding, ligand depletion and ITC) were successfully fit by the new Multi-step Dynamic Binding Model with Complex Allostery. Without wishing to be bound by theory, the parameters in the model are not uniquely determined and could require detailed experimental evaluation of each microstate in multiple equilibria.

Prevailing hypothesis that has formulated the basis of the equations/expressions by Vermeulen assumes that monomers within a dimer display identical association constant without any dynamic interaction between the subunits. The general idea was supported by ligand bound crystal structure of SHBG (36). Parenthetically, the crystal structures are typically obtained in saturating concentrations of ligands. It is possible that the inability to resolve the unliganded SHBG structure (26) as well as the increased stability of SHBG upon ligand binding (27) may be related to the significant rearrangement of SHBG molecule upon binding of the first ligand, as predicted by the new Multi-step Dynamic Binding Model with Complex Allostery (24). The additional energy barrier that SHBG has to overcome may result in altered affinity for binding of the second ligand molecule. Further studies utilizing dimerization deficient mutants as well as molecular dynamics simulations are required to precisely define biophysical parameters associated with each ligand binding event.

The algorithm based on new Multi-step Dynamic Binding Model with Complex Allostery was applied to human samples obtained from randomized trials in men and women. It was found that over a wide range of testosterone concentrations prevalent in the male and female participants in the two testosterone trials, the free testosterone concentrations determined using the new algorithm were similar to those measured using the equilibrium dialysis. Also, the algorithm was applicable over a wide range of testosterone and estradiol concentrations in men and women. Without wishing to be bound by theory, there is a possibility that very high estrogen concentrations, such as those that may be observed during pregnancy, may affect testosterone binding to SHBG, introducing potential error in the calculated concentrations.

The current algorithm and the experimental data reported here were generated using wild type SHBG which is present in nearly 98% of Caucasians. Genome wide association studies have revealed several SHBG polymorphisms, two of which have been reported to affect testosterone binding to SHBG (28). Therefore, in future, the algorithms may include a term for the SHBG genotype. In summary, the experimental data of testosterone's association with SHBG implicate a complex allostery mechanism within the SHBG dimer. The new Multi-step Dynamic Binding Model with Complex Allostery provides excellent fit to the experimental data generated using three different techniques. Unlike the existing equations based on homogenous binding of testosterone with SHBG, which reveal systematic discrepancy from the values obtained by equilibrium dialysis, the free testosterone concentrations derived using the new model do not differ significantly from those measured using equilibrium dialysis.

References

1. Vermeulen A, Verdonck L & Kaufman J M (1999) A critical evaluation of simple methods for the estimation of free testosterone in serum. *J Clin Endocrinol Metab* 84(10): 3666-3672.
2. Rosner W, Auchus R J, Azziz R, Sluss P M & Raff H (2007) Position statement: Utility, limitations, and pitfalls in measuring testosterone: An endocrine society position statement. *J Clin Endocrinol Metab* 92(2): 405-413.

3. Rosner W (1997) Errors in the measurement of plasma free testosterone. *J Clin Endocrinol Metab* 82(6): 2014-2015.
4. Winters S J, Kelley D E & Goodpaster B (1998) The analog free testosterone assay: Are the results in men clinically useful?. *Clin Chem* 44(10): 2178-2182.
5. Sinha-Hikim I, et al (1998) The use of a sensitive equilibrium dialysis method for the measurement of free testosterone levels in healthy, cycling women and in human immunodeficiency virus-infected women. *J Clin Endocrinol Metab* 83(4): 1312-1318.
6. Van Uytfanghe K, et al (2004) Evaluation of a candidate reference measurement procedure for serum free testosterone based on ultrafiltration and isotope dilution-gas chromatography-mass spectrometry. *Clin Chem* 50(11): 2101-2110.
7. Adachi K, et al (1991) Measurement of plasma free steroids by direct radioimmunoassay of ultrafiltrate in association with the monitoring of free components with [14C]glucose. *Clin Chim Acta* 200(1): 13-22.
8. Morley J E, Patrick P & Perry H M, 3rd (2002) Evaluation of assays available to measure free testosterone. *Metabolism* 51(5): 554-559.
9. Morales A, Collier C P & Clark A F (2012) A critical appraisal of accuracy and cost of laboratory methodologies for the diagnosis of hypogonadism: The role of free testosterone assays. *Can J Urol* 19(3): 6314-6318.
10. Rosner W (1991) Plasma steroid-binding proteins. *Endocrinol Metab Clin North Am* 20(4): 697-720.
11. Rosner W (2006) Sex steroids and the free hormone hypothesis. *Cell* 124(3): 455-6; author reply 456-7.
12. Mendel C M (1989) The free hormone hypothesis: A physiologically based mathematical model. *Endocr Rev* 10(3): 232-274.
13. Sodergard R, Backstrom T, Shanbhag V & Carstensen H (1982) Calculation of free and bound fractions of testosterone and estradiol-17 beta to human plasma proteins at body temperature. *J Steroid Biochem* 16(6): 801-810.
14. Nanjee M N & Wheeler M J (1985) Plasma free testosterone—is an index sufficient?. *Ann Clin Biochem* 22 (Pt 4)(Pt 4): 387-390.
15. Ly L P & Handelsman D J (2005) Empirical estimation of free testosterone from testosterone and sex hormone-binding globulin immunoassays. *Eur J Endocrinol* 152 (3): 471-478.
16. Sartorius G, Ly L P, Sikaris K, McLachlan R & Handelsman D J (2009) Predictive accuracy and sources of variability in calculated free testosterone estimates. *Ann Clin Biochem* 46(Pt 2): 137-143.
17. Vermeulen A, Stoica T & Verdonck L (1971) The apparent free testosterone concentration, an index of androgenicity. *J Clin Endocrinol Metab* 33(5): 759-767.
18. Ly L P, et al (2010) Accuracy of calculated free testosterone formulae in men. *Clin Endocrinol (OxJ)* 73(3): 382-388.
19. Bhasin S, et al (2011) Reference ranges for testosterone in men generated using liquid chromatography tandem mass spectrometry in a community-based sample of healthy nonobese young men in the framingham heart study and applied to three geographically distinct cohorts. *J Clin Endocrinol Metab* 96(8): 2430-2439.
20. Spitzer M, et al (2012) Effect of testosterone replacement on response to sildenafil citrate in men with erectile dysfunction: A parallel, randomized trial. *Ann Intern Med* 157(10): 681-691.
21. Zakharov M N, Bhasin S, Szafran A T & Mancini M A, Jasuja R. (2011 (in press)) Numerical framework to model temporally-resolved multi-stage dynamic systems. *COMPUT METH PROG BIO*
22. Koshland D E, Jr, Nemethy G & Filmer D (1966) Comparison of experimental binding data and theoretical models in proteins containing subunits. *Biochemistry* 5(1): 365-385.
23. MONOD J, WYMAN J & CHANGEUX JP (1965) On the nature of allosteric transitions: A plausible model. *J Mol Biol* 12: 88-118.
24. Freiburger L A, et al (2011) Competing allosteric mechanisms modulate substrate binding in a dimeric enzyme. *Nat Struct Mol Biol* 18(3): 288-294.
25. Hilser V J & Thompson E B (2007) Intrinsic disorder as a mechanism to optimize allosteric coupling in proteins. *Proc Natl Acad Sci USA* 104(20): 8311-8315.
26. Avvakumov G V, Cherkasov A, Muller Y A & Hammond G L (2010) Structural analyses of sex hormone-binding globulin reveal novel ligands and function. *Mol Cell Endocrinol* 316(1): 13-23.
27. Awakumov G V, Muller Y A & Hammond G L (2000) Steroid-binding specificity of human sex hormone-binding globulin is influenced by occupancy of a zinc-binding site. *J Biol Chem* 275(34): 25920-25925.
28. Ohlsson C, et al (2011) Genetic determinants of serum testosterone concentrations in men. *PLoS Genet* 7(10): e1002313.

Example 2

A New Multi-step Dynamic Binding Model with Complex Allostery of Testosterone's Binding to Sex Hormone Binding Globulin Circulating free testosterone (FT) levels have been used widely in the diagnosis and treatment of hypogonadism in men. Due to experimental complexities in FT measurements, the Endocrine Society expert panel has recommended the use of calculated FT (cFT) as an appropriate approach for estimating FT. It is demonstrated herein that the prevailing model of testosterone's binding to SHBG, which assumes that each SHBG dimer binds two testosterone molecules and that the two binding sites on SHBG have similar binding affinity, provides values of free testosterone that differ substantially from those obtained using equilibrium dialysis.

Described herein is the characterization of testosterone's binding to SHBG using equilibrium dialysis (binding isotherms varying both ligand and protein) and isothermal titration calorimetry. These experimental data were utilized in the development of a new model of testosterone's binding to SHBG; and this new model permitted the determination of free testosterone concentrations and comparison of these values to those derived from equilibrium dialysis.

Experimental data from equilibrium dialysis experiments, and isothermal titration calorimetry provide evidence of complex homoallostery within SHBG. Described herein is a New Multi-Step Dynamic Binding Model with Complex Allostery encompassing at least two inter-converting microstates in unliganded SHBG, readjustment of equilibria between unliganded states upon binding of the first ligand molecule, and allosteric interaction between two binding sites of SHBG dimer Free testosterone concentrations determined using framework incorporating intra-dimer allostery did not differ from those measured using equilibrium dialysis in samples from clinical trials Testosterone's binding to SHBG is demonstrated herein to be a multi-step process that involves complex homo-allostery within SHBG dimer cFT values obtained using the new model have close correspondence with those measured using equilibrium dialysis.

Introduction

Testosterone, the major androgen in humans, circulates in blood bound largely to sex hormone binding globulin (SHBG) and albumin (Rosner 1991, Hammond and Bocchinfuso 1996, Bhasin et al 2010, Mendel 1989, Rosner et al 2007). Testosterone can also bind to orosomucoid and transcortin proteins, but the amount of testosterone bound to these proteins in human plasma is negligible. According to the free hormone hypothesis, only the unbound or free fraction can cross the plasma membrane and is biologically active (Rosner 1991, Hammond and Bocchinfuso 1996, Bhasin et al 2010, Mendel 1989, Rosner et al 2007). In many conditions that affect SHBG concentrations, such as obesity, diabetes, aging, hyperthyroidism, liver disease, and HIV-infection, total testosterone concentrations are altered because of changes in SHBG concentrations; in these conditions, expert panels have recommended determination of free testosterone (FT) concentration to obtain an accurate assessment of androgen status (Rosner 1991, Hammond and Bocchinfuso 1996, Bhasin et al 2010, Mendel 1989, Rosner et al 2007).

The current model of testosterone's binding to SHBG assumes that each SHBG dimer binds two testosterone molecules, and that each of the two binding sites on SHBG dimer has similar binding affinity. Equations to determine FT were proposed by Vermeulen and others (Rosner et al 2007, Sodergard et al 1982, Vermeulen et al 1971, Mazer 2009)(Sodergard et al 1982, Vermeulen et al 1971). We show here that the prevailing model of testosterone's binding to SHBG is erroneous. The data from equilibrium dialysis and isothermal titration calorimetry (ITC) experiments provide evidence for ligand modulated allosteric interaction between the binding sites on the two SHBG monomers.

Reflecting the growing interest in men's health and the success of pharmaceutical advertising, testosterone sales have grown from 23 million dollars in 1993 to 70 million in 2000 to 1.7 billion dollars in 2012 (Spitzer et al 2012). Testosterone is the second most frequently ordered test, next only to 25-hydroxyvitamin D. In 2012, nearly 4 million free testosterone tests were performed in the USA alone. A number of direct and indirect methods—equilibrium dialysis, ultrafiltration, tracer analog methods, and calculations based on homogenous (equal affinity of testosterone for each monomer in SHBG dimer) binding—have been developed for the determination of FT levels (Rosner et al 2007, Sodergard et al 1982, Vermeulen et al 1971, Mazer 2009, Rosner 1997, Winters et al 1998, Vermeulen et al 1999, Sinha-Hikim et al 1998, Van Uytfanghe et al 2004, Adachi et al 1991, Morley et al 2002)(Sodergard et al 1982, Vermeulen et al 1971). Expert panels have expressed concern about the accuracy and methodological complexity of the available assays for FT (Rosner et al 2007, Sodergard et al 1982, Vermeulen et al 1971). Recognizing these methodological difficulties in the measurement of free testosterone, the Endocrine Society's Expert Panel suggested that "the calculation of free testosterone from reliably measured total testosterone and SHBG using mass action equations provides the best approach for the estimation of free testosterone . . . " (Rosner et al 2007). Therefore, algorithms for calculating FT from total testosterone, SHBG and albumin concentrations have been used widely (Rosner et al 2007, Mazer 2009, Morley et al 2002, Morales et al 2012, Ly et al 2010, Sartorius et al 2009, Bhasin et al 2011, Ly and Handelsman 2005). The equations are either based on the binding mechanism and law of mass-action (Sodergard et al 1982, Mazer 2009, Vermeulen et al 1999)(Sodergard et al 1982, Vermeulen et al 1999, Sartorius et al 2009, Ly and Handelsman 2005, Nanjee and Wheeler 1985) or are empirically-derived (Ly et al 2010, Sartorius et al 2009, Ly and Handelsman 2005, Nanjee and Wheeler 1985)(Sodergard et al 1982, Sartorius et al 2009, Ly and Handelsman 2005, Nanjee and Wheeler 1985).

Described herein is equilibrium dialysis (varying both SHBG and ligand concentrations) and isothermal titration calorimetry (ITC) to characterize testosterone's binding to SHBG. Various possible mechanistic models of molecular interactions, including linear homogeneous binding of testosterone to SHBG as envisioned by Vermeulen (Vermeulen et al 1999), Sodergard (Sodergard et al 1982) and Mazer (Mazer 2009), and various allosteric mechanisms, including allostery with positive and negative cooperativity (Koshland et al 1966, MONOD et al 1965), and an ensemble allosteric mechanism (Hilser and Thompson 2007) were considered. Based on our analyses of the experimental data of testosterone's binding to SHBG, a novel algorithm was constructed for the calculation of FT, which included intra-dimer allostery, which provided the best fit to the totality of experimental data. This new model was applied to determine free testosterone concentrations in samples derived from randomized testosterone trials, the results compared with those obtained using equilibrium dialysis.

Materials and Methods

Biophysical characterization. Human SHBG purified from serum (Binding Site Group, Birmingham, UK) was characterized by protein gel denaturation-renaturation experiments and by measuring its ability to bind testosterone. Testosterone concentration in the SHBG stock solution, measured using LC-MS/MS, was undetectable. Testosterone standard 1.0 mg/mL±2% (3.47 mM) was obtained from Cerilliant (Round Rock, Tex.).

Binding profiles were established by the equilibrium dialysis (varying either ligand or protein concentration) were performed in 96-well dialysis plates containing dialysis chambers separated by membranes with 10 kDa cut-off (Harvard Apparatus, Holliston, Mass.). SHBG and testosterone were reconstituted in dialysis buffer (30 mM HEPES pH7.4, 90 mM NaCl, 1 mM $MgSO_4$, 187 μM $CaCl_2$), and mixed to a desired concentration. 200 μl of SHBG-testosterone mixture was loaded on one side of the dialysis membrane and dialyzed overnight against equal volume of dialysis buffer (2000. The equilibrium was achieved by rotating the dialysis plate overnight at 22° C. 16 hours were determined necessary to achieve an equilibrium. Each concentration/condition was tested in 3 different wells, and each titration was repeated at least 2 times.

Testosterone concentration was measured using liquid chromatography tandem mass spectrometry (LC-MS/MS) assay that has been certified by the Center for Disease Control and has a sensitivity of 2 ng/dL (Bhasin et al 2011).

Isothermal calorimetry (ITC) was performed using automated Auto-ITC200 calorimeter (MicroCal, Northampton, Mass.) at Biological calorimetry Facility (Huck Institutes of Life Sciences, University Park, Pa.). SHBG was reconstituted in 30 mM HEPES buffer, pH7.4, to a final concentration of 5 μM. Testosterone standard was prepared in DMSO and diluted in protein buffer to 100 μM in 5% DMSO. DMSO was added to SHBG by weight to match DMSO content in testosterone solution. Samples were degassed prior to loading to the calorimeter. Testosterone was injected into protein solution in 15 equal steps 2 μl each. Total reaction volume was 203 µl. Isothermal titration calorimetry experiment was repeated twice. Heat produced by each injection was measured by the calorimeter. Interval between injections was set at 240 seconds so that the temperature could return to baseline. The heat generated after each injection (after subtracting the heat of dilution of ligand in buffer) was integrated to produce calorimetric isotherm depicting the relation of the total heat generated in the reaction to testosterone-to-SHBG molar ratio.

Numerical Simulations of Allostery

Various molecular models of testosterone's binding to SHBG were numerically tested using LabVIEW™ (National Instruments, Austin, Tex.) toolkit (Zakharov et al 2012) (available on the world wide web at code.google.com/p/labview-biochemical-framework/). Parameter estimation for the models was performed as described previously (Zakharov et al 2012). Numerical correction for the equilibrium dialysis was incorporated as a part of every simulation model. Since some of the models and equations (Sodergard et al 1982, Vermeulen et al 1999, Nanjee and Wheeler 1985) were developed essentially before the confirmation of the 2 binding sites per SHBG dimer (Avvakumov et al 2001) we adjusted SHBG concentration by the factor of 2 for these models.

The fits of both types of binding profiles and ITC to various models were compared by calculating the residuals and $\chi^2$ values for each model. The fits to the model incorporating complex allostery consistently gave the smallest $\chi^2$ value and residuals.

Assessment of FT Concentrations in Clinical Trials. FT determined using the dynamic model developed in this study (cFTZBJ) and Vermeulen's equation (cFTV) (as implemented by Mazer, (Mazer 2009)) were compared with those measured using equilibrium dialysis in samples derived from randomized testosterone trials in men (Spitzer et al 2012) and women (Huang et al 2012). These samples had been collected in fasting state in the morning, stored at −80° C., and never thawed.

Testosterone in Men with Erectile Dysfunction (TED) Trial, whose results have been published (Spitzer et al 2012)(Spitzer et al 2012), was a randomized trial to determine whether addition of testosterone to an optimized regimen of sildenafil citrate is superior to placebo in improving erectile function in men with erectile dysfunction (ED) and low testosterone. At baseline and after 12-weeks of testosterone or placebo administration, total testosterone concentrations were measured using LC-MS/MS and SHBG concentrations using a two-site immunofluorometric assay (DELFIA®, Perkin-Elmer, Waltham, Mass.) (21). FT was measured in the same samples by equilibrium dialysis (Bhasin et al 2012).

Statistical Analysis.

The model fits of experimental data were assessed using chi-square statistics. For clinical trials data, the distributions of measured and calculated FT were derived for each of the relevant samples. Agreement between measured and calculated FT values was estimated using Deming (orthogonal) Regression, and Bland-Altman style plots were used to assess the difference between calculated and measured concentrations as a function of the measured concentration. Graphical depictions of association between FT, total testosterone, and SHBG were generated, with scatter plot smoothing using Generalized Additive Models with tensor product smooths (Wood 2006).

Results

Preliminary studies revealed that cFT values obtained using the Vermeulen's equation in samples derived from the TED Trial were significantly lower than those measured by equilibrium dialysis. To determine the molecular basis of this discrepancy, three experimental approaches were used to characterize testosterone's binding to SHBG: binding isotherms, ligand depletion curves, and isothermal titration calorimetry (ITC). The overview of different molecular models is presented below. Each of this models assume 2 binding sites per SHBG dimer.

The simplest of the SHBG T interaction models is Vemeulens model, assuming that each bindingsite interacts with T with the same affinity, regardless of the other binding site occupancy (FIG. 6, model A). The monomers are not interacting, therefore only one subunit is depicted. Second model is a model, when non-interacting monomers are allowed to have different affinities (FIG. 6, model B). Third and fourth models are models of positive and negative cooperativity as postulated by (Koshland et al 1966). Binding of the first testosterone molecule either facilitates (FIG. 6, model C) or supresses (FIG. 6, model D) binding of the second molecule (symmetric reactions are not listed for clarity). The sign of the cooperativity is modelled by the relation of the first equilibrium binding constant (Kd1) to the second one (Kd2). Kd1>Kd2 means positive cooperativity, Kd1<Kd2 means negative cooperativity. Model in FIG. 6 model E, the new Multi-step Dynamic Binding Model with Complex Allostery. The equilibrium between those states while unbound is governed by a unimolecular equilibrium constant Kd11. Upon binding of the first testosterone molecule (with equilibrium constants Kd1 and Kd2) SHBG dimer assumes two different states, each of them with different affinity for the second T molecule (Kd2 and Kd4). Consistent with the reported crystal structure of liganded SHBG (Grishkovskaya et al 2000, Grishkovskaya et al 1999, Grishkovskaya et al 2002, Avvakumov et al 2002), all models were constrained to eventually converge to a single double-liganded conformational state of SHBG dimer. These models were examined and the model with the best fit of the experimental data was determined.

Biophysical characterization of testosterone's binding to SHBG reveals evidence of complex homo-allostery within SHBG dimer.

Equilibrium Dialysis: Binding Isotherms

Figure 5A:
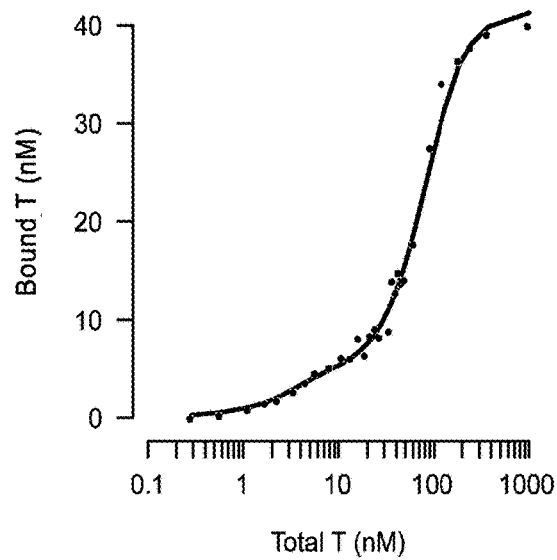
FIG. 5A depicts a graph of the binding isotherm. Graded concentrations of testosterone were incubated overnight with 20 nM SHBG and the amount of bound testosterone was plotted against total testosterone concentration. The fit curve represents the fit of data to the new Multi-step Dynamic Binding Model with Complex Allostery.
Figure 8A:
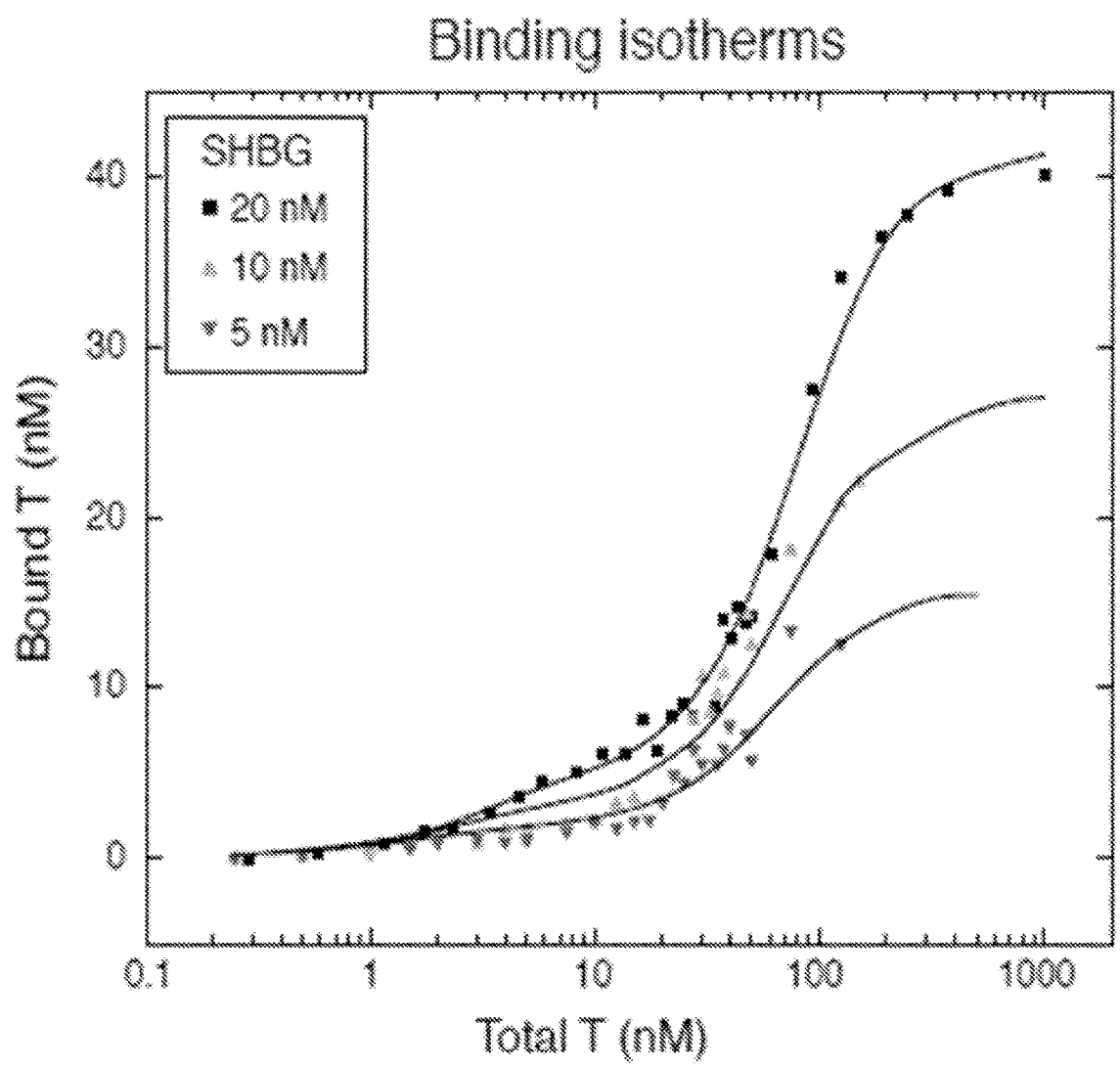
FIGS. 8A-8B demonstrate that the binding of testosterone to SHBG displays complex allostery.
Figure 8B:
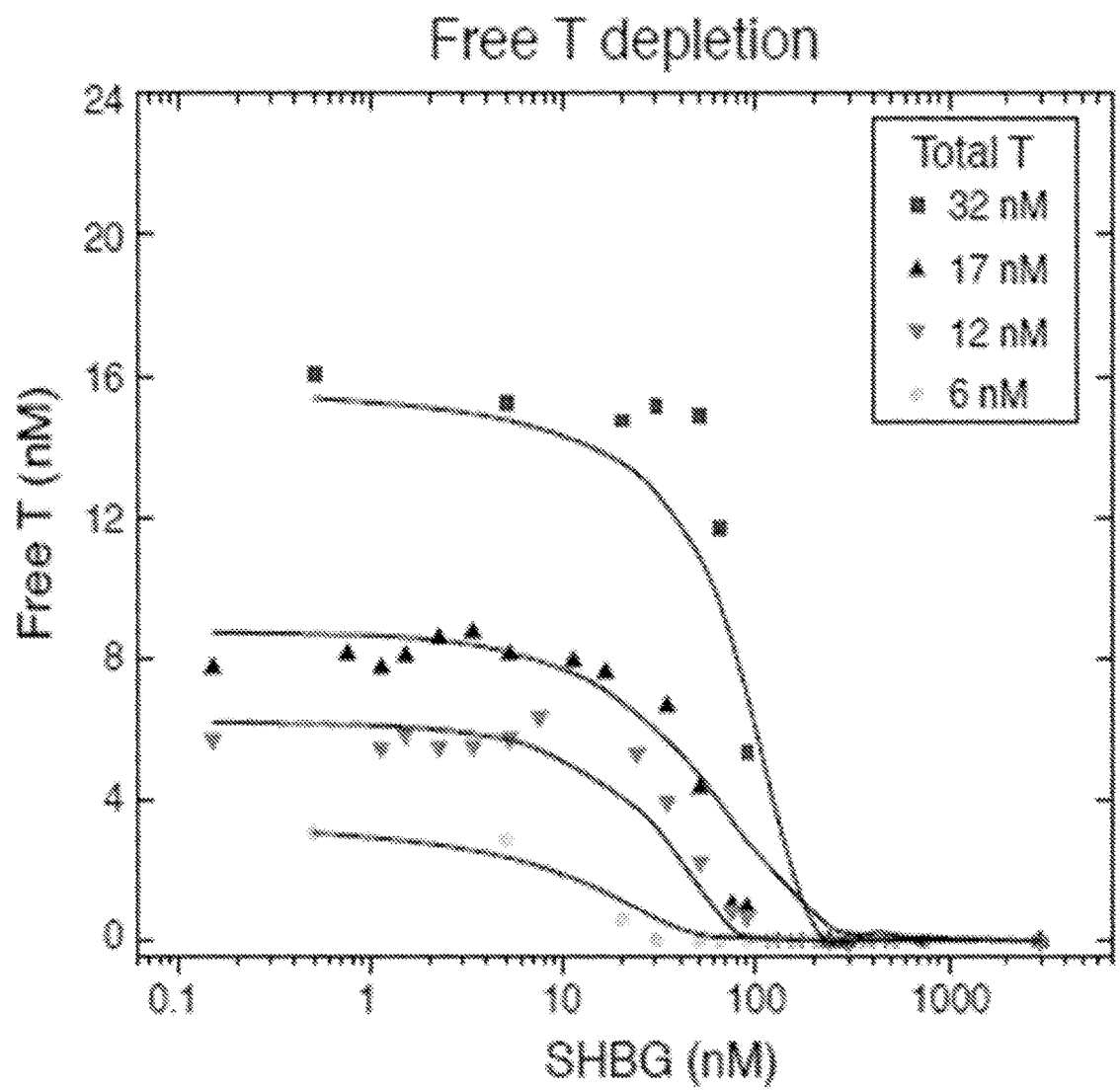
Figure 9A:
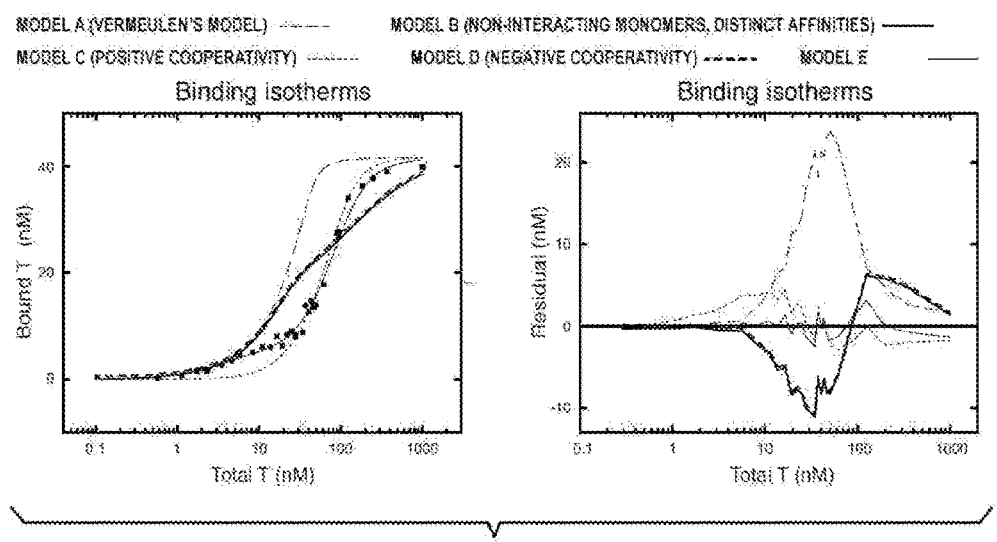
FIGS. 9A-9C depicts graphs depicting the fits of the various models of testosterone's binding to SHBG to the experimental data from binding isotherms, depletion experiments, and ITC. Left panels: The figures show the fits of data to the various models examined in this study. Right panels: The figures show corresponding residuals of the fit of data to various models of testosterone's binding to SHBG. Neither the Vermeulen's equation nor the simple allostery models adequately fit the experimental data from binding isotherms, depletion experiments, or ITC. The new Multi-step Dynamic Binding Model with Complex Allostery (model E) provided the optimal fit to the experimental data from all three methods.
Figure 9B:
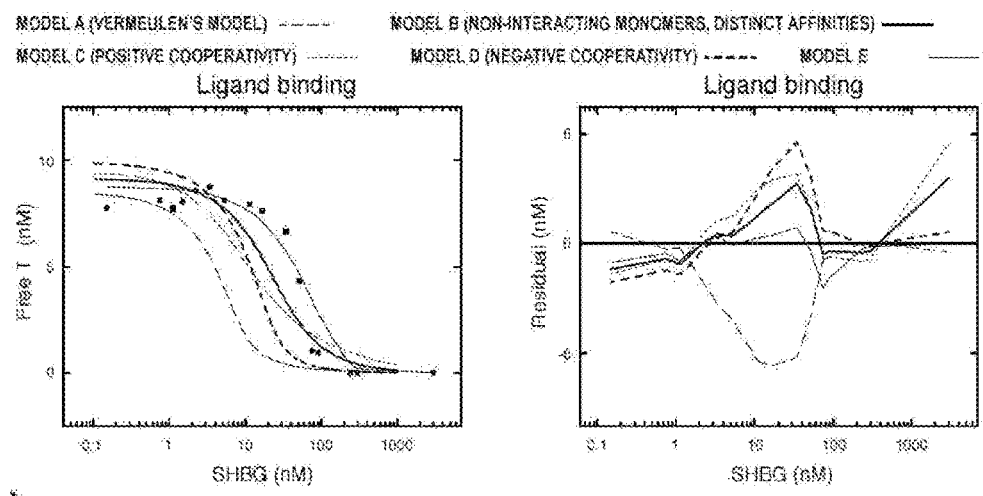
Figure 9C:
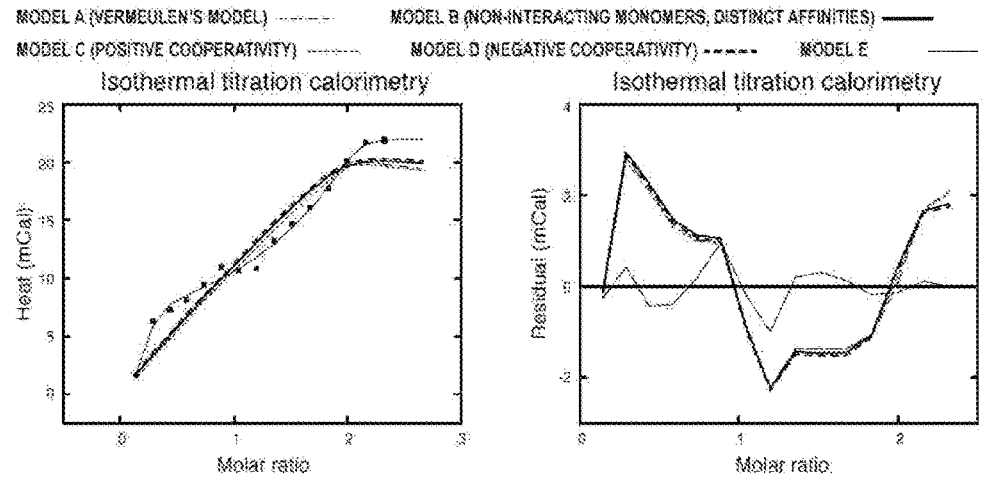

To generate the binding isotherms, 5, 10 or 20 nM SHBG (dimer) was incubated with graded concentrations of testosterone (0 to 400 nM) at 22° C., as described in the methods section. When bound testosterone concentration was plotted against total testosterone concentration (FIG. 5A, FIG. 8A), the binding isotherm displayed several characteristic features: two distinct saturation plateaus (including an apparent plateau at lower testosterone concentrations), asymmetry of the isotherm around the EC50 value. The relation of bound testosterone to total testosterone could not be adequately explained by Vermeulen's model. Only the new model eliciting intra-dimer allostery fit the binding isotherm optimally with the lowest $\chi^2$ (FIG. 8A) and explained the observed saturation plateaus, including the plateau at lower testosterone concentrations, and the asymmetry of binding isotherm around EC50. FIG. 5A presents the fit to the new Multi-step Dynamic Binding Model with Complex Allostery. Fits to other models of FIG. 6 as well as the analysis of the residuals is presented in supplementary material (FIG. 8A-8B). Additionally, it was tested if S*ST and S**S'T microstates were distinguishable. It was found that model with converged S*ST and S**S'T states failed to fit the data.

Equilibrium Dialysis: Testosterone Depletion Curves

As an independent assessment of testosterone's binding to SHBG, various amounts of SHBG (0.1 to 0.5 µM) were incubated with a fixed concentration of testosterone, and the depletion of unbound testosterone when increasing concentrations of SHBG were added was analyzed (FIG. 5B, FIGS. 9A-9C). These depletion curves were generated at various testosterone concentrations (3, 6, 8.7, and 16 nM). Sample preparation and measurement procedure are described in the Methods section. The relation of FT to SHBG concentration in depletion experiments was again best fit using the model that included complex allostery. The analysis of residuals (FIG. 8B) revealed that the optimal fit once again provided by the new Multi-step Dynamic Binding Model with Complex Allostery model.

Isothermal Titration Calorimetry (ITC):

To validate the new model further and to evaluate the thermodynamic parameters associated with testosterone's binding to SHBG, the heat produced as progressively larger amounts of testosterone bind to SHBG, were measured using the ITC. The ITC data has a characteristic shoulder (FIG. 5C) and cannot be described as a simple sigmoidal curve predicted by Vermeulen's model (FIG. 8A-8B). Using the computational framework developed in LabVIEW (Zakharov et al 2012), we generated the fits of the ITC data (For mathematical treatment, see supplementary material 51, which follows (Freiburger et al 2011)). The shape of ITC curve can be explained as a convoluted result of testosterone's binding and multiple conformational rearrangements defined by the comprehensive model incorporating allostery. Model constants obtained as a result of linked fit in FIGS. 5A and 5B were used as a starting point for the fit; enthalpies and reaction constants computed from the fit ITC data are presented in FIG. 7. While we used an independent enthalpy parameter for each reaction in the model, they are not simultaneously identifiable.

Effects of Estradiol and Dihydrotestosterone (DHT). Addition of estradiol 17β in concentrations ranging from 10 to 500 pg/mL had no significant effect on percent free testosterone. Similarly, free testosterone concentrations in men treated with graded doses of testosterone enanthate plus placebo whose DHT concentrations extended from physiologic to supraphysiologic range did not differ from those treated with testosterone enanthate plus dutasteride whose DHT concentrations were very low (Bhasin et al 2012), indicating that DHT over the range of concentrations relevant in male and female physiology has little effect on percent free testosterone.

Application of new Multi-step Dynamic Binding Model with Complex Allostery to Clinical Trials Data. SHBG and albumin are predominantly the two proteins that bind testosterone with significant affinity; the binding affinities of transcortin and orosomucoid for testosterone are extremely low. Accordingly, we included testosterone's interaction with albumin along with complex allostery in equilibria describing its binding to SHBG to determine FT (FTZBJ) in serum samples from the Testosterone in Erectile Dysfunction (TED) Trial ((Spitzer et al 2012). The comprehensive model was implemented in the LabVIEW framework (Zakharov et al 2012) (data not shown).

cFTV significantly underestimated FT levels relative to equilibrium dialysis in men participating in the TED trial. In contrast, cFTZBJ provided values that were not statistically different from those measured by equilibrium dialysis in men (slope 1.01±0.01). The Bland-Altman plots (data not shown) found no significant difference between the cFTZBJ and those obtained using equilibrium dialysis in either men or women; the relative deviation of values calculated using the new model from those measured using equilibrium dialysis was evenly distributed around 0, likely reflecting multiple sources of measurement error in testosterone assay, SHBG assay, and equilibrium dialysis. The Deming regression was used to compare the values derived using the new model and cFTv with those obtained using equilibrium dialysis, which reaffirm the substantial bias of FTv from values derived using equlibirum dialysis and the substantially better correspondence between cFTZBJ and equilibrium dialysis.

Relation between Percent FT with Total Testosterone and SHBG. Intra-dimer complex allostery suggests that SHBG can regulate FT fraction over a wide range of total testosterone concentrations without getting saturated. Indeed, it was found that percent FT calculated using the new model changed very modestly over a wide range of total testosterone concentrations. In contrast, the Vermeulen's equation suggests a negative relation between percent FT and total testosterone. Furthermore, as SHBG concentrations increase, percent FT calculated using our new model shows only a modest decline in contrast to the marked decline in percent FT calculated using Vermeulen's equation.

Discussion

Figure 7:
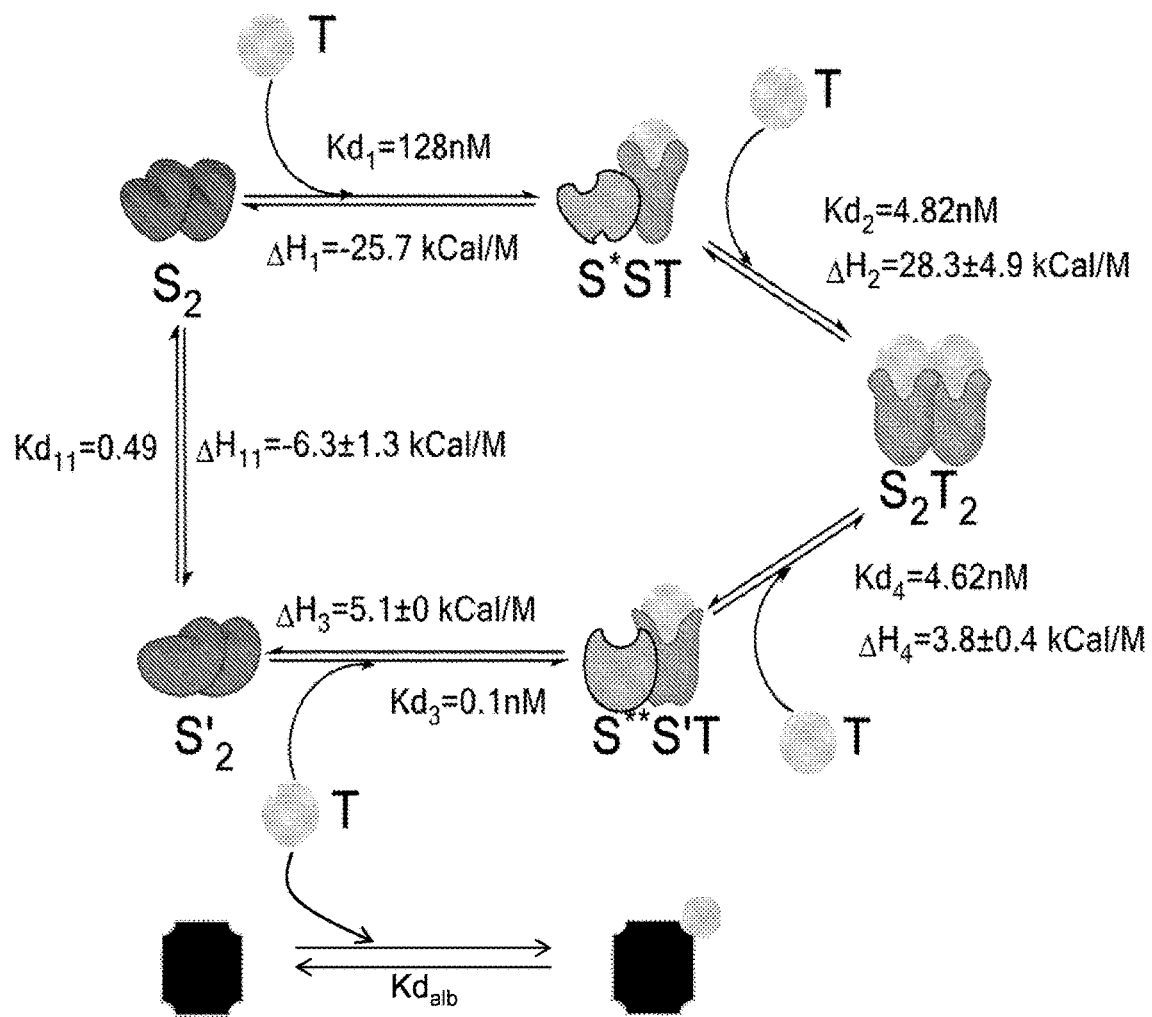
FIG. 7 depicts the thermodynamic Parameters associated with testosterone's binding to SHBG derived from the fit of binding isotherms and ITC data to new model. While this parameter set is not unique, together they consistently describe the binding isotherms, depletion curves and ITC data to the new Multi-step Dynamic Binding Model with Complex Allostery developed in this study. These were utilized to obtain FT values ($cFT_{ZBJ}$) in samples obtained in clinical trials.

Several lines of evidence presented here indicate that the existing model of testosterone's binding to SHBG (single binding site or two identical, non-interacting binding sites on SHBG) that has formed the basis of Vermeulen, Sodergard, and Mazer's (Sodergard et al 1982, Vermeulen et al 1971, Mazer 2009, Vermeulen et al 1999) equations to estimate free testosterone concentrations does not accurately explain the experimental data from equilibrium dialysis and and ITC (even if corrected for 2 binding sites per dimer stoichiometry). While the discrepancy between testosterone concentrations estimated using the above-mentioned equations and those measured using equilibrium dialysis has been recognized (Ly et al 2010), the data presented herein provide a mechanistic explanation for this discrepancy. Simple models of homotropic allostery with positive or negative cooperativity within a dimer also did not adequately explain the experimental data. Only the dynamic model that incorporates complex allostery optimally fits the experimental data derived from three independent methods. Furthermore, FT concentrations calculated using the new model incorporating complex allostery were not significantly different from those measured by equilibrium dialysis in samples derived from men and women in two separate clinical trials. The analysis of the steady state experimental binding data presented herein indicate that in the absence of testosterone, SHBG molecule can assume one of at least two inter-converting microstates in dynamic equilibrium. The binding of testosterone to one of the monomers of the SHBG dimer in a given microstate affects the interaction of testosterone with the unoccupied second binding site on the SHBG dimer. The model suggests a dynamic re-adjustment of populations of intermediate species as testosterone concentration is changing. Because of the dynamic nature of these processes, all parameters of the model cannot be uniquely determined Thus, testosterone's binding to SHBG is not a single linear reaction but rather a series of interrelated molecular processes that can be described by the new Multi-step Dynamic Binding Model with Complex Allostery shown in FIG. 7. The fits of the data to the new model that incorporates complex allostery display a dynamic re-adjustment of populations of intermediate species as testosterone concentration changes. Because of the multiple equilibria and dynamic and allosteric nature of these processes, testosterone's binding to SHBG cannot be described as a simple linear equation of ligand binding equilibrium. Accordingly, the multi-species allostery model was implemented in LabVIEW framework (Zakharov et al 2012). Optimal fit parameters for the ITC and equilibrium dialysis data (sections 3.1.1, 3.1.2, 3.1.3) were obtained by the Levenberg-Marquardt optimization, using globalfit approach similar to (Freiburger et al 2011). This set of parameters that can be used to compute free testosterone are shown in FIGS. 7 and 6, model E.

The new dynamic model leads to the reconsideration of several dogmas related to testosterone's binding to SHBG and has important physiologic and clinical implications. First, the fraction of circulating testosterone which is free is substantially greater (2.9±0.4%) than has been generally assumed (% cFTV 1.5±0.4%). Second, percent FT is not significantly related to total testosterone over a wide range of total testosterone concentrations. However, the percent FT declines as SHBG concentrations increase, although it does not decline as precipitously as predicted by the Vermeulen's model. Due to the allostery between the two binding sites, SHBG is able to regulate FT levels in much larger dynamic range.

Several factors may have contributed to the formulation of the prevailing hypothesis that monomers within SHBG dimer display identical binding affinity without any dynamic interaction between the monomers. The extant ligand binding equations were formulated in an era that preceded the appreciation of the dimeric nature of circulating SHBG. However, the Mazer's implementation (Mazer 2009) of the Vermeulen's model, as applied in these analyses used the correct stoichiometry—two molecules of testosterone binding to each SHBG dimer Therefore, the discrepancy between cFTv and the reference method cannot be explained solely on the basis of incorrect stoichiometry. Furthermore, the range of testosterone and SHBG concentrations used in binding experiments and Scatchard plots were limited and did not generally extend into the high range (Metzger et al 2003, Dunn et al 1981, Hauptmann et al 2003, Petra et al 1986), which may have prevented appreciation of the second binding site. Also, a single crystal structure of the ligand-bound SHBG may have further contributed to the erroneous impression that the binding events associated with testosterone's binding to two binding sites on SHBG dimer are identical. The inability to resolve the unliganded SHBG structure (Avvakumov et al 2000, Avvakumov et al 2010) (Avvakumov et al 2010) as well as the increased stability of SHBG upon ligand binding (Avvakumov et al 2000)(Avvakumov et al 2000) may be related to significant rearrangement of SHBG molecule upon binding of the first ligand, as predicted by the conformational heterogeneity in complex allostery. The additional energy barrier that SHBG has to overcome may result in altered affinity for binding of the second ligand molecule.

While the new algorithm developed in this study accurately determines FT, effects of other interacting hormones mandates further investigation. In a previous study (Bhasin et al 2012), it was found that free testosterone concentrations in men treated with graded doses of testosterone enanthate plus placebo whose DHT concentrations extended from physiologic to supraphysiologic range did not differ from those treated with testosterone enanthate plus dutasteride whose DHT concentrations were very low, indicating that DHT over the range of concentrations relevant in in male and female physiology has little effect on percent free testosterone. Similarly, over a wide range of estradiol concentrations prevalent in men and women, cFTZBJ concentrations were similar to those measured using equilibrium dialysis. Without wishing to be bound by theory, very high estrogen concentrations, such as those observed during pregnancy, or very high DHT concentrations could affect testosterone's binding to SHBG.

Transcortin and orosomucoid display very low affinity for SHBG; their role in regulating free testosterone was not assessed in this investigation and needs further clarity; it is remarkable that FT concentrations derived using the new dynamic model were not significantly different from those determined by equilibrium dialysis in randomized trials even though inter-individual differences in transcortin, and orosomucoid were not considered, consistent with the view that these proteins play a minor role in regulating free testosterone in healthy men and women.

The current algorithm and the experimental data were generated using wild type SHBG which is present in nearly 98% of Caucasians. Genome wide association studies have revealed several SHBG polymorphisms, two of which affect testosterone's binding to SHBG (Ohlsson et al 2011)(Ohlsson et al 2011). Therefore, in future, the algorithm may include a term for SHBG genotype. Additional research is needed to extend the model to incorporate SHBG polymorphisms that affect testosterone's binding to SHBG.

In summary, experimental data generated using several independent methods provide evidence of an complex allostery mechanism of testosterone binding to SHBG dimer FT concentrations derived using the new dynamic model incorporating complex allostery do not differ significantly from those measured using equilibrium dialysis. The application of the new dynamic model to clinical trials data have revealed new insights into the percent of circulating testosterone that is free, the relation between percent FT and total testosterone and SHBG. The use of additional experimental models, including dimerization-deficient SHBG mutants, would allow further characterization of testosterone's interaction with SHBG to validate the complex allostery as suggested by this study. The validation of the new dynamic model incorporating complex allostery should also be further explored in clinical populations as its availability on desktops and mobile devices can provide a convenient and accurate approach for determining FT at the point-of-care, and facilitating the diagnosis and treatment of men and women with androgen disorders.

References:

Adachi, K., Yasuda, K., Fuwa, Y., Goshima, E., Yamakita, N., Miura, K., 1991. Measurement of plasma free steroids by direct radioimmunoassay of ultrafiltrate in association with the monitoring of free components with [14C]glucose. Clin. Chim Acta 200, 13-22.

Avvakumov, G. V., Cherkasov, A., Muller, Y. A., Hammond, G. L., 2010. Structural analyses of sex hormone-binding globulin reveal novel ligands and function. Mol. Cell. Endocrinol. 316, 13-23.

Avvakumov, G. V., Grishkovskaya, I., Muller, Y. A., Hammond, G. L., 2002. Crystal structure of human sex hormone-binding globulin in complex with 2-methoxyestradiol reveals the molecular basis for high affinity interactions with C-2 derivatives of estradiol. J. Biol. Chem. 277, 45219-45225.

Avvakumov, G. V., Grishkovskaya, I., Muller, Y. A., Hammond, G. L., 2001. Resolution of the human sex hormone-binding globulin dimer interface and evidence for two steroid-binding sites per homodimer J Biol. Chem. 276, 34453-34457.

Avvakumov, G. V., Muller, Y. A., Hammond, G. L., 2000. Steroid-binding specificity of human sex hormone-binding globulin is influenced by occupancy of a zinc-binding site. J. Biol. Chem. 275, 25920-25925.

Bhasin, S., Cunningham, G. R., Hayes, F. J., Matsumoto, A. M., Snyder, P. J., Swerdloff, R. S., Montori, V. M., Task Force, E. S., 2010. Testosterone therapy in men with androgen deficiency syndromes: an Endocrine Society clinical practice guideline. J. Clin. Endocrinol. Metab. 95, 2536-2559.

Bhasin, S., Pencina, M., Jasuj a, G. K., Travison, T. G., Coviello, A., Orwoll, E., Wang, P. Y., Nielson, C., Wu, F., Tajar, A., Labrie, F., Vesper, H., Zhang, A., Ulloor, J., Singh, R., D'Agostino, R., Vasan, R. S., 2011. Reference ranges for testosterone in men generated using liquid chromatography tandem mass spectrometry in a community-based sample of healthy nonobese young men in the framingham heart study and applied to three geographically distinct cohorts. J. Clin. Endocrinol. Metab. 96, 2430-2439.

Bhasin, S., Travison, T. G., Storer, T. W., Lakshman, K., Kaushik, M., Mazer, N. A., Ngyuen, A. H., Davda, M. N., Jara, H., Aakil, A., Anderson, S., Knapp, P. E., Hanka, S., Mohammed, N., Daou, P., Miciek, R., Ulloor, J., Zhang, A., Brooks, B., Orwoll, K., Hede-Brierley, L., Eder, R., Elmi, A., Bhasin, G., Collins, L., Singh, R., Basaria, S., 2012. Effect of testosterone supplementation with and without a dual 5alpha-reductase inhibitor on fat-free mass in men with suppressed testosterone production: a randomized controlled trial. JAMA 307, 931-939.

Dunn, J. F., Nisula, B. C., Rodbard, D., 1981. Transport of steroid hormones: binding of 21 endogenous steroids to both testosterone-binding globulin and corticosteroid-binding globulin in human plasma. J. Clin. Endocrinol. Metab. 53, 58-68.

Elveback, L., 1973. The population of healthy persons as a source of reference information. Hum. Pathol. 4, 9-16.

Freiburger, L. A., Baettig, O. M., Sprules, T., Berghuis, A. M., Auclair, K., Mittermaier, A. K., 2011. Competing allosteric mechanisms modulate substrate binding in a dimeric enzyme. Nat. Struct. Mol. Biol. 18, 288-294.

Grishkovskaya, I., Avvakumov, G. V., Hammond, G. L., Catalano, M. G., Muller, Y. A., 2002. Steroid ligands bind human sex hormone-binding globulin in specific orientations and produce distinct changes in protein conformation. J. Biol. Chem. 277, 32086-32093.

Grishkovskaya, I., Avvakumov, G. V., Sklenar, G., Dales, D., Hammond, G. L., Muller, Y. A., 2000. Crystal structure of human sex hormone-binding globulin: steroid transport by a laminin G-like domain. EMBO J. 19, 504-512.

Grishkovskaya, I., Sklenar, G., Avvakumov, G. V., Dales, D., Behlke, J., Hammond, G. L., Muller, Y. A., 1999. Crystallization of the N-terminal domain of human sex hormone-binding globulin, the major sex steroid carrier in blood. Acta Crystallogr. D Biol. Crystallogr. 55, 2053-2055.

Hammond, G. L., Bocchinfuso, W. P., 1996. Sex hormone-binding globulin: gene organization and structure/function analyses. Horm. Res. 45, 197-201.

Hauptmann, H., Metzger, J., Schnitzbauer, A., Cuilleron, C. Y., Mappus, E., Luppa, P. B., 2003. Syntheses and ligand-binding studies of 1 alpha- and 17 alpha-aminoalkyl dihydrotestosterone derivatives to human sex hormone-binding globulin. Steroids 68, 629-639.

Hilser, V. J., Thompson, E. B., 2007. Intrinsic disorder as a mechanism to optimize allosteric coupling in proteins. Proc. Natl. Acad. Sci. U.S.A 104, 8311-8315.

Huang, G., Basaria, S., Travison, T., Ho, M., Davda, M., Mazer, N., Knapp, P., Collins, L., Ursion, M., Zhang, A., Ulloor, J., Storer, T., Bhasin, S., 2012. Testosterone dose response in surgically menopausal women. The Endocrine Society Meeting June.

Koshland, D. E., Jr, Nemethy, G., Filmer, D., 1966. Comparison of experimental binding data and theoretical models in proteins containing subunits. Biochemistry 5, 365-385.

Krasnoff, J. B., Basaria, S., Pencina, M. J., Jasuja, G. K., Vasan, R. S., Ulloor, J., Zhang, A., Coviello, A., Kelly-Hayes, M., D'Agostino, R. B., Wolf, P. A., Bhasin, S., Murabito, J. M., 2010. Free testosterone levels are associated with mobility limitation and physical performance in community-dwelling men: the Framingham Offspring Study. J. Clin. Endocrinol. Metab. 95, 2790-2799.

Lee, D. M., O'Neill, T. W., Pye, S. R., Silman, A. J., Finn, J. D., Pendleton, N., Tajar, A., Bartfai, G., Casanueva, F., Forti, G., Giwercman, A., Huhtaniemi, I. T., Kula, K., Punab, M., Boonen, S., Vanderschueren, D., Wu, F. C., EMAS study group, 2009. The European Male Ageing Study (EMAS): design, methods and recruitment. Int. J. Androl. 32, 11-24.

Ly, L. P., Handelsman, D. J., 2005. Empirical estimation of free testosterone from testosterone and sex hormone-binding globulin immunoassays. Eur. J. Endocrinol. 152, 471-478.

Ly, L. P., Sartorius, G., Hull, L., Leung, A., Swerdloff, R. S., Wang, C., Handelsman, D. J., 2010. Accuracy of calculated free testosterone formulae in men. Clin. Endocrinol. (Oxf) 73, 382-388.

Mazer, N. A., 2009. A novel spreadsheet method for calculating the free serum concentrations of testosterone, dihydrotestosterone, estradiol, estrone and cortisol: with illustrative examples from male and female populations. Steroids 74, 512-519.

Mendel, C. M., 1989. The free hormone hypothesis: a physiologically based mathematical model. Endocr. Rev. 10, 232-274.

Metzger, J., Schnitzbauer, A., Meyer, M., Soder, M., Cuilleron, C. Y., Hauptmann, H., Huber, E., Luppa, P. B., 2003. Binding analysis of 1 alpha- and 17alpha-dihydrotestosterone derivatives to homodimeric sex hormone-binding globulin. Biochemistry 42, 13735-13745.

MONOD, J., WYMAN, J., CHANGEUX, J. P., 1965. On the Nature of Allosteric Transitions: a Plausible Model. J. Mol. Biol. 12, 88-118.

Morales, A., Collier, C. P., Clark, A. F., 2012. A critical appraisal of accuracy and cost of laboratory methodologies for the diagnosis of hypogonadism: the role of free testosterone assays. Can. J. Urol. 19, 6314-6318.

Morley, J. E., Patrick, P., Perry, H. M., 3rd, 2002. Evaluation of assays available to measure free testosterone. Metabolism 51, 554-559.

Nanjee, M. N., Wheeler, M. J., 1985. Plasma free testosterone—is an index sufficient? Ann. Clin. Biochem. 22 (Pt 4), 387-390.

Ohlsson, C., Wallaschofski, H., Lunetta, K. L., Stolk, L., Perry, J. R., Koster, A., Petersen, A. K., Eriksson, J., Lehtimaki, T., Huhtaniemi, I. T., Hammond, G. L., Maggio, M., Coviello, A. D., EMAS Study Group, Ferrucci, L., Heier, M., Hofman, A., Holliday, K. L., Jansson, J. O., Kahonen, M., Karasik, D., Karlsson, M. K., Kiel, D. P., Liu, Y., Ljunggren, O., Lorentzon, M., Lyytikainen, L. P., Meitinger, T., Mellstrom, D., Melzer, D., Miljkovic, I., Nauck, M., Nilsson, M., Penninx, B., Pye, S. R., Vasan, R. S., Reincke, M., Rivadeneira, F., Tajar, A., Teumer, A., Uitterlinden, A. G., Ulloor, J., Viikari, J., Volker, U., Volzke, H., Wichmann, H. E., Wu, T. S., Zhuang, W. V., Ziv, E., Wu, F. C., Raitakari, O., Eriksson, A., Bidlingmaier, M., Harris, T. B., Murray, A., de Jong, F. H., Murabito, J. M., Bhasin, S., Vandenput, L., Haring, R., 2011. Genetic determinants of serum testosterone concentrations in men. PLoS Genet. 7, e1002313.

Petra, P. H., Namkung, P. C., Senear, D. F., McCrae, D. A., Rousslang, K. W., Teller, D. C., Ross, J. B., 1986. Molecular characterization of the sex steroid binding protein (SBP) of plasma. Re-examination of rabbit SBP and comparison with the human, macaque and baboon proteins. J. Steroid Biochem. 25, 191-200.

Rosner, W., 1997. Errors in the measurement of plasma free testosterone. J. Clin. Endocrinol. Metab. 82, 2014-2015.

Rosner, W., 1991. Plasma steroid-binding proteins. Endocrinol. Metab. Clin. North Am. 20, 697-720.

Rosner, W., Auchus, R. J., Azziz, R., Sluss, P. M., Raff, H., 2007. Position statement: Utility, limitations, and pitfalls in measuring testosterone: an Endocrine Society position statement. J. Clin. Endocrinol. Metab. 92, 405-413.

Sartorius, G., Ly, L. P., Sikaris, K., McLachlan, R., Handelsman, D. J., 2009. Predictive accuracy and sources of variability in calculated free testosterone estimates. Ann. Clin. Biochem. 46, 137-143.

Sinha-Hikim, I., Arver, S., Beall, G., Shen, R., Guerrero, M., Sattler, F., Shikuma, C., Nelson, J. C., Landgren, B. M., Mazer, N. A., Bhasin, S., 1998. The use of a sensitive equilibrium dialysis method for the measurement of free testosterone levels in healthy, cycling women and in human immunodeficiency virus-infected women. J. Clin. Endocrinol. Metab. 83, 1312-1318.

Sodergard, R., Backstrom, T., Shanbhag, V., Carstensen, H., 1982. Calculation of free and bound fractions of testosterone and estradiol-17 beta to human plasma proteins at body temperature. J. Steroid Biochem. 16, 801-810.

Solberg, H. E., 1987. International Federation of Clinical Chemistry (IFCC), Scientific Committee, Clinical Section, Expert Panel on Theory of Reference Values, and International Committee for Standardization in Haematology (ICSH), Standing Committee on Reference Values. Approved Recommendation (1986) on the theory of reference values. Part 1. The concept of reference values. J. Clin. Chem. Clin. Biochem. 25, 337-342.

Spitzer, M., Basaria, S., Travison, T. G., Davda, M. N., Paley, A., Cohen, B., Mazer, N. A., Knapp, P. E., Hanka, S., Lakshman, K. M., Ulloor, J., Zhang, A., Orwoll, K., Eder, R., Collins, L., Mohammed, N., Rosen, R. C., DeRogatis, L., Bhasin, S., 2012. Effect of testosterone replacement on response to sildenafil citrate in men with erectile dysfunction: a parallel, randomized trial. Ann. Intern. Med. 157, 681-691.

Splansky, G. L., Corey, D., Yang, Q., Atwood, L. D., Cupples, L. A., Benjamin, E. J., D'Agostino R B, S., Fox, C. S., Larson, M. G., Murabito, J. M., O'Donnell, C. J., Vasan, R. S., Wolf, P. A., Levy, D., 2007. The Third Generation Cohort of the National Heart, Lung, and Blood Institute's Framingham Heart Study: design, recruitment, and initial examination. Am. J. Epidemiol. 165, 1328-1335. Tajar, A., Forti, G., O'Neill, T. W., Lee, D. M., Silman, A. J., Finn, J. D., Bartfai, G., Boonen, S., Casanueva, F. F., Giwercman, A., Han, T. S., Kula, K., Labrie, F., Lean, M. E., Pendleton, N., Punab, M., Vanderschueren, D., Huhtaniemi, I. T., Wu, F. C., EMAS Group, 2010. Characteristics of secondary, primary, and compensated hypogonadism in aging men: evidence from the European Male Ageing Study. J. Clin. Endocrinol. Metab. 95, 1810-1818.

Van Uytfanghe, K., Stockl, D., Kaufman, J. M., Fiers, T., Ross, H. A., De Leenheer, A. P., Thienpont, L. M., 2004. Evaluation of a candidate reference measurement procedure for serum free testosterone based on ultrafiltration and isotope dilution-gas chromatography-mass spectrometry. Clin. Chem. 50, 2101-2110.

Vermeulen, A., Stoica, T., Verdonck, L., 1971. The apparent free testosterone concentration, an index of androgenicity. J. Clin. Endocrinol. Metab. 33, 759-767.

Vermeulen, A., Verdonck, L., Kaufman, J. M., 1999. A critical evaluation of simple methods for the estimation of free testosterone in serum. J. Clin. Endocrinol. Metab. 84, 3666-3672.

Winters, S. J., Kelley, D. E., Goodpaster, B., 1998. The analog free testosterone assay: are the results in men clinically useful? Clin. Chem. 44, 2178-2182.

Wood, S. N., 2006. Generalized Additive Models: An Introduction with R, pp. 391, Chapman & Hall/CRC, Boca Raton, Fla.

Wu, F. C., Tajar, A., Beynon, J. M., Pye, S. R., Silman, A. J., Finn, J. D., O'Neill, T. W., Bartfai, G., Casanueva, F. F., Forti, G., Giwercman, A., Han, T. S., Kula, K., Lean, M. E., Pendleton, N., Punab, M., Boonen, S., Vanderschueren, D., Labrie, F., Huhtaniemi, I. T., EMAS Group, 2010. Identification of late-onset hypogonadism in middle-aged and elderly men. N. Engl. J. Med. 363, 123-135.

Zakharov, M. N., Bhasin, S., Szafran, A. T., Mancini, M. A., Jasuja, R., 2012. Numerical framework to model temporally resolved multi-stage dynamic systems. Comput. Methods Programs Biomed. 108, 750-759.

Example 3

Figure 10:
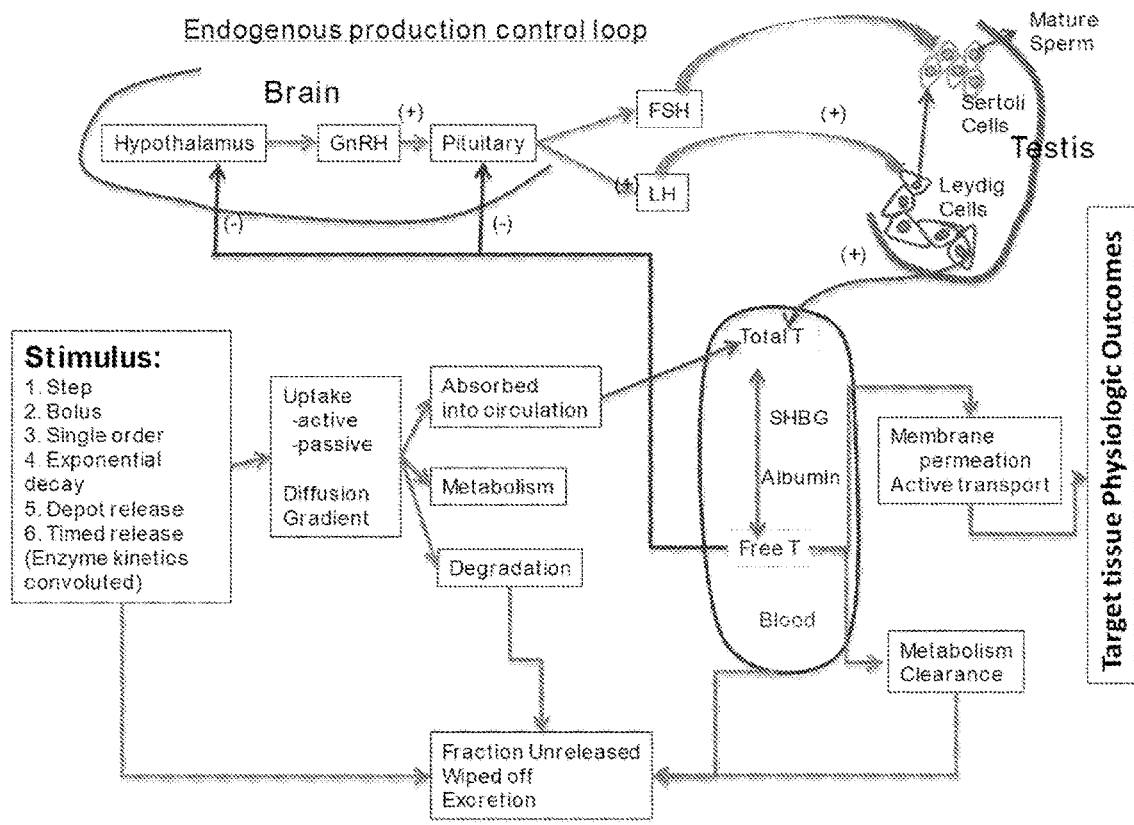
FIG. 10 depicts a schematic of the control of testosterone levels.
Figure 11:
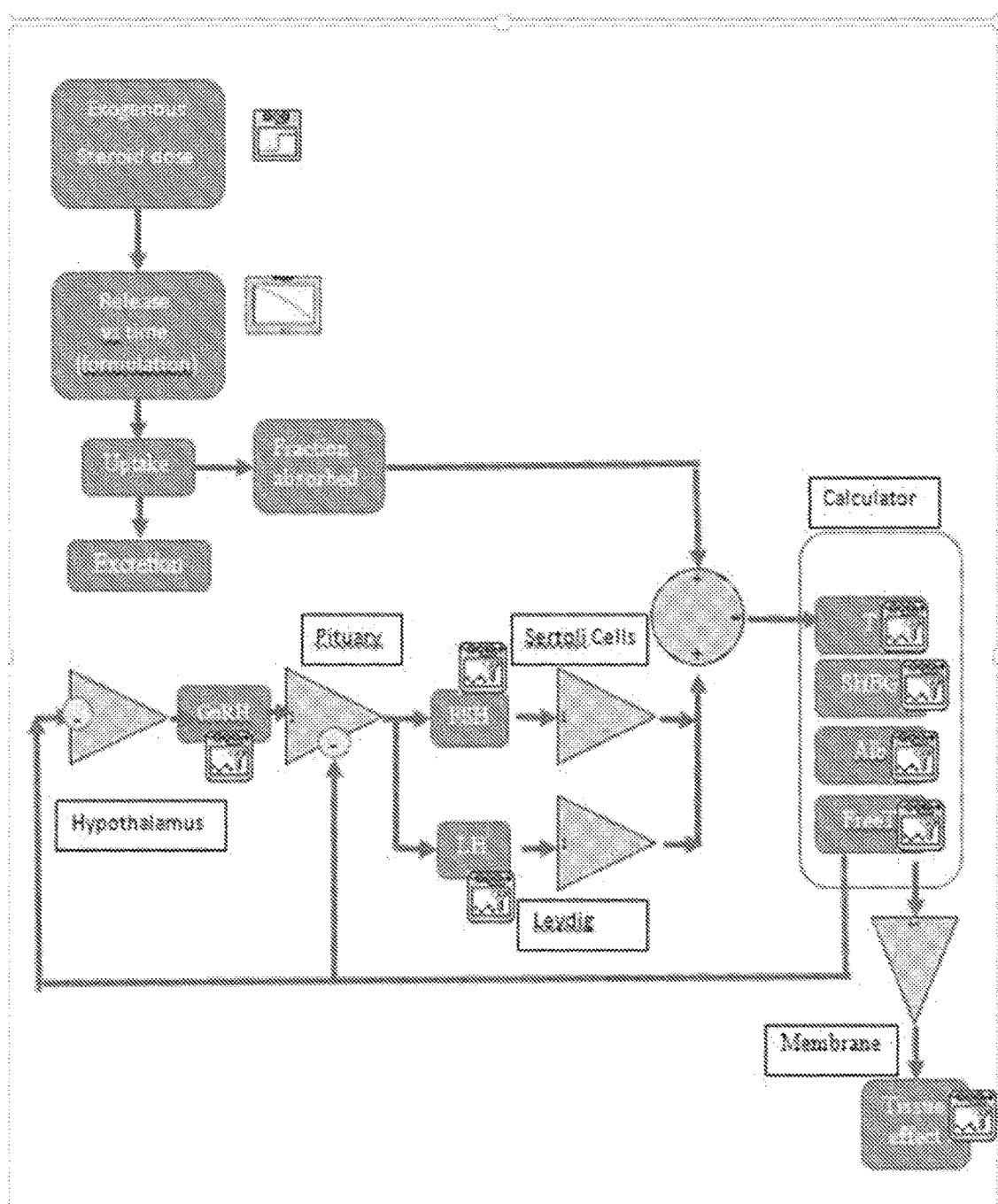
FIG. 11 depicts a schematic of an exemplary system of determining free testosterone levels and/or dosages.

In one aspect, described herein is a personalized exogenous steroid delivery dosimeter. Time dependent drug delivery/clearance models can be incorporated with the calculator of free T described herein (FIG. 10). T administration, redistribution, and clearance rates can be accounted for. In some embodiments, an experiment, a model, and set of parameters are present and the model described herein can be used to obtain results. In some embodiments, a set of datasets and experiments are present, and the model described herein can be used to determine initial model parameters.

The methods and systems described herein can include total T level, SHBG level, albumin level, SHB polymorphisms, clearance rates, circadian rhythms, metabolism levels, LH level, FSH level, T degradation, T diffusion/permeability coefficient, and release speed.

Example 4

The Endocrine Society acknowledges that the methods available for free-T testing are fraught with error and recommends the usage of calculated free-T levels in clinical practice pertaining to mens' health. Research publications and the analyses described herein have confirmed that current free-T calculation methodologies are plagued with bias and variance. A popular algorithm likely overestimates the free-T level and induces uncertainty that reduces the likelihood of treatment initiation.

Hypogonadism in men is a clinical syndrome that results from failure of the testes to produce physiological levels of testosterone (androgen deficiency) and a normal number of spermatozoa due to disruption of one or more levels of the hypothalamic-pituitary-testicular (HPT) axis. Testosterone therapy is indicated for the treatment of men with classical androgen deficiency syndromes and aims to induce and maintain secondary sex characteristics and improve sexual function, sense of well-being, and bone mineral density.

A number of testosterone formulations have been approved for the treatment of hypogonadism in men, including injectable testosterone esters, testosterone transdermal patch, transdermal testosterone gels, buccal adhesive testosterone tablets, and testosterone pellets. While transdermals represented 80% of an almost $2.2 Billion market in 2012, little has been done to alleviate the marked inter-indivudual variability in serum testosterone levels in hypognadal men on testosterone replacemement therapy (TRT). This variability has been particularly striking with the transdermal gel formulations and data suggests that more than 50% of men on the recommended initial 5 g/1% testosterone gel do not achieve testosterone levels in the target range. Additionally, approximately 10 to 15% of treated men will have testosterone levels above the upper limit of the normal range, rendering them at risk for adverse events. Interestingly, it is widely proven that Testosterone prescription use indicates that a large fraction (nearly 50%) of men that are started on testosterone therapy discontinue testosterone treatment within 1.0 to 3.5 months and never re-fill their prescription.

A survey of hypogonadal men treated in the Northeastern VA system also reveals a median DOT of 28 days. Thus, a majority of hypogonadal men started on testosterone therapy discontinue testosterone therapy within 3.5 months. It is contemplated herein that a major cause of treatment discontinuation is the failure to achieve the desired therapeutic effect because of suboptimal on-treatment testosterone levels. Monitoring of on-treatment free testosterone levels and appropriate adjustment of testosterone dose to achieve therapeutic levels are necessary for achieving optimal treatment effects and retaining patients on therapy.

The methods, assays, and systems described herein permit the calculation of free testosterone concentrations based on serum total testosterone and SHBG concentrations, and provide specific guidance on dose adjustment needed to achieve the target free testosterone concentration. They further provide a mechanism for enhancing physician-patient engagement, aid the practicing clinician in optimizing the TRT dose to achieve desired on-treatment free testosterone levels that improves treatment outcomes, and retain patients on therapy for a significantly longer period of time than the current median duration.

Example 5

Binding proteins (e.g. SHBG, albumin, orosomucoid and transcortin) and testosterone (T) dynamically interact in multiple steps to regulate testosterone availability.

Circulating testosterone is bound mostly to plasma proteins, sex-hormone binding globulin (SHBG) and albumin. There are several states in which the testosterone and binding proteins are distributed. They continually re-partition into a series of states that are in conformational equilibria. The populations of the intermediate states redistribute as the concentrations of testosterone and binding proteins change. In one of its embodiments (as an example), SHBG exists in two distinct states in the solution governed by a unimolecular equilibrium constant. Both states are capable of binding T and upon binding T, they proceed to the corresponding states with one monomer bound to T and the other monomer is unoccupied within the dimer. The binding of first T induces allosteric changes in monomer that is still unoccupied and therefore results in a distinct change in affinity for the second molecule of T for the SHBG dimer Consistent with the crystal structure of liganded SHBG, Binding of the second molecule to either of the intermediates results in the identical state of fully occupied SHBG dimer.

In one embodiments, free testosterone is calculated as described below.

The relative population of the intermediates is closely coupled through the multiple equilibria and dynamically readjust. Accordingly, testosterone's binding to SHBG cannot be described as a simple linear equation of ligand binding equilibrium. Described herein is a multi-species allostery model, e.g., in LabVIEW framework, that fits the experimental data and permits the development of a set of parameters that accurately described the multiple interactions listed below:

$$ST + S_2T + S_1T + S_1 + S = S_0$$

$$T + ST + 2 \cdot S_2T + S_1T + T_f + alb.T = T_0$$

$$T = T_f$$

$$-k_{1+}S \cdot T + k_{1-}ST + k_{11-}S_1 - k_{11+}S = 0$$

$$-k_{3+}S_1 \cdot T + k_{3-}S_1T - k_{11-}S_1 + k_{11+}S = 0$$

$$-k_{2+}ST \cdot T + k_{1+}S \cdot T - k_{1-}ST + k_{2-}S_2T = 0$$

$$k_{2+}ST \cdot T + k_{4+}S_1T \cdot T - (k_{4-} + k_{2-}) \cdot S_2T = 0$$

$$alb.T + alb = alb_0$$

Figure 5B:
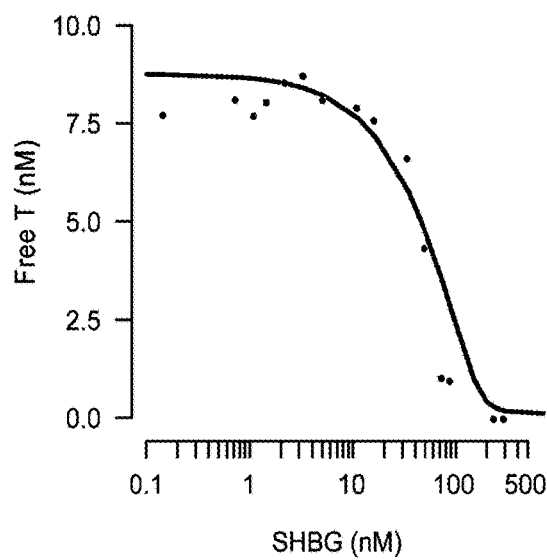
FIG. 5B depicts a graph of the depletion curve. A constant concentration of testosterone (8.7 nM) was incubated with increasing SHBG concentrations. Free testosterone concentration is plotted against SHBG concentration. Solid line represents the fit of data to new Multi-step Dynamic Binding Model with Complex Allostery. The depletion of free testosterone by increasing SHBG concentrations is best described by the new Multi-step Dynamic Binding Model with Complex Allostery.
Figure 5C:
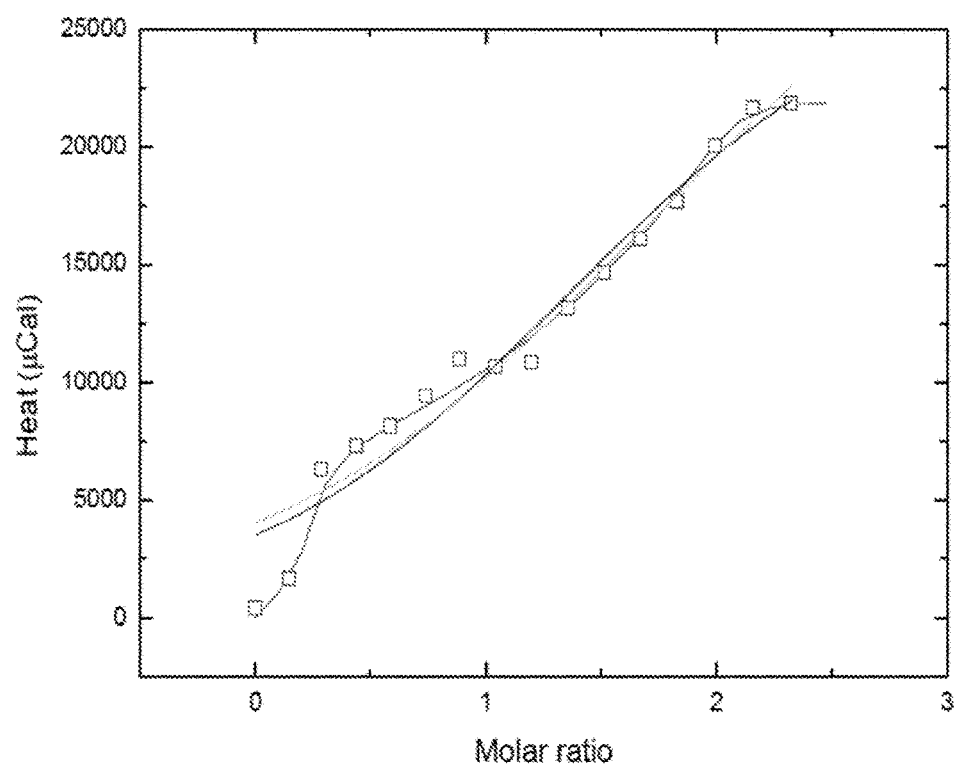
FIG. 5C depicts a graph of the heat of testosterone and SHBG association measured by isothermal calorimetry. The integrated ITC curve was generated after subtracting the buffer heats. SHBG starting concentration is 5 μM. Experimental points are shown by (■), and fit of the data to the new Multi-step Dynamic Binding Model with Complex Allostery model is shown by a solid line.

Using a set of equilibrium constants derived from the fits to the biophysical data provided in FIGS. 5A, 5B, and 5C, an exemplary solution of the series of equations is presented below to calculate free T. The solution below doesn't imply presence of a unique equation rather that distinct equations can be developed to achieve accurate calculation of free T with a model of interaction that involves (and is not limited to) inter-subunit allostery in SHBG, regulation of free T levels by albumin and conformational states of binding proteins (albumin and SHBG).

$$Tf^*(4311602270490^*T\_0-792951348000^*S\_0+ \\ 95385510^*Alb0-5341588560000)+Tf^2^* \\ (916102610798^*T\_0-210702480309^*S\_0+ \\ 153989202^*Alb0-8623204540980)+Tf^3^* \\ (18366076550^*T\_0-22591273900^*S\_0+ \\ 32723450^*Alb0-1832205221596)+Tf^4^* \\ (1539342900^*T\_0-3079192900^*S\_0+ \\ 657100^*Alb0-36732153100)+ \\ 2670794280000^*T\_0+Tf^5^*(55000^*T\_0+ \\ 110000^*S\_0+55000^*Alb0-3078685800)+ \\ 110000^*Tf^6=0$$

In a number of disease states and conditions, the concentrations of binding proteins are altered and the determination of free testosterone is necessary for making a diagnosis of hypogonadism and evaluation of gonadal status. The common conditions in which SHBG concentrations are decreased include but are not limited to obesity, diabetes mellitus, and hypothyroidism. Correspondingly there are patient symptoms that may be clinical or subclinical presentation of Androgen related disorders that may alter the Testosterone and SHBG concentrations such as hirsuitism, muscular dystrophy, Androgen insensitivity, acne, polycystic ovarian syndrome, Acromegaly, Anorexia, Androgen expressing tumors etc. It is specifically contemplated herein that the methods, systems, and assays described herein can be used either for patients diagnosed with an androgen disorder or patients who are suspected of having an androgen disorder, e.g. those subjects exhibiting one or more symptoms or risk factors for an androgen disorder. It is specifically contemplated herein that the methods, systems, and assays described herein can be used either for patients diagnosed with a disease or condition that arises from or is characterized by an abnormal level of testosterone or SHBG or patients who are suspected of having a disease or condition that arises from or is characterized by an abnormal level of testosterone or SHBG, e.g. those subjects exhibiting one or more symptoms or risk factors for a disease or condition that arises from or is characterized by an abnormal level of testosterone or SHBG.

Similarly, SHBG concentrations are increased in hyperthyroidism, chronic infections such as HIV, and hepatitis B and C, and old age. Albumin concentrations are decreased in cancer cachexia, malnutrition, liver disease, nephrotic syndrome., and in chronic infections. It is specifically contemplated herein that the methods, systems, and assays described herein can be used either for patients diagnosed with a disease or condition that arises from or is characterized by an abnormal level of albumin or SHBG or patients who are suspected of having a disease or condition that arises from or is characterized by an abnormal level of albumin or SHBG, e.g. those subjects exhibiting one or more symptoms or risk factors for a disease or condition that arises from or is characterized by an abnormal level of albumin or SHBG.

In all these conditions, total testosterone concentrations are affected by the changes in the binding protein concentrations and do not accurately reflect androgen status. Therefore, in these conditions, the determination of free testosterone concentrations is essential for accurately assessing androgen status and making an accurate diagnosis of hypogonadism or androgen excess. Therefore, in evaluating patients for hypogonadism or androgen deficiency, pubertal disorders, hirsutism, androgenic alopecia, infertility, or gynecomastia, who have one or more of the conditions listed above that alter binding protein concentrations, an accurate determination of free testosterone concentrations is necessary.

The diagnosis of hypogoandism is based on ascertainment of low total testosterone levels, which can be misleading in conditions listed above in which binding protein concentrations are affected. Therefore, in these patients with alterations in binding protein concentrations, the diagnosis should be based on free testosterone levels. The Endocrine Society has published cut-off levels that define low free testosterone levels (Bhasin et al, Testosterone Therapy of Men with Androgen Deficiency Syndromes: An Endocrine Society Guideline. JCEM 2010). These cut-off levels for free testosterone were based on methods which are demonstrated herein to be inaccurate. Using the methods, assays, and/or systems described herein, new cut-offs for defining low free testosterone in men in different decades of age are provided herein. These reference values will facilitate accurate diagnosis of hypogonadism in men. Based on the distribution of free testosterone in men, the lower limit of the normal range is determined to be 114.6 pg/mL.

Using the methods, assays, and systems described herein, the optimal range of free testosterone concentrations that should be targeted in hypogonadal men receiving testosterone replacement therapy have also been determined. The treatment of hypogonadism with testosterone is currently suboptimal. The analyses of clinical trials data described herein demonstrate that a large fraction of hypogonadal men treated with testosterone therapy have testosterone levels in the subtherapeutic range.

The current Endocrine Society guidelines suggest the use of total testosterone levels to guide therapy, which as discussed above, do not provide an accurate assessment of the androgen status. The free testosterone concentrations, determined the new method described herein, can provide accurate assessment of the adequacy of testosterone therapy in hypogonadal men. Based on the new data on the distribution of free testosterone levels in healthy men the target range of free testosterone has been determined to be 164 to 314 pg/ml (mean+/−1SD). If the on-treatment free testosterone concentrations determined using the methods described herein are outside this range, the dose of testosterone should be adjusted using the methods described herein to achieve testosterone levels in the target therapeutic range to maximize benefits and reduce the risks. Furthermore, the initial dose of testosterone therapy can be determined using the methods, assays, and/or systems described herein, e.g. the dosimeter methods described herein.

In some embodiments, the methods, assays, and/or systems described herein pemit the determination or measurement of free testosterone in a subject and the determination of a dose of testosterone. In some embodiments, the subject can be classified, e.g., as having low or normal testosterone levels, as needing or not needing testosterone therapy, or as at risk or not at risk of having or developing an androgen disorder. In some embodiments, additional clinical symptoms can be used in classifying a subject. In some embodiments, multiple solutions can be found for set of equations described herein, dependent upon accuracy vs. computational intensiveness. In some embodiments, the model described herein can be subjected to spline-based linearization based on marker ranges.

In some embodiments, the methods, assays, and/or systems described herein can comprise the calculation of a suitable dosage and/or determining the effect an existing dosage has on the the subject's free testosterone levels. In some embodiments, the methods, assays, and/or systems described herein can comprise adjusting a subject's dose, e.g., to a dose that will cause their free testosterone levels to be normal. In some embodiments, the adjustment can be step-wise adjustment. In some embodiments, the adjustment can comprise multiple steps or changes in order to reach a final or target dosage. In some embodiments, the methods, assays, and/or systems described herein can comprise conversion of a calculated dose to available formulations, e.g., determining the dosage present in a given formulation that is necessary in order to deliver a particular dosage or maintain a particular dosage in a subject. In some embodiments, the methods, assays, and/or systems described herein can comprise dosing changes that are counterintuitive due to control loop characterization and for other known or unknown physiological, behavioral, psychological or environmental reasons. In some embodiments, the methods, assays, and/or systems described herein can comprise additional steps to characterize, e.g., individual clearance rates, individual uptake rates (e.g., skin permeability), or other factors, e.g. changes in metabolism or biochemistry caused by other ailments, conditions, or environmental changes that influence the testosterone balance and/or levels. In some embodiments, the subject can be a hard to treat subject, e.g., one that does not respond normally to testosterone therapy.

What is claimed herein is:

1. A method of diagnosing and treating an androgen disorder in a patient comprising the following steps:
 a) obtaining a biological sample from the patient,
 b) measuring in the biological sample obtained in step a)

i. a total concentration of sex-hormone binding globulin ("SHBG"), which is a dimer having a first monomer and a second monomer,
ii. a total concentration of testosterone, and
iii. a concentration of albumin;
c) determining the concentration of free testosterone in the biological sample based on (i)-(iii) measured in step b), using an ensemble allostery model representing the binding equilibria (i) between testosterone and the first monomer of the SHBG and between testosterone and the second monomer of the SHGB, wherein the unliganded SHBG has at least two distinct interconverting microstates $S_2$ and $S'_2$, and wherein the first monomer and the second monomer have an allosteric interaction such that each of the microstates binds a first testosterone molecule with a different affinity; and (ii) between testosterone and the albumin;
d) diagnosing the patient with an androgen disorder when the free testosterone concentration determined in step c) is below the lower limit of a normal free testosterone concentration from a healthy individual; and
e) administering an effective amount of testosterone, testosterone derivatives, and/or analogues thereof to the patient diagnosed in step d).

2. The method of claim 1, wherein the step of measuring in the biological sample further comprises measuring in the biological sample
iv. A concentration of at least one non-testosterone steroid.

3. The method of claim 2, wherein the non-testosterone steroid is selected from the group consisting of an estradiol steroid, an estrone steroid, and a dihydrotestosterone steroid.

4. The method of claim 2, wherein the method further comprises the step of determining the concentration of the non-testosterone steroid in the biological sample using the ensemble allostery model comprising readjusting a second equilibria between the microstates upon binding of the non-testosterone steroid molecule to the first monomer and the allosteric interaction between two monomers of the SHBG.

5. The method of claim 1, wherein the step of measuring in the biological sample further comprises measuring in the biological sample
iv. the concentration of one or more analytes.

6. The method of claim 1, wherein the step of measuring in the biological sample further comprises measuring one or more of the concentrations in the biological sample using at least one analytical method.

7. The method of claim 6, wherein the analytical method is selected from the group consisting of an immunoassay and a mass spectrometry-based assay.

8. The method of claim 1, wherein the androgen disorder is selected from the group consisting of a testosterone deficiency, an androgen deficiency, and a hypogonadism disorder.

9. The method of claim 1, wherein the androgen disorder comprises a hyperandrogenic disorder.

10. The method of claim 9, wherein the hyperandrogenic disorder is selected from the group consisting of a polycystic ovary syndrome, an acne disorder, a hirsutism disorder, and an androgenic alopecia disorder.

11. A method of monitoring and optimizing treatment for an androgen disorder in a patient comprising the following steps:
a) obtaining a biological sample from the patient who is on a treatment of the androgen disorder,
b) measuring in the biological sample obtained in step a)
i. a total concentration of sex-hormone binding globulin ("SHBG"), which is a dimer having a first monomer and a second monomer,
ii. a total concentration of testosterone, and
iii. a concentration of albumin;
c) determining the concentration of free testosterone in the biological sample based on (i)-(iii) measured in step b), using an ensemble allostery model representing the binding equilibria (i) between testosterone and the first monomer of the SHBG and between testosterone and the second monomer of the SHGB, wherein the unliganded SHBG has at least two distinct interconverting microstates $S_2$ and $S'_2$, and wherein the first monomer and the second monomer have an allosteric interaction such that each of the microstates binds a first testosterone molecule with a different affinity; and (ii) between testosterone and the albumin;
d) identifying the patient as needing treatment optimization when the free testosterone concentration determined in step c) is below the lower limit of a normal free testosterone concentration from a healthy individual; and
e) optimizing the treatment of the identified patient with the androgen disorder by administering a modified amount of testosterone, testosterone derivatives, and/or analogues thereof to the identified patient.

12. The method of claim 11, wherein the androgen disorder is selected from the group consisting of a testosterone deficiency, an androgen deficiency, and a hypogonadism disorder.

13. The method of claim 11 wherein the androgen disorder comprises a hyperandrogenic disorder.

14. The method of claim 13, wherein the hyperandrogenic disorder is selected from the group consisting of a polycystic ovary syndrome, an acne disorder, a hirsutism disorder, and an androgenic alopecia disorder.

15. The method of claim 11, wherein optimizing treatment further comprises the step of:
d) adjusting the dose of administered testosterone, testosterone derivatives, and/or analogues thereof for treatment of the androgen disorder.

16. The method of claim 15, wherein the androgen disorder is selected from the group consisting of a testosterone deficiency, an androgen deficiency, and a hypogonadism disorder.

17. The method of claim 15, wherein the androgen disorder is a hyperandrogenic disorder.

18. The method of claim 17, wherein the hyperandrogenic disorder is selected from the group consisting of a polycystic ovary syndrome, an acne disorder, a hirsutism disorder, and an androgenic alopecia disorder.

19. A method of treating an androgen disorder in a patient comprising administering an effective amount of testosterone, testosterone derivatives, and/or analogues thereof to the patient wherein the patient's free testosterone concentration is below the lower limit of a normal free testosterone concentration from a healthy individual, wherein the patient's free testosterone concentration is determined based on:
i. total concentration of sex-hormone binding globulin ("SHBG"), which is a dimer having a first monomer and a second monomer,
ii. total concentration of testosterone, and
iii. concentration of albumin;
and wherein the free testosterone concentration is calculated by an ensemble allostery model representing the binding equilibria (i) between testosterone and the first monomer of the SHBG and between testosterone and the second monomer of the SHGB, wherein the unliganded SHBG has at least two distinct interconverting microstates $S_2$ and $S'_2$, and wherein the first monomer and the second monomer have an allosteric interaction such that each of the microstates binds a first testosterone molecule with a different affinity; and (ii) between testosterone and the albumin.

* * * * *